US009045742B2

(12) United States Patent
Curtiss, III et al.

(10) Patent No.: US 9,045,742 B2

(45) Date of Patent: Jun. 2, 2015

(54) **RECOMBINANT *EDWARDSIELLA* BACTERIUM**

(75) Inventors: Roy Curtiss, III, Paradise Valley, AZ (US); Javier Santander, Tempe, AZ (US)

(73) Assignee: The Arizona Board of Regents for and on behalf of Arizona State University, Tempe, AZ (US)

(*) Notice: Subject to any disclaimer, the term of this patent is extended or adjusted under 35 U.S.C. 154(b) by 128 days.

(21) Appl. No.: 12/789,869

(22) Filed: May 28, 2010

(65) Prior Publication Data

US 2010/0303863 A1 Dec. 2, 2010

Related U.S. Application Data

(60) Provisional application No. 61/182,569, filed on May 29, 2009.

(51) Int. Cl.

| | |
|---|---|
| ***A01N 63/00*** | (2006.01) |
| ***A01N 65/00*** | (2009.01) |
| ***A61K 39/02*** | (2006.01) |
| ***C12N 1/36*** | (2006.01) |
| ***C07K 14/24*** | (2006.01) |
| *A61K 39/00* | (2006.01) |

(52) U.S. Cl.

CPC . *C12N 1/36* (2013.01); *A61K 39/02* (2013.01); *A61K 2039/523* (2013.01); *C07K 14/24* (2013.01)

(58) Field of Classification Search

CPC ...... C12N 15/09; C12N 15/63; C12N 15/635; C12N 15/64; C12N 15/66; C12N 15/74; C12N 2830/00; C12N 2830/55; C12N 15/00; A61K 2039/552; A61K 2039/523; A61K 35/66; A61K 35/74; A61K 39/00; A61K 39/0208; A61K 2039/51; A61K 2039/52

See application file for complete search history.

(56) References Cited

U.S. PATENT DOCUMENTS

| | | | | |
|---|---|---|---|---|
| 4,190,495 | A | 2/1980 | Curtiss, III | |
| 4,888,170 | A | 12/1989 | Curtiss, III | |
| 4,968,619 | A | 11/1990 | Curtiss, III | |
| 5,210,035 | A | 5/1993 | Stocker | |
| 5,294,441 | A | 3/1994 | Curtiss, III | |
| 5,387,744 | A | 2/1995 | Curtiss | |
| 5,389,368 | A | 2/1995 | Gurtiss, III | |
| 5,424,065 | A | 6/1995 | Curtiss, III | |
| 5,468,485 | A | 11/1995 | Curtiss, III | |
| 5,536,658 | A * | 7/1996 | Shotts et al. | 435/252.3 |

(Continued)

FOREIGN PATENT DOCUMENTS

| | | | |
|---|---|---|---|
| EP | 0315682 | B1 | 12/1993 |
| EP | 0381706 | B1 | 4/1995 |

(Continued)

OTHER PUBLICATIONS

Verjan et al., (Applied and Environmental Microbio. Sep. 2005. vol. 71(9): 5654-5658).*

(Continued)

*Primary Examiner* — Ja'Na Hines

(74) *Attorney, Agent, or Firm* — Polsinelli PC; Rebecca C. Riley-Vargas

(57) ABSTRACT

The present invention encompasses a recombinant *Edwardsiella* bacterium, and compositions and methods of use thereof.

19 Claims, 35 Drawing Sheets

(56) References Cited

U.S. PATENT DOCUMENTS

| | | | | |
|---|---|---|---|---|
| 5,654,184 | A | 8/1997 | Curtiss, III | |
| 5,656,488 | A | 8/1997 | Curtiss, III | |
| 5,672,345 | A | 9/1997 | Curtiss, III | |
| 5,679,880 | A | 10/1997 | Curtiss, III | |
| 5,686,079 | A | 11/1997 | Curtiss, III | |
| 5,817,317 | A | 10/1998 | Titball | |
| 5,827,705 | A | 10/1998 | Dean | |
| 5,840,483 | A | 11/1998 | Curtiss, III | |
| 5,855,879 | A | 1/1999 | Curtiss III | |
| 5,855,880 | A | 1/1999 | Curtiss, III | |
| 5,961,983 | A | 10/1999 | Brey et al. | |
| 6,010,705 | A * | 1/2000 | Thune et al. | 424/234.1 |
| 6,024,961 | A | 2/2000 | Curtiss, III | |
| 6,180,614 | B1 * | 1/2001 | Davis | 514/44 R |
| 6,248,329 | B1 | 6/2001 | Chandrashekar et al. | |
| 6,350,454 | B1 * | 2/2002 | Thune | 424/200.1 |
| 6,383,496 | B1 | 5/2002 | Curtiss, III | |
| 6,399,074 | B1 | 6/2002 | Roland | |
| 6,403,094 | B1 | 6/2002 | Titball | |
| 6,610,529 | B1 | 8/2003 | Curtiss, III | |
| 6,780,405 | B1 | 8/2004 | Curtiss, III | |
| 6,872,547 | B1 | 3/2005 | Curtiss, III | |
| 6,969,513 | B2 | 11/2005 | Galen | |
| 7,083,794 | B2 | 8/2006 | Curtiss, III | |
| 7,195,757 | B2 | 3/2007 | Curtiss, III | |
| 7,205,125 | B2 | 4/2007 | Castillo | |
| 7,341,860 | B2 | 3/2008 | Curtiss, III | |
| 7,871,604 | B1 | 1/2011 | Curtiss, III | |
| 7,968,101 | B2 | 6/2011 | Kawaoka | |
| 8,133,493 | B2 | 3/2012 | Curtiss, III | |
| 8,445,254 | B2 | 5/2013 | Curtiss, III et al. | |
| 8,465,755 | B2 | 6/2013 | Curtiss, III et al. | |
| 2003/0031683 | A1 | 2/2003 | Curtiss, III | |
| 2003/0175772 | A1 | 9/2003 | Wang | |
| 2004/0077556 | A1 | 4/2004 | Chinery | |
| 2004/0101531 | A1 | 5/2004 | Curtiss, III | |
| 2004/0120962 | A1 * | 6/2004 | Curtiss et al. | 424/184.1 |
| 2004/0137003 | A1 | 7/2004 | Curtiss, III | |
| 2004/0203039 | A1 | 10/2004 | Hensel | |
| 2005/0036987 | A1 | 2/2005 | Pawelek | |
| 2005/0106175 | A1 | 5/2005 | Montaines | |
| 2005/0106176 | A1 | 5/2005 | Curtis, III | |
| 2005/0118193 | A1 | 6/2005 | Andino-Pavlovsky et al. | |
| 2006/0140975 | A1 | 6/2006 | Curtiss, III | |
| 2006/0171917 | A1 | 8/2006 | Campbell | |
| 2006/0206961 | A1 | 9/2006 | Cirpus | |
| 2006/0233829 | A1 * | 10/2006 | Curtiss, III | 424/200.1 |
| 2006/0234346 | A1 | 10/2006 | Retallack | |
| 2006/0275255 | A1 | 12/2006 | Gudkov | |
| 2007/0025981 | A1 | 2/2007 | Szalay | |
| 2008/0096809 | A1 | 4/2008 | Shai | |
| 2008/0248066 | A1 | 10/2008 | Dubensky, Jr. | |
| 2009/0175829 | A1 | 7/2009 | Forbes | |
| 2010/0124558 | A1 | 5/2010 | Curtiss, III | |
| 2010/0154293 | A1 | 6/2010 | Hom et al. | |
| 2010/0255022 | A1 | 10/2010 | Prescott et al. | |
| 2010/0285592 | A1 | 11/2010 | Curtiss, III | |
| 2010/0317084 | A1 | 12/2010 | Curtiss, II | |
| 2011/0033501 | A1 | 2/2011 | Curtiss, III et al. | |
| 2011/0256181 | A1 | 10/2011 | Curtiss, III | |
| 2011/0287052 | A1 | 11/2011 | Curtiss, III et al. | |
| 2012/0087946 | A1 | 4/2012 | Curtiss III | |
| 2013/0004537 | A1 | 1/2013 | Curtiss, III et al. | |
| 2013/0171190 | A1 | 7/2013 | Curtiss III et al. | |

FOREIGN PATENT DOCUMENTS

| | | | | |
|---|---|---|---|---|
| EP | 0465560 | B1 | 6/1996 | |
| EP | 0500699 | B1 | 6/1998 | |
| EP | 0558631 | B1 | 3/1999 | |
| EP | 0433372 | B1 | 6/2002 | |
| EP | 1030690 | B1 | 7/2002 | |
| EP | 0556333 | B1 | 3/2003 | |
| EP | 1326960 | B1 | 12/2004 | |
| EP | 0832255 | B1 | 12/2005 | |
| EP | 1537214 | B1 | 3/2006 | |
| EP | 1292687 | B1 | 8/2006 | |
| WO | 88/09669 | A1 | 12/1988 | |
| WO | 89/03427 | A1 | 4/1989 | |
| WO | 90/02484 | A1 | 3/1990 | |
| WO | 90/11687 | A1 | 10/1990 | |
| WO | 90/11688 | A1 | 10/1990 | |
| WO | 90/12086 | A1 | 10/1990 | |
| WO | 91/06317 | A1 | 5/1991 | |
| WO | 92/08486 | A1 | 5/1992 | |
| WO | 92/09684 | A1 | 6/1992 | |
| WO | 93/04202 | A1 | 3/1993 | |
| WO | 94/24291 | A2 | 10/1994 | |
| WO | 94/24291 | A3 | 12/1994 | |
| WO | 96/40947 | A1 | 12/1996 | |
| WO | 99/25387 | A1 | 5/1999 | |
| WO | 01/83785 | A2 | 11/2001 | |
| WO | 02/30457 | A2 | 4/2002 | |
| WO | 01/83785 | A3 | 6/2002 | |
| WO | 02/59292 | A2 | 8/2002 | |
| WO | 02/30457 | A3 | 1/2003 | |
| WO | 02/30457 | A3 | 7/2003 | |
| WO | 02/59292 | A3 | 7/2003 | |
| WO | 03/079792 | A1 | 10/2003 | |
| WO | WO 03/079792 | A1 * | 10/2003 | A01N 63/00 |
| WO | 03/096812 | A1 | 11/2003 | |
| WO | WO 03/102160 | * | 12/2003 | |
| WO | 2004/020643 | A2 | 3/2004 | |
| WO | 2004/020643 | A3 | 4/2004 | |
| WO | 2005/001069 | A1 | 1/2005 | |
| WO | WO 2005/001069 | A1 * | 1/2005 | C12N 1/36 |
| WO | 2008/141226 | A2 | 11/2008 | |
| WO | 2009/025888 | A2 | 2/2009 | |
| WO | WO 2009/025888 | * | 2/2009 | C12N 1/21 |
| WO | 2009/046449 | A1 | 4/2009 | |
| WO | 2009/046451 | A1 | 4/2009 | |
| WO | 2010/045620 | A1 | 4/2010 | |
| WO | 2010/078584 | A1 | 8/2010 | |
| WO | 2010/135563 | A1 | 11/2010 | |
| WO | 2011/091291 | A1 | 7/2011 | |
| WO | 2011/150421 | A2 | 12/2011 | |
| WO | 2012087483 | A1 | 6/2012 | |

OTHER PUBLICATIONS

Waltman et al., (Applied and Environ. Microbio. 1986. vol. 51(1):101-104).*

Kotton et al., Enteric pathogens as vaccine vectors for foreign antigen delivery. Infect. Immun., 2004, pp. 5535-5547, vol. 72.

Lee et al., Characterization of recent H5 subtype avian influenza viruses from US poultry. Avian Pathol., 2004, pp. 288-297, vol. 33.

Lee et al., Mechanism of araC autoregulation and the domains of two overlapping promoters, PC and PBAD, in the L-arabinose regulatory region of *Escherichia coli*. Proc. Natl. Acad. Sci. U S A, 1981, pp. 752-756, vol. 78.

Li et al., A sopB Deletion Mutation Enhances the Immunogenicity and Protective Efficacy of a Heterologous Antigen Delivered by Live Attenuated *Salmonella enterica* Vaccines. Infection and Immunity, 2008, pp. 5238-5246, vol. 76, No. 11.

Lee et al., Trigger factor retards protein export in *Escherichia coli*. J Biol Chem, 2002, pp. 43527-43535, vol. 277.

Lefeber et al., Th1-directing adjuvants increase the immunogenicity of oligosaccharide-protein conjugate vaccines related to *Streptococcus pneumoniae* type 3. Infect Immun, 2003, pp. 6915-6920, vol. 71.

Loessner et al., Differential effect of auxotrophies on the release of macromolecules by *Salmonella enterica* vaccine strains. FEMS Microbiol. Lett., 2006, pp. 81-88, vol. 265.

Loewen et al., Genetic mapping of katF, a locus that with katE affects the synthesis of a second catalase species in *Escherichia coli*. J Bacteriol, 1984, pp. 668-675, vol. 160.

Luytjes et al., Amplification, expression, and packaging of foreign gene by influenza virus. Cell, 1989, pp. 1107-1113, vol. 59.

Malley et al., CD4+ T cells mediate antibody-independent acquired immunity to pneumococcal colonization. PNAS, 2005, pp. 4848-4853, vol. 102.

(56) References Cited

OTHER PUBLICATIONS

Massin et al., Cloning of the chicken RNA polymerase I promoter and use for reverse genetics of influenza A viruses in avian cells. J. Virol., 2005, pp. 13811-13816, vol. 79.
Matthay et al., Evaluation of the opsonic requirements for phagocytosis of *Streptococcus pneumoniae* serotypes VII, XIV, and XIX by chemiluminescence assay. Infect Immun, 1981, pp. 228-235, vol. 31.
McClelland et al., Complete genome sequence of *Salmonella enterica* serovar *typhimurium* LT2. Nature, 2001, pp. 852-856, vol. 413, No. 6858.
McDaniel et al., Monoclonal antibodies against protease sensitive pneumococcal antigens can protect mice from fatal infection with *Streptococcus pneumoniae*. J. Exp. Med., 1984, pp. 368-397, vol. 160.
McDaniel et al., Use of insertional inactivation to facilitate studies of biological properties of pneumococcal surface protein A (PspA). J. Exp. Med., 1987, pp. 381-394, vol. 165.
Mesika et al., A regulated, NF κb-assisted import of plasmid DNA into mammalian cell nuclei. Mol. Ther., 2001, pp. 653-657, vol. 3.
Miller et al., A novel suicide vector and its use in construction of insertion mutations: osmoregulation of outer membrane proteins and virulence determinants in *Vibrio cholerae* requires toxR. J Bacteriol, 1988, pp. 2575-2583, vol. 170.
Miller et al., Bacteriophage T4 genome. Microbiol Mol Biol Rev, 2003, pp. 86-156, vol. 67, No. 1.
Molinari et al., The annual impact of seasonal influenza in the US: measuring disease burden and costs. Vaccine, 2007, pp. 5086-5096, vol. 25.
Mulvey et al., Regulation of transcription of katE and katF in *Escherichia coli*. J Bacteriol, 1990, pp. 6713-6720, vol. 172.
Murti et al., Localization of RNA polymerases on influenza viral ribonucleoproteins by immunogold labeling. Virology, 1988, pp. 562-566, vol. 164.
Nardelli-Haefliger et al., Human papillomavirus type 16 virus-like particles expressed in attenuated *Salmonella typhimurium* elicit mucosal and systemic neutralizing antibodies in mice. Infect Immun, 1997, pp. 3328-3336, vol. 65.
Nayak et al., A live recombinant avirulent oral *Salmonella* vaccine expressing pneumococcal surface protein A induces protective responses against *Streptococcus pneumoniae*. Infect Immun., 1998, pp. 3744-3751, vol. 66.
Neumann et al., An improved reverse genetics system for influenza A virus generation and its implications for vaccine production. Proc. Natl. Acad. Sci. USA, 2005, pp. 16825-16829, vol. 102.
Neumann et al., Generation of influenza A viruses entirely from cloned cDNAs. Proc. Natl. Acad. Sci. USA, 1999, pp. 9345-9350, vol. 96.
Neumann et al., RNA polymerase I-mediated expression of influenza viral RNA molecules. Virology, 1994, pp. 477-479, vol. 202.
Nickerson et al., Role of sigma factor RpoS in initial stages of *Salmonella typhimurium* infection. Infect Immun, 1997, pp. 1814-1823, vol. 65.
Noda et al., Architecture of ribonucleoprotein complexes in influenza A virus particles. Nature, 2006, pp. 490-492, vol. 439.
Oehler et al., The three operators of the lac operon cooperate in repression. EMBO J, 1990, pp. 973-979, vol. 9, No. 4.
Ogunniyi et al., Contributions of Pneumolysin, Pneumococcal Surface Protein A (PspA), and PspC to Pathogenicity of *Streptococcus pneumoniae* D39 in a Mouse Model. Infect. Immun., 2007, pp. 1843-1851, vol. 75.
Osterholm, Preparing for the next pandemic. N. Engl. J. Med., 2005, pp. 1839-1842, vol. 352.
Ozaki et al., Generation of high-yielding influenza A viruses in African green monkey kidney (Vero) cells by reverse genetics. J. Virol., 2004, pp. 1851-1857, vol. 78.
Park et al., Engineered viral vaccine constructs with dual specificity: avian influenza and Newcastle disease. Proc. Natl. Acad. Sci. USA, 2006, pp. 8203-8208, vol. 103.
Pascual et al., Expression of Recombinant Enterotoxigenic *Escherichia coli* Colonization Factor Antigen I by *Salmonella typhimurium* Elicits a Biphasic T Helper Cell Response. Infect. Immun., 1999, pp. 6249-6256, vol. 67.
Pashine et al., Th1 dominance in the immune response to live *Salmonella typhimurium* requires bacterial invasiveness but not persistence. Int. Immunol., 1999, pp. 481-489, vol. 11.
Peterson et al., RpoS proteolysis is regulated by a mechanism that does not require the SprE (RssB) response regulator phosphorylation site. J Bacteriol, 2004, pp. 7403-7410, vol. 186.
Pizarro-Cerda et al., The bacterial signal molecule, ppGpp, regulates *Salmonella* virulence nucleic acid sequence expression. Mol Microbiol, 2004, pp. 1827-1844, vol. 52, No. 6.
Prouty et al., *Salmonella enterica* serovar *typhimurium* invasion is repressed in the presence of bile. Infect Immun, 2000, pp. 6763-6769, vol. 68.
Quinlivan et al., Attenuation of equine influenza viruses through truncations of the NS1 protein. J. Virol., 2005, pp. 8431-8439, vol. 79.
Rand, Crystal violet can be used to visualize DNA bands during gel electrophoresis and to improve cloning efficiency. Tech. Tips Online, 1996 http://www.science-direct.com/science/journal/13662120.
Roberts et al., Oral vaccination against tetanus: comparison of the immunogenicities of *Salmonella* strains expressing fragment C from the nirB and htrA promoters. Infect. Immun., 1998, pp. 3080-3087, vol. 66.
Romeo et al., Genetic regulation of glycogen biosynthesis in *Escherichia coli*: in vitro effects of cyclic AMP and guanosine 5'-diphosphate 3'-diphosphate and analysis of in vivo transcripts. J Bacteriol, 1989, pp. 2773-2782, vol. 171.
Sadler et al., A perfectly symmetric lac operator binds the lac repressor very tightly. Proc Natl Acad Sci U S A, 1983, pp. 6785-6789, vol. 80, No. 22.
Saeland et al., Serum samples from infants vaccinated with a pneumococcal conjugate vaccine, PncT, protect mice against invasive infection caused by *Streptococcus pneumoniae* serotypes 6A and 6B. J Infect Dis, 2001, pp. 253-260, vol. 183.
Schodel et al., Hybrid hepatitis B virus core-pre-S proteins synthesized in avirulent *Salmonella typhimurium* and *Salmonella typhi* for oral vaccination. Infect Immun, 1994, pp. 1669-1676, vol. 62, No. 5.
Schodel, Recombinant avirulent *Salmonellae* as oral vaccine carriers. Infection, 1992, pp. 1-8, vol. 20.
Schuchat et al., Bacterial meningitis in the United States in 1995. Active Surveillance Team. N Engl J Med, 1997, pp. 970-976, vol. 337.
Schulman et al., Independent variation in nature of hemagglutinin and neuraminidase antigens of influenza virus: distinctiveness of hemagglutinin antigen of Hong Kong-68 virus. Proc. Natl. Acad. Sci. USA, 1969, pp. 326-333, vol. 63.
Siegele et al., Gene Expression from plasmids containing the araBAD promoter at subsaturating inducer concentrations represents mixed populations. Proc Natl Acad Sci U S A, 1997, pp. 8168-8172, vol. 94, No. 15.
Simonsen et al., The impact of influenza epidemics on hospitalizations. J. Infect. Dis., 2000, pp. 831-837, vol. 181.
Alonso et al, Anti-polysaccharide immunoglobulin isotype levels and opsonic activity of antisera: relationships with protection against *Streptococcus pneumoniae* infection in mice. J Infect Dis, 1995, pp. 562-565, vol. 172.
Amann et al., Tightly regulated tac promoter vectors useful for the expression of unfused and fused proteins in *Escherichia coli*. Nucleic acid sequence, 1988. pp. 301-315, vol. 69, No. 2.
Anderson et al., Delivery of the Pertactin/P.69 polypeptide of *Bordetella pertussis* using an attenuated *Salmonella typhimurium* vaccine strain: expression levels and immune response. Vaccine, 1996, pp. 1384-1390 , vol. 14, No. 14.
Aravind et al., The HD domain defines a new superfamily of metal-dependent phosphohydrolases. Trends Biochem Sci, 1998, pp. 469-472, vol. 23.
Arricau et al., The RcsB-RcsC regulatory system of *Salmonella typhi* differentially modulates the expression of invasion proteins, flagellin and Vi antigen in response to osmolarity., Mol Microbiol, 1998, pp. 85-50, vol. 29, No. 3.

(56) References Cited

OTHER PUBLICATIONS

Arulanandam et al., Intranasal vaccination with pneumococcal surface protein A and interleukin-12 augments antibody-mediated opsonization and protective immunity against *Streptococcus pneumoniae* infection. Infect Immun, 2001, pp. 6718-6724, vol. 69.
Audia et al., Breaking through the acid barrier: an orchestrated response to proton stress by enteric bacteria. Int J Med Microbiol, 2001, pp. 97-106, vol. 291.
Battesti et al., Acyl carrier protein/SpoT interaction, the switch linking SpoT-dependent stress response to fatty acid metabolism. Mol Microbiol, 2006, pp. 1048-1063, vol. 62.
Blattner et al., The complete genome sequence of *Escherichia coli* K-12. Science, 1997, pp. 1453-1474, vol. 277.
Branger et al., Oral vaccination with different antigens from *Yersinia pestis* KIM delivered by live attenuated *Salmonella typhimurium* elicits a protective immune response against plague. Adv Exp Med Biol, 2007, pp. 387-399, vol. 603.
Briles et al. The potential for using protein vaccines to protect against otitis media caused by *Streptococcus pneumoniae*. Vaccine, 2001, pp. S87-S95, vol. 19, Suppl 1.
Brubaker, Interleukin-10 and inhibition of innate immunity to Yersiniae: roles of Yops and LcrV (V antigen). Infect Immun, 2003, pp. 3673-3681, vol. 71.
Brubaker, The Vwa+ virulence factor of Yersiniae: the molecular basis of the attendant nutritional requirement for Ca2+. Rev Infect Dis, 1983,pp. S748-S758, vol. 5, Suppl 4.
Brumell et al., (2004) *Salmonella* redirects phagosomal maturation. Curr Opin Microbiol, 2004, pp. 78-84, vol. 7.
Cárdenas et al., Oral immunization using live attenuated *Salmonella* spp. as carriers of foreign antigens. Clin. Microbiol. Rev., 1992, pp. 328-342, vol. 5, No. 3.
Charnetzky et al., RNA synthesis in *Yersinia pestis* during growth restriction in calcium-deficient medium. J Bacteriol, 1982, pp. 108-195, vol. 149.
Chatfield et al., Use of the nirB promoter to direct the stable expression of heterologous antigens in *Salmonella* oral vaccine strains: development of a single-dose oral tetanus vaccine. Biotechnology (N Y), 1992, pp. 888-892, vol. 10, No. 8.
Cheng et al., Simultaneous analyses of neutral carbohydrates and amino sugars in freshwaters with HPLC-PAD. J. Chromatogr. Sci., 2003, pp. 434-438, vol. 41.
Chipman et al., The ACT domain family. Curr Opin Struct Biol, 2001, pp. 694-700, vol. 11.
Chromy et al., Proteomic characterization of *Yersinia pestis* virulence. J Bacteriol, 2005, pp. 8172-8180, vol. 187.
Coombes et al., SseL Is a *Salmonella*-Specific Translocated Effector Integrated into the SsrB-Controlled *Salmonella* Pathogenicity Island 2 Type III Secretion System. Infection and Immunity, 2007, pp. 574-580, vol. 75, No. 2.
Cornelis et al., The virulence plasmid of *Yersinia*, an antihost genome. Microbiol Mol Biol Rev, 1998, pp. 1315-1352, vol. 62.
Curtiss et al. Nonrecombinant and recombinant avirulent *Salmonella* vaccines for poultry. Vet Immunol Immunopathol, 1996, pp. 365-372, vol. 54.
Curtiss et al., Live oral avirulent *Salmonella* vaccines. Vet. Microbiol., 1993, pp. 397-405, vol. 37.
Curtiss et al., Recombinant *Salmonella* vectors in vaccine development. Dev Biol Stand., 1994, pp. 23-33, vol. 82.
Datsenko et al., One-step inactivation of chromosomal genes in *Escherichia coli* K-12 using PCR products. Proc Natl Acad Sci U S A, 2000, pp. 6640-6645, vol. 97.
Davison, Towards safer vectors for the field release of recombinant bacteria. Environ. Biosafety Res., 2002, pp. 9-18, vol. 1.
De Groote et al., Homocysteine antagonism of nitric oxide-related cytostasis in *Salmonella typhimurium*. Science, 1996, pp. 414-417, vol. 272.
Dekruyff et al., Induction of immunoglobulin synthesis by CD4+ T cell clones. Seminars in Immunology, 1993, pp. 421-430, vol. 5.
Del Beccaro et al., Bacteriology of acute otitis media: a new perspective. J Pediatr, 1992, pp. 81-84, vol. 120.
Deng et al., Genome sequence of *Yersinia pestis* KIM. J Bacteriol, 2002, pp. 4601-4611, vol. 184.
Doggett et al., Delivery of antigens by recombinant avirulent *Salmonella* strains. Adv. Exp. Med. Biol., 1992, pp. 165-173, vol. 327.
Doublet et al., The murl gene of *Escherichia coli* is an essential gene that encodes a glutamate racemase activity. J. Bacteriol., 1993, pp. 2970-2979, vol. 175.
Dubnau, DNA uptake in bacteria. Annu. Rev. Microbiol., 1999, pp. 217-244, vol. 53.
Edwards et al., Improved allelic exchange vectors and their use to analyze 987P fimbria nucleic acid sequence expression. Gene, 1998, pp. 149-157, vol. 207, No. 2.
Fooks, Development of oral vaccines for human use. Curr Opin Mol Ther, 2000, pp. 80-86, vol. 2, No. 1.
Foster et al., How *Salmonella* survive against the odds. Annu Rev Microbiol, 1995, pp. 145-174, vol. 49.
Galen et al., Can a 'flawless' live vector vaccine strain be engineered? Trends Microbiol, 2001, pp. 372-376, vol. 9, No. 8.
Garmory et al., The Use of Live Attenuated Bacteria as a Delivery System for Heterologous Antigens. Journal of Drug Targeting, 2003, pp. 471, vol. 11.
Garzon et al., recB recJ mutants of *Salmonella typhimurium* are deficient in transductional recombination, DNA repair and plasmid maintenance. Mol. Gen. Genet., 1996, pp. 570-580, vol. 250.
Gentry et al., Mutational analysis of the *Escherichia coli* spoT gene identifies distinct but overlapping regions involved in ppGpp synthesis and degradation. Mol Microbiol, 1996, pp. 1373-1384, vol. 19.
Gentschev et al., The *E. coli* alpha-hemolysin secretion system and its use in vaccine development. Trends Microbiol, 2002, pp. 39-45, vol. 10, No. 1.
Giannella et al., Gastric acidity and cholera. Ann Intern Med, 1973, p. 780, vol. 78.
Gilbert, The lac repressor and the lac operator. Ciba Found Symp, 1972, pp. 24-59, vol. 7.
Gong et al., Characterization of the *Yersinia pestis* Yfu ABC inorganic iron transport system. Infect Immun, 2001, pp. 2829-2837, vol. 69.
Gor et al., TH1-TH2: a Procrustean paradigm. Nat Immunol, 2003, p. 503-5, vol. 4.
Grillot-Courvalin et al., Functional gene transfer from intracellular bacteria to mammalian cells. Nat. Biotechnol., 1998, pp. 862-866, vol. 16.
Guerrant et al., Magnitude and Impact of Diarrheal Diseases. Arch. Med. Res., 2002, pp. 351-355, vol. 33.
Gunn, Mechanisms of bacterial resistance and response to bile. Microbes Infect, 2000, pp. 907-913, vol. 2.
Hengge-Aronis et al., Identification and molecular analysis of glgS, a novel growth-phase-regulated and rpoS-dependent gene involved in glycogen synthesis in *Escherichia coli*. Mol Microbiol, 1992, pp. 1877-1886, vol. 6.
Hanisch, et al, The Ralstonia eutropha H16 phasin PhaP1 is targeted to intracellular triacylglycerol inclusions in *Rhodococcus opacus* PD630 and *Mycobacterium smegmatis* mc2155, and provides an anchor to target other proteins.
Song et al., Organization and regulation of the D-xylose operons in *Escherichia coli* K-12: XyIR acts as a transcriptional activator. J Bacteriol, 1997, pp. 7025-7032, vol. 179.
Spellberg et al., Type 1/type 2 immunity in infectious diseases. Clin. Infect. Dis., 2001, pp. 76-102, vol. 32.
Schnaitman et al., Genetics of Lipopolysaccharide Biosynthesis in Enteric Bacteria. Microbiological Reviews, 1993, pp. 655-682, vol. 57, No. 3.
Srinivasan et al., Oral immunization with attenuated *Salmonella* expressing human sperm antigen induces antibodies in serum and the reproductive tract. Biol Reprod, 1995, pp. 462-471, vol. 53.
Steel et al., Live attenuated influenza viruses containing NS1 truncations as vaccine candidates against H5N1 highly pathogenic avian influenza. J. Virol., 2009, pp. 1742-1753, vol. 83.
Tacket et al., Safety and immunogenicity in humans of an attenuated *Salmonella typhi* vaccine vector strain expressing plasmid-encoded hepatitis B antigens stabilized by the asd-balanced lethal vector system. Infect Immun, 1997, pp. 3381-3385, vol. 65.

(56) References Cited

OTHER PUBLICATIONS

Taubenberger et al., 1918 Influenza: the mother of all pandemics. Emerg. Infect. Dis., 2006, pp. 15-22, vol. 12.
Török et al., Accumulation of ppGpp in a relA mutant of *Escherichia coli* during amino acid starvation. J. Biol. Chem., 1980, pp. 3838-3840, vol. 255.
Tu et al., The PhoP/PhoQ two-component system stabilizes the alternative sigma factor RpoS in *Salmonella enterica*. Proc Natl Acad Sci U S A., 2006, pp. 13503-13508, vol. 103.
Tumpey et al., Characterization of the reconstructed 1918 Spanish influenza pandemic virus. Science, 2005, pp. 77-80, vol. 310.
Van Rossum et al., Host and bacterial factors contributing to the clearance of colonization by *Streptococcus pneumoniae* in a murine model. Infect Immun, 2005, pp. 7718-7726, vol. 73.
Van Velkinburgh et al., PhoP-PhoQ-regulated loci are required for enhanced bile resistance in *Salmonella* spp. Infect Immun, 1999, pp. 1614-1622, vol. 67.
Webster et al., Evolution and ecology of influenza A viruses. Microbiol Rev, 1992, pp. 152-179, vol. 56.
Wilmes-Riesenberg et al., Role of acid tolerance response in virulence of *Salmonella typhimurium*. Infect.Immun, 1996, pp. 1085-1092, vol. 64.
Wu et al., The mechanism underlying T cell help for induction of an antigen-specific in vivo humoral immune response to intact *Streptococcus pneumoniae* is dependent on the type of antigen. J Immunol, 2002, pp. 5551-5557, vol. 168.
Zahn, Overexpression of an mRNA dependent on rare codons inhibits protein synthesis and cell growth. J Bacteriol, 1996, pp. 2926-2933, vol. 178, No. 10.
Zhang et al., Characterization and immunogenicity of *Salmonella typhimurium* SL1344 and UK-1 crp and cdt deletion mutants. Infect. Immun., 1997, pp. 5381-5387, vol. 65.
Zobel et al., RNA polymerase I catalysed transcription of insert viral cDNA. Nucleic. Acids. Res., 1993, pp. 3607-3614, vol. 21.
Baek et al., Leucine-Responsive Regulator Protein (Lrp) Acts as a Virulence Respressor in *Salmonella enterica* Servoar *typhimurium*. Journal of Bacteriology, 2009, pp. 1278-1292, vol. 191, No. 4.
PCT/US2011/061896—International Search Report and Written Opinion of the International Searching Authority, Apr. 5, 2012.
Byl et al, Sequence of the Genomore of Salmonella Bacteriophage P22. Journal of Bacteriology, 2000, pp. 6472-6484, vol. 182, 22.
Houng et al., Expression of Vi antigen in *Escherichia coli* K-12: characterization of ViaB from *Citrobacter freundii* and identity of ViaA with RcsB. J.Bacterio, 1992, pp. 5910-5915, vol. 174, No. 18.
Hori et al, Constructionof selt-disruptive *Bacillus megaterium* in response to substrate exhaustion for polyhydroxybutryrate production. Appl Microbiol Biotechnol, 2002, pp. 211-216, vol. 59.
Hurme et al, A Proteinaceous Gene Regulator Thermameter in *Salmonella*. Cell, 1997, pp. 55-64, vol. 90.
Kong et al., Salmonelle synthesizing 1-Monophosphorylated Lipopolysaccharide Exhibits Low Endotoxic while Retaining Its Immunogenicity. J Immunol, 2011, pp. 412-423, vol. 187.
Pickard et al., Characterization of defined ompR mutants of *Salmonella typhi*: ompR is involved in the regulation of Vi polysaccharide expression. Infect Immun, 1994, pp. 3984-3993, vol. 62, No. 9.
Reed et al., The W-Beijing Lineage of *Mycobacterium tuberculosis* Overproduces Triglycerides and Has the DosR Dormancy Regulon Constitutively Upregulated. Journal of Bacteriology, 2007, pp. 2583-2589, vol. 189, No. 7.
Takaya et al., The ATP-Dependent Lon Protease of *Salmonella enterica* Serovar *typhimurium* Regulates Invasion and Expression of Genes Carried on *Salmonella* Pathogenicity Island 1. Journal of Bacteriology, 2002, pp. 224-232, vol. 184, No. 1.
Waltman et al., Biochemical Characteristics of *Edwardsiella ictaluri*. Applied and Enviornmental Microbiology, 1986, pp. 101-104, vol. 51, No. 1.
Sun et al., Highly efficient method for introducing successive multiple scarless gene deletions and markerless gene insertions into the *Yersinia pestis* chromosome. Appl Environ Microbiol, 2008, pp. 4241-4245, vol. 74.
U.S. Appl. No. 13/006,072, Office Action dated Apr. 19, 2012.
Quenee, Lauriane E., et al., *Yersinia pestis* caf1 Variants and the Limits of Plague Vaccine Protection, Infection and Immunity, May 2008, vol. 76, No. 5, pp. 2025-2036.
U.S. Appl. No. 13/088,141, Office Action dated Dec. 6, 2012 (Ginny Portner).
U.S. Appl. No. 13/006,072, Office Action dated Dec. 11, 2012 (Ja'Na Hines).
Kong, W., T-10-, Improving DNA Vaccine Vector for Efficient Vaccine Delivery Using Live Attenuated Bacterial Carrier, The Society, vol. 2008, No. 108, pp. 668.
Mesika, Adi, et al., A Regulated, NF kB-Assisted Import of Plasmid DNA into Mammalian Cell Nuclei, Molecular Therapy, vol. 3, No. 5, May 2001, pp. 653-657.
Ribeiro, Sofia C., et al., The Role of Polyadenylation Signal Secondary Structures on the Resistance of Plasmid Vectors to Nucleases, The Journal of Gene Medicine, vol. 6, 2004, pp. 565-573.
Rytkonen, Anne, et al.,. SseL, a *Salmonella* Deubiquitinase Required for Macrophage Killing and Virulence, PNAS, vol. 104, No. 9, Feb. 27, 2007, pp. 3502-3507.
Wang, Shixia, et al., Hemagglutinin (HA) Proteins from H1 and H3 Serotypes of Influenza a Viruses Require Different Antigen Designs for the Induction of Optimal Protective Antibody Responses as Studied by Codon-Optimized HA DNA Vaccines, Journal of Virology, vol. 80, No. 23, Dec. 2006, pp. 11628-11637.
U.S. Appl. No. 13/302,575, Office Action dated Sep. 25, 2012 (Oluwatosin Ogunbiyi).
U.S. Appl. No. 12/615,872, Office Action dated Oct. 23, 2012 (Jennifer Graser).
American Society of Microbiology, vol. 108; 2008: (p. 668).
CDC, Update: influenza activity—United States, Sep. 30, 2007-Apr. 5, 2008, and composition of the 2008-09 influenza vaccine. MMWR Morb. Mortal. Wkly Rep., 2008, pp. 404-409, vol. 57.
Chen et al., Genetic mapping of the cold-adapted phenotype of B/Ann Arbor/1/66, the master donor virus for live attenuated influenza vaccines (FluMist). Virology, 2006, pp. 416-423, vol. 345.
Collins et al., Mutations at rfc or pmi attenuate *Salmonella typhimurium* virulence for mice. Infect. Immun., 1991, pp. 1079-1085, vol. 59.
Curtiss et al., Avirulent *Salmonella typhimurium* delta cya delta crp oral vaccine strains expressing a streptococcal colonization and virulence antigen. Vaccine, 1988, pp. 155-160, vol. 6.
Curtiss et al., New technologies in using recombinant attenuated *Salmonella* vaccine vectors. Crit. Rev. Immunol., 2010, pp. 255-270, vol. 30.
Curtiss et al., *Salmonella* strains with regulated delayed attenuation in vivo. Infect. Immun., 2009, pp. 1071-1082, vol. 77.
Curtiss et al., *Salmonella typhimurium* deletion mutants lacking adenylate cyclase and cyclic AMP receptor protein are avirulent and immunogenic. Infect Immun, 1987, pp. 3035-3043, vol. 55.
Curtiss et al., Stabilization of recombinant avirulent vaccine strains in vivo. Res Microbiol, 1990, pp. 797-805, vol. 141.
Curtiss, Bacterial infectious disease control by vaccine development. J. Clin. Investig., 2002, pp. 1061-1066, vol. 110.
Curtiss, Chromosomal aberrations associated with mutations to bacteriophage resistance in *Escherichia coli*. J. Bacteriol., 1965, pp. 28-40, vol. 89.
Daigle et al., Identification of *Salmonella typhi* genes expressed within macrophages by selective capture of transcribed sequences (SCOTS). Mol Microbiol, 2001, pp. 1211-1222, vol. 41.
Darzins. Nucleotide-sequence analysis of the phosphomannose isomerase gene (PMI) of *Pseudomonas aeruginosa* and comparison with the corresponding *Escherichia-coli* gene mana. Gene, 1986, pp. 293-302, vol. 42, No. 3.
Dean, 1997. Import of plasmid DNA into the nucleus is sequence specific. Exp. Cell Res., 1997, pp. 293-302, vol. 230.
Doggett et al., Immune responses to *Streptococcus sobrinus* surface protein antigen A expressed by recombinant *Salmonella typhimurium*. Infect Immun, 1993, pp. 1859-1866, vol. 61.
Dunstan et al., Comparison of the Abilities of Different Attenuated *Salmonella typhimurium* Strains to Elicit Humoral Immune Responses against a Heterologous Antigen. Infect. Immun., 1998, pp. 732-740, vol. 66.

(56) References Cited

OTHER PUBLICATIONS

Dusek et al., Brown, Systemic and mucosal immune responses in mice orally immunized with avirulent *Salmonella typhimurium* expressing a cloned *Porphyromonas gingivalis* hemagglutinin. Infect Immun, 1994, pp. 1652-1657, vol. 62, No. 5.
Egan et al., A regulatory cascade in the induction of rhaBAD. J Mol Biol, 1993, pp. 97-98, vol. 234.
Egorov et al., Transfectant influenza A viruses with long deletions in the NS1 protein grow efficiently in Vero cells. J. Virol., 1998, pp. 6437-6441, vol. 72.
Enami et al., Introduction of site-specific mutations into the genome of influenza virus. Proc. Natl. Acad. Sci. USA, 1990, pp. 3802-3805, vol. 87.
Fodor et al., Rescue of influenza A virus from recombinant DNA. J. Virol., 1999, pp. 9679-9682, vol. 73.
Formal et al., Construction of a potential bivalent vaccine strain: introduction of *Shigella sonnei* form I antigen genes into the galE *Salmonella typhi* Ty21a typhoid vaccine strain. Infect. Immun., 1981, pp. 746-750, vol. 34.
Fraser et al., The amino acid composition of T3 bacteriophage. J Biol Chem, 1953, pp. 291-295, vol. 205, No. 1.
Galan et al., Cloning and molecular characterization of genes whose products allow *Salmonella typhimurium* to penetrate tissue culture cells. Proc Natl Acad Sci U S A, 1989, pp. 6383-6387, vol. 86.
Galen et al., Optimization of Plasmid Maintenance in the Attenuated Live Vector Vaccine Strain *Salmonella typhi* CVD 908-htrA. Infect. Immun., 1999, pp. 6424-6433, vol. 67.
Garmory et al., Antibiotic-free plasmid stabilization by operator-repressor titration for vaccine delivery by using live *Salmonella enterica* serovar *typhimurium*. Infect. Immun., 2005, pp. 2005-2011, vol. 73.
Gay et al., Positive selection procedure for entrapment of insertion sequence elements in gram-negative bacteria. J Bacteriol, 1985, pp. 918-921, vol. 164, No. 2.
Gentschev et al., Delivery of the p67 sporozoite antigen of *Theileria parva* by using recombinant *Salmonella dublin*: secretion of the product enhances specific antibody responses in cattle. Infect. Immun., 1998, pp. 2060-2064, vol. 66.
Gerdil, The annual production cycle for influenza vaccine. Vaccine, 2003, pp. 1776-1779, vol. 21.
Ghany et al. Candidate live, attenuated *Salmonella enterica* serotype *typhimurium* vaccines with reduced fecal shedding are immunogenic and effective oral vaccines. Infect. Immun., 2007, pp. 1835-1842, vol. 75.
Greenwood, The epidemiology of pneumococcal infection in children in the developing world. Philos. Trans. R. Soc. Lond. B. Biol. Sci., 1999, pp. 777-785, vol. 354.
Gulig et al., Plasmid-associated virulence of *Salmonella typhimurium*. Infect Immun, 1987, pp. 2891-2901, vol. 55.
Guzman et al., Tight regulation, modulation, and high-level expression by vectors containing the arabinose PBAD promoter. J Bacteriol, 1995, pp. 4121-4130, vol. 177.
Hall et al., The role of fur in the acid tolerance response of *Salmonella typhimurium* is physiologically and genetically separable from its role in iron acquisition. J Bacteriol, 1996, pp. 5683-5691, vol. 178.
Hess et al., Superior efficacy of secreted over somatic antigen display in recombinant *Salmonella* vaccine induced protection against listeriosis. Proc. Natl. Acad. Sci. USA, 1996, pp. 1458-1463, vol. 93.
Hicks et al., Incidence of pneumococcal disease due to non-pneumococcal conjugate vaccine (PCV7) serotypes in the United States during the era of widespread PCV7 vaccination, 1998-2004. J Infect Dis, 2007, pp. 1346-1354, vol. 196.
Hitchcock et al., Morphological heteronucleic acid sequenceity among *Salmonella* lipopolysaccharide chemotypes in silver-stained polyacrylamide gels. J Bacteriol, 1983, pp. 269-277, vol. 154, No. 1.
Hoffmann et al., "Ambisense" approach for the generation of influenza A virus: vRNA and mRNA synthesis from one template. Virology, 2000, pp. 310-317, vol. 267.
Hohmann et al., Macrophage-inducible expression of a model antigen in *Salmonella typhimurium* enhances immunogenicity. Proc Natl Acad Sci U S A, 1995, pp. 2904-2908, vol. 92, No. 7.
Hollingshead et al., Diversity of PspA: mosaic genes and evidence for past recombination in *Streptococcus pneumoniae*. Infect Immun., 2000, pp. 5889-5900, vol. 68.
Hopkins et al., A recombinant *Salmonella typhimurium* vaccine induces local immunity by four different routes of immunization. Infect Immun, 1995, pp. 3279-3286, vol. 63.
Jin et al., Multiple amino acid residues confer temperature sensitivity to human influenza virus vaccine strains (FluMist) derived from cold-adapted A/Ann Arbor/6/60. Virology, 2003, pp. 18-24, vol. 306.
Kang et al., Immune responses dependent on antigen location in recombinant attenuated *Salmonella typhimurium* vaccines following oral immunization. FEMS Immunol. Med. Microbiol. Lett., 2003, pp. 99-104, vol. 37.
Kang et al., Immune responses to recombinant pneumococcal PspA antigen delivered by live attenuated *Salmonella enterica* serovar *typhimurium* vaccine. Infect. Immun., 2002, pp. 1739-1749, vol. 70.
Kang et al., Transduction-mediated transfer of unmarked deletion and point mutations through use of counterselectable suicide vectors. J Bacteriol, 2002, pp. 307-312, vol. 184.
Katzman et al., Invertebrate connective tissue. Isolation of D-arabinose from sponge acidic polysaccharide. Biochem J, 1970, pp. 17-19, vol. 119, No. 1.
Kennedy et al., Attenuation and immunogenicity of Delta cya Delta crp derivatives of *Salmonella choleraesuis* in pigs. Infection and Immunity, 1999, pp. 4628-4636, vol. 67, No. 9.
Kilbourne, Studies on influenza in the pandemic of 1957-1958. III. Isolation of influenza A (Asian strain) viruses from influenza patients with pulmonary complications; details of virus isolation and characterization of isolates, with quantitative comparison of isolation methods. J. Clin. Invest., 1959, pp. 266-274, vol. 38.
Klumpp et al., Roles of the influenza virus polymerase and nucleoprotein in forming a functional RNP structure. EMBO J., 1997, pp. 1248-1257, vol. 16.
Kong et al, Regulated programmed lysis of recombinant *Salmonella* in host tissues to release protective antigens and confer biological containment. PNAS, 2008, pp. 9361-9366, vol. 105, No. 27.
Konjufca et al., A Recombinant Attenuated *Salmonella enterica* Serovar *typhimurium* Vaccine Encoding *Eimeria acervulina* Antigen Offers Protection against *E. acervulina* Challenge. Infect. Immun., 2006, pp. 6785-96, vol. 74.
PCT/US2008/063303 (WO 2008/141226)—International Search Report and Written Opinion of the International Searching Authority, Nov. 26, 2008.
PCT/US2008/063293 (WO 2009/025888)—International Search Report and Written Opinion of the International Searching Authority, Feb. 12, 2009.
PCT/US2008/078991 (WO 2009/046449)—International Search Report and Written Opinion of the International Searching Authority, Dec. 15, 2008.
PCT/US2008/078993 (WO 2009/046451)—International Search Report and Written Opinion of the International Searching Authority, Dec. 15, 2008.
PCT/US2010/035630 (WO 2010/135563)—International Search Report and Written Opinion of the International Searching Authority, Sep. 29, 2010.
PCT/US2009/061100 (WO 2010/045620)—International Search Report and Written Opinion of the International Searching Authority, Dec. 4, 2009.
PCT/US2010/020137 (WO 2010/078584)—International Search Report and Written Opinion of the International Searching Authority, Mar. 9, 2010.
PCT/US2011/022110 (WO 2011/091291)—International Search Report and Written Opinion of the International Searching Authority, Apr. 11, 2011.
PCT/US2011/038588 (WO 2011/150421)—International Search Report and Written Opinion of the International Searching Authority, Nov. 22, 2011.
PCT/US98/24295—International Preliminary Examination Report, Dec. 26, 2000.

(56) References Cited

OTHER PUBLICATIONS

PCT/US2001/013915—International Preliminary Examination Report, Aug. 16, 2002.
European Patent Application No. 89910552.2 (EP0433372), Intention to Grant dated Jun. 19, 2001.
European Patent Application No. 89910552.2 (EP0433372), Office Action dated Oct. 10, 1994.
European Patent Application No. 89910552.2 (EP0433372), Office Action dated Sep. 12, 1995.
European Patent Application No. 89910552.2 (EP0433372), Office Action dated Jun. 20, 2000.
European Patent Application No. 89910552.2 (EP0433372), Decision to Grant dated May 6, 2002.
European Patent Application No. 90905859.6 (EP0465560), Office Action dated Feb. 19, 1992.
European Patent Application No. 90905859.6 (EP0465560), Office Action dated Feb. 9, 1994.
European Patent Application No. 90905859.6 (EP0465560), Intention to Grant dated Jan. 4, 1995.
European Patent Application No. 90905859.6 (EP0465560), Decision to Grant dated Apr. 25, 1996.
European Patent Application No. 96919292.1 (EP0832255), Office Action dated Sep. 30, 2003.
European Patent Application No. 96919292.1 (EP0832255), Office Action dated Jul. 13, 2004.
European Patent Application No. 96919292.1 (EP0832255), Intention to Grant dated May 25, 2005.
European Patent Application No. 96919292.1 (EP0832255), Decision to Grant dated Nov. 4, 2005.
European Patent Application No. 98958581.5 (EP1030690), Office Action dated Jan. 31, 2001.
European Patent Application No. 98958581.5 (EP1030690), Intention to Grant dated Sep. 7, 2001.
European Patent Application No. 98958581.5 (EP1030690), Decision to Grant dated May 24, 2002.
European Patent Application No. 01944119.5 (EP1292687), Office Action dated Oct. 18, 2004.
European Patent Application No. 01944119.5 (EP1292687), Office Action dated Aug. 4, 2005.
European Patent Application No. 01944119.5 (EP1292687), Intention to Grant dated Jan. 26, 2006.
European Patent Application No. 01944119.5 (EP1292687), Decision to Grant dated Jul. 20, 2006.
European Patent Application No. 01979646.5 (EP1326960), Intention to Grant dated Apr. 8, 2004.
European Patent Application No. 01979646.5 (EP1326960), Decision to Grant dated Oct. 28, 2004.
European Patent Application No. 03721711.4 (EP1499191), Search Report dated May 23, 2006.
European Patent Application No. 03721711.4 (EP1499191), Office Action dated Aug. 24, 2006.
European Patent Application No. 03721711.4 (EP1499191), Office action dated Jan. 17, 2007.
European Patent Application No. 03721711.4 (EP1499191), Office action dated Mar. 23, 2009.
European Patent Application No. 03721711.4 (EP1499191), Office action dated Jun. 15, 2010.
European Patent Application No. 03721711.4 (EP1499191), Intention to Grant dated Oct. 21, 2011.
European Patent Application No. 03770256.0 (EP1537214), Intention to Grant dated Aug. 12, 2005.
U.S. Appl. No. 08/473,789, Office Action dated Apr. 15, 1997.
U.S. Appl. No. 08/473,789, Office Action dated Dec. 23, 1997.
U.S. Appl. No. 08/473,789, Office Action dated Nov. 13, 1998.
U.S. Appl. No. 08/473,789, Office Action dated Jun. 14, 1999.
U.S. Appl. No. 08/473,789, Office Action dated Jan. 21, 2000.
U.S. Appl. No. 08/473,789, Office Action dated Jul. 25, 2000.
U.S. Appl. No. 08/473,789, Office Action dated Sep. 27, 2001.
U.S. Appl. No. 08/761,769, Office Action dated Jul. 20, 1998.
U.S. Appl. No. 08/761,769, Office Action dated Mar. 3, 1999.
U.S. Appl. No. 08/761,769, Office Action dated Aug. 9, 2000.
Hess et al., Secretion of different listeriolysin cognates by recombinant attenuated *Salmonella typhimurium*: superior efficacy of haemolytic over non-haemolytic constructs after oral vaccination. Microbes Infect, 2000, pp. 1799-1806, vol. 2.
Hohmann et al., Evaluation of a phoP/phoQ-deleted, aroA-deleted live oral *Salmonella typhi* vaccine strain in human volunteers. Vaccine, 1996, pp. 19-24, vol. 14.
Hu et al., The inducible lac operator-repressor system is functional in mammalian cells. Cell, 1987, pp. 555-566, vol. 48, No. 4.
Hu et al., The inducible lac operator-repressor system is functional for control of expression of injected DNA in *Xenopus* oocytes. Gene, 1988, pp. 301-313, vol. 62, No. 2.
Huang et al., Genome-wide screen of *Salmonella* nucleic acid sequences expressed during infection in pigs, using in vivo expression technology. Appl Environ Microbiol, 2007, pp. 7522-7530, vol. 73, No. 23.
Iannelli et al., Allelic variation in the highly polymorphic locus pspC of *Streptococcus pneumoniae*. Gene, 2002, pp. 63-71, vol. 284.
In Soo Lee et al., The stationary-phase sigma factor sS (RpoS) is required for a sustained acid tolerance response in virulent *Salmonella typhimurium*. Molecular Microbiology, 1995, pp. 155-167, vol. 17.
Isoda et al., Expression of a *Porphyromonas gingivalis* hemagglutinin on the surface of a *Salmonella* vaccine vector. Vaccine, 2007, pp. 117-126, vol. 25, No. 1.
Ivancic-Bace et al, Effects of recJ, recQ, and recFOR mutations on recombination in nuclease-deficient recB recD double mutants of *Escherichia coli*. J. Bacteriol., 2005, pp. 1350-1356, vol. 187.
Kaufmann et al., Impact of intracellular location of and antigen display by intracellular bacteria: implications for vaccine development. Immunol. Lett., 1999, pp. 81-84, vol. 65.
Khan et al., Immunogenicity and protective efficacy of DnaJ (hsp40) of *Streptococcus pneumoniae* against lethal infection in mice. Vaccine, 2006, pp. 6225-6231, vol. 24.
Kim et al., Direct transcriptional control of the plasminogen activator gene of *Yersinia pestis* by the cyclic AMP receptor protein. J Bacteriol, 2007, pp. 8890-8900, vol. 189.
Kolodrubetz et al., Regulation of the L-arabinose transport operons in *Escherichia coli*. J Mol Biol, 1981, pp. 215-227, vol. 151, No. 2.
Kwon et al., *Salmonella*-based vaccines for infectious diseases. Expert Review of Vaccines, 2007, pp. 147-152, vol. 6.
Lange et al., Identification of a central regulator of stationary-phase gene expression in *Escherichia coli*. Mol Microbiol, 1991, pp. 49-59, vol. 5.
Lee et al., Regulation of L-arabinose transport in *Salmonella typhimurium* LT2. Mol Gen Genet, 1982, pp. 136-141, vol. 185, No. 1.
Lee et al., Surface-displayed viral antigens on *Salmonella* carrier vaccine. Nat Biotechnol, 2000, pp. 645-648, vol. 18, No. 6.
Lewis, The lac repressor. C R Biol, 2005, pp. 521-548, vol. 328, No. 6.
Lobell et al., AraC-DNA looping: orientation and distance-dependent loop breaking by the cyclic AMP receptor protein. J Mol Biol, 1991, pp. 45-54, vol. 218.
Lobocka et al., Organization and expression of the *Escherichia coli* K-12 dad operon encoding the smaller subunit of D-amino acid dehydrogenase and the catabolic alanine racemase. J. Bacteriol., 1994, pp. 1500-1510, vol. 176.
Loessner et al., Bacteria-mediated DNA transfer in gene therapy and vaccination. Expert. Opin. Biol. Ther., 2004, pp. 157-168, vol. 4.
Loessner et al., Remote control of tumour-targeted *Salmonella enterica* serovar *typhimurium* by the use of L-arabinose as inducer of bacterial gene expression in vivo. Cell Microbiol, 2007, pp. 1529-1537, vol. 9.
Marshall et al., Use of the stationary phase inducible promoters, spv and dps, to drive heterologous antigen expression in *Salmonella* vaccine strains. Vaccine, 2000, pp. 1298-1306, vol. 18, No. 14.
Medina et al., Use of live bacterial vaccine vectors for antigen delivery: potential and limitations. Vaccine, 2001, pp. 1573-1580, vol. 19.
Mehigh et al., Expression of the low calcium response in *Yersinia pestis*. Microb Pathog, 1989, pp. 203-217, vol. 6.

(56) References Cited

OTHER PUBLICATIONS

Moore et al., Enhanced protective immunity against pneumococcal infection with PspA DNA and protein. Vaccine, 2006, p. 5755, vol. 24.
Mossing et al., Upstream operators enhance repression of the lac promoter. Science, 1986, pp. 889-892, vol. 233, No. 4766.
Motin et al., Passive immunity to *Yersiniae* mediated by anti-recombinant V antigen and protein A-V antigen fusion peptide. Infect Immun, 1994, pp. 4192-4201, vol. 62.
Muller et al., Repression of lac promoter as a function of distance, phase and quality of an auxiliary lac operator. J Mol Biol, 1996, pp. 21-29, vol. 257, No. 1.
Muller-Hill et al., Mutants that mke more lac repressor. Proc Natl Acad Sci U S A, 1968, pp. 1259-1264, vol. 59, No. 4.
Muller-Hill, Lac repressor and lac operator. Prog Biophys Mol Biol, 1975, pp. 227-252, vol. 30, No. 2-3.
Nabors et al., Immunization of healthy adults with a single recombinant pneumococcal surface protein A (PspA) variant stimulates broadly cross-reactive antibodies to heterologous PspA molecules. Vaccine, 2000, p. 1743, vol. 18.
Nakayama et al., Construction of an Asd+ expression-cloning vector: stable maintenance and high level expression of cloned nucleic acid sequences in a *Salmonella* vaccine strain. BioTechnology, 1988, pp. 693-697, vol. 6.
Nedialkov et al., Resistance to lipopolysaccharide mediated by the *Yersinia pestis* V antigen-polyhistidine fusion peptide: amplification of interleukin-10. Infect Immun, 1997, pp. 1196-1203, vol. 65.
Neutra et al., Antigen sampling across epithelial barriers and induction of mucosal immune responses. Annu Rev Immunol, 1996, pp. 275-300, vol. 14.
O'Callaghan et al., High efficiency transformation of *Salmonella typhimurium* and *Salmonella typhi* by electroporation. Mol Gen Genet, 1990, pp. 156-158, vol. 223, No. 1.
Ortqvist et al., Randomised trial of 23-valent pneumococcal capsular polysaccharide vaccine in prevention of pneumonia in middle-aged and elderly people. Swedish Pneumococcal Vaccination Study Group. Lancet, 1998, pp. 399-403, vol. 351.
Perry et al., Temperature regulation of the hemin storage (Hms+) phenotype of *Yersinia pestis* is posttranscriptional. J Bacteriol, 2004, pp. 1638-1647, vol. 186.
Petersen et al., Essential role for cyclic AMP and its receptor protein in *Yersinia enterocolitica* virulence. Infect Immun, 2004, pp. 3665-3672, vol. 70.
Ramarathinam et al., *Salmonella typhimurium* induces IFN-gamma production in murine splenocytes. Role of natural killer cells and macrophages. J Immunol, 1993, pp. 3973-3981, vol. 150.
Raupach et al., Bacterial virulence, proinflammatory cytokines and host immunity: how to choose the appropriate *Salmonella* vaccine strain? Microbes and Infection, 2001, p. 1261, vol. 3.
Roland et al., Construction and evaluation of a delta cya delta crp*Salmonella typhimurium* strain expressing avian pathogenic *Escherichia coli* O78 LPS as a vaccine to prevent airsacculitis in chickens. Avian Dis, 1999, pp. 429-441, vol. 43, No. 3.
Sarubbi et al., (1989) Characterization of the spoT gene of *Escherichia coli*. J Biol Chem, 1989, pp. 15074-15082, vol. 264.
Schmieger et al., Altered cotransduction frequencies exhibited by HT-mutants of *Salmonella*-phage P22. Mol Gen Genet, 1976, pp. 307-309, vol. 143.
Schmieger, Phage P22-mutants with increased or decreased transduction abilities. Mol Gen Genet, 1972, pp. 75-88, vol. 119.
Schödel et al., Hybrid hepatitis B virus core antigen as a vaccine carrier moiety. II. Expression in avirulent *Salmonella* spp. for mucosal immunization. Adv Exp Med Biol., 1996, pp. 15-21, vol. 397.
Schodel, Prospects for oral vaccination using recombinant bacteria expressing viral epitopes. Adv. Virus Res., 1992, pp. 409-446, vol. 41.
Schwyn et al., Universal chemical assay for the detection and determination of siderophores. Analytical Biochemistry, 1987, p. 47, vol. 160.
Sedgwick et al., A solid-phase immunoenzymatic technique for the enumeration of specific antibody-secreting cells. Journal of Immunological Methods, 1983, p. 301, vol. 57.
Shalaby, Development of oral vaccines to stimulate mucosal and systemic immunity: barriers and novel strategies. Clin Immunol Immunopathol, 1995, pp. 127-134, vol. 74, No. 2.
U.S. Appl. No. 08/761,769, Office Action dated Sep. 25, 2001.
U.S. Appl. No. 08/761,769, Office Action dated Aug. 8, 2002.
U.S. Appl. No. 08/761,769, Notice of Allowance and Fees Due dated Jan. 22, 2003.
U.S. Appl. No. 09/120,970, Office Action dated Sep. 6, 2000.
U.S. Appl. No. 09/120,970, Office Action dated Jun. 5, 2001.
U.S. Appl. No. 09/120,970, Office Action dated Jan. 12, 2005.
U.S. Appl. No. 09/120,970, Office Action dated Nov. 8, 2005.
U.S. Appl. No. 09/120,970, Notice of Allowance and Fees Due dated Aug. 6, 2010.
U.S. Appl. No. 09/560,539, Office Action dated Feb. 12, 2002.
U.S. Appl. No. 09/560,539, Office Action dated Mar. 25, 2003.
U.S. Appl. No. 09/560,539, Office Action dated Aug. 29, 2003.
U.S. Appl. No. 09/560,539, Notice of Allowance and Fees Due dated Mar. 30, 2004.
U.S. Appl. No. 09/686,499, Office Action dated Jun. 20, 2001.
U.S. Appl. No. 09/686,499, Office Action dated Jan. 29, 2002.
U.S. Appl. No. 09/686,499, Office Action dated Dec. 16, 2002.
U.S. Appl. No. 09/686,499, Office Action dated Aug. 27, 2003.
U.S. Appl. No. 09/686,499, Notice of Allowance and Fees Due dated Nov. 2, 2004.
U.S. Appl. No. 10/138,239, Office Action dated Mar. 15, 2005.
U.S. Appl. No. 10/138,239, Office Action dated Sep. 21, 2005.
U.S. Appl. No. 10/138,239, Notice of Allowance and Fees Due dated Mar. 16, 2006.
U.S. Appl. No. 10/414,533, Office Action dated Apr. 12, 2006.
U.S. Appl. No. 10/414,533, Notice of Allowance and Fees Due dated Dec. 8, 2006.
U.S. Appl. No. 10/511,616, Office Action dated Nov. 27, 2009.
U.S. Appl. No. 10/511,616, Office Action dated Jun. 23, 2010.
U.S. Appl. No. 10/511,616, Office Action dated Dec. 27, 2010.
U.S. Appl. No. 10/511,616, Notice of Allowance and Fees Due dated Oct. 26, 2011.
U.S. Appl. No. 10/620,777, Office Action dated Nov. 14, 2006.
U.S. Appl. No. 10/620,777, Office Action dated Oct. 31, 2007.
U.S. Appl. No. 10/924,574, Office Action dated Feb. 28, 2007.
U.S. Appl. No. 10/924,574, Notice of Allowance and Fees Due dated Oct. 1, 2007.
European Patent Application No. 08827622.5, Search Report dated Jun. 27, 2011.
European Patent Application No. 08827622.5, Office action dated Feb. 22, 2012.
U.S. Appl. No. 12/615,872, Office Action dated Mar. 14, 2012.
U.S. Appl. No. 12/681,711, Office Action dated Jan. 31, 2012.
U.S. Appl. No. 12/789,869, Office Action dated Mar. 22, 2011.
U.S. Appl. No. 12/789,869, Office Action dated Dec. 7, 2011.
Bang et al, OmpR regulates the stationary-phase acid tolerance response of *Salmonella enterica* serovar *typhimurium*. J Bacteriol, 2000, pp. 2245-2252, vol. 182.
Bang et al., Autoinduction of the ompR response regulator by acid shock and control of the *Salmonella enterica* acid tolerance response. Mol Microbiol, 2002, pp. 1235-1250, vol. 44.
Bartlett et al., Influenza A (H5N1): will it be the next pandemic influenza? Are we ready? Ann. Intern. Med., 2005, pp. 460-462, vol. 143.
Bartlett, Planning for avian influenza. Ann. Intern. Med., 2006, pp. 141-144, vol. 145.
Bearson et al., A low pH-inducible, PhoPQ-dependent acid tolerance response protects *Salmonella typhimurium* against inorganic acid stress. J Bacteriol, 1998, pp. 2409-2417, vol. 180.
Bertani, Studies on lysonucleic acid sequencesis. I. The mode of phage liberation by lysogenic *Escherichia coli*. J Bacteriol, 1951, pp. 293-300, vol. 62, No. 3.
Black et al., Aspartic •-semialdehydedehydrogenase and aspartic •-semialdehydel Biol. Chem., 1955, pp. 39-50, vol. 213.
Briles et al., Immunization of humans with recombinant pneumococcal surface protein A (rPspA) elicits antibodies that passively protect

(56) References Cited

OTHER PUBLICATIONS mice from fatal infection with *Streptococcus pneumoniae* bearing heterologous PspA. J. Infect. Dis., 2000, pp. 1694-1701, vol. 182.
Brooks-Walter et al., The pspC gene of *Streptococcus pneumoniae* encodes a polymorphic protein, PspC, which elicits cross-reactive antibodies to PspA and provides immunity to pneumococcal bacteremia. Infect. Immun., 1999, pp. 6533-6542, vol. 67.
Brosius et al., Spacing of the -10 and -35 regions in the tac promoter. Effect on its in vivo activity. J Biol Chem, 1985, pp. 3539-3540, vol. 260, No. 6.
Brown et al., MurA (MurZ), the enzyme that catalyzes the first committed step in peptidoglycan biosynthesis, is essential in *Escherichia coli*. J. Bacteriol., 1995, pp. 4194-4197, vol. 177.
Buchanan et al., IK-12 Enhances Antibody Responses to T-Independent Polysaccharide Vaccines in the Absence of T and NK Cells. J Immunol, 1998, pp. 5525-5533, vol. 161.
Buchmeier, et al., DNA repair is more important than catalase for *Salmonella* virulence in mice. J. Clin. Invest., 1995, pp. 1047-1053, vol. 95.
Bumann, Regulated antigen expression in live recombinant *Salmonella enterica* serovar *typhimurium* strongly affects colonization capabilities and specific CD4(+)-T-cell responses. Infect Immun, 2001. pp. 7493-7500, vol. 69, No. 12.
U.S. Appl. No. 12/759,842, Office Action dated Oct. 4, 2011.
Nieto et al., Complex Structure of the nuclear translocation signal of influenza virus polymerase PA subunit. Journal of General Nirology, 1994, pp. 29-36, vol. 75.
U.S. Appl. No. 12/599,655, Office Action dated Mar. 12, 2013.
U.S. Appl. No. 13/088,141, Office Action dated Apr. 24, 2014.
U.S. Appl. No. 12/681,711, Office Action dated Nov. 28, 2012.
U.S. Appl. No. 13/574,718, Office Action dated Sep. 6, 2013.
U.S. Appl. No. 13/574,718, Office Action dated Apr. 28, 2014.
U.S. Appl. No. 13/700,591, Office Action dated Apr. 2, 2014.
U.S. Appl. No. 13/898,241, Office Action dated Apr. 17, 2014.
Bittner et al., RpoS and RpoN are involved in the growth-dependent regulation of rtaH transcription and O antigen expression in *Salmonella enterica* serovar *typhi*, Microbial Pathogenisis. vol. 36, 2004 (p. 19).
Liu et al., Nickel-inducible lysis system in Synechocystis sp. PCC 6803. PNAS, vol. 106, 2009, pp. 21550-21554.
Liu et al., CO2-limitation-inducible Green Recovery of fatty acids from cyanobacterial biomass. PNAS, vol. 108, 2011 pp. 6905-6908.
Moreno et al., *Salmonella* as Live Trojan Horse for Vaccine Development and Cancer Gene Therapy. Current Gene Therapy, 2010, 10, pp. 56-76.
U.S. Appl. No. 13/302,575, Office Action dated Jun. 18, 2013.
Folkesson et al., Components of the peptidoglycan-recycling pathway modulate invasion and intracellular survival of *Salmonella enterica* serovar *typhimurium*. Cellular Microbiology, 2005, vol. 7(1) pp. 147-155.
Whitworth et al., Expression of the *Rickettsia prowazekii* pld or tlyC Gene in *Salmonella enterica* Serovar *typhimurium* Mediates Phagosomal Escape, Infection and Immunity, 2005, vol. 73(10), pp. 6668-6673.
Sheehan et al., Generation and characterization of hamster monoclonal antibodies that neutralize murine tumor necrosis factors. J Immunol, 1989, pp. 3884-3893, vol. 142.
Sizemore et al., Attenuated bacteria as a DNA delivery vehicle for DNA-mediated immunization. Vaccine, 1997, pp. 804-807, vol. 15.
Snapper et al., Distinct types of T-cell help for the induction of a humoral immune response to *Streptococcus pneumoniae*. Trends Immunol, 2001, pp. 308-311, vol. 22.
Sodeinde et al., Plasminogen activator/coagulase gene of *Yersinia pestis* is responsible for degradation of plasmid-encoded outer membrane proteins. Infect Immun, 1988, pp. 2749-2752, vol. 56.
Sternberg et al., Bacteriophage-mediated nucleic acid sequenceralized transduction in *Escherichia coli* and *Salmonella typhimurium*. Methods Enzymol, 1991, pp. 18-43, vol. 204.
Straley et al., Virulence genes regulated at the transcriptional level by Ca2+ in *Yersinia pestis* include structural genes for outer membrane proteins. Infect Immun, 1986, pp. 445-454, vol. 51.
Sun et al., The role of relA and spoT in *Yersinia pestis* KIM5+ pathogenicity. PLoS One, 2009, pp. E6720, vol. 4.
Thompson et al., The bacterial signal molecule, ppGpp, mediates the environmental regulation of both the invasion and intracellular virulence gene programs of *Salmonella*. J Biol Chem, 2006, pp. 30112-30121, vol. 281.
Une et al., In vivo comparison of avirulent Vwa- and Pgm- or Pstr phenotypes of *Yersiniae*. Infect Immun, 1984, pp. 895-900, vol. 43.
Uzzau et al., Epitope tagging of chromosomal genes in *Salmonella*. Proc Natl Acad Sci U S A, 2001, pp. 15264-15269, vol. 98.
Viboud et al., *Yersinia* outer proteins: role in modulation of host cell signaling responses and pathogenesis. Annu Rev Microbiol, 2005, pp. 69-89, vol. 59.
Wasserman et al., Two alanine racemase genes in *Salmonella typhimurium* that differ in structure and function. J. Bacteriol., 1983, pp. 1439-1450, vol. 153.
Whitfield, Biosynthesis and assembly of capsular polysaccharides in *Escherichia coli*. Annu Rev. Biochem., 2006, pp. 39-68, vol. 75.
Winter et al., The *Salmonella enterica* serotype *typhi* regulator TviA reduces interleukin-8 production in intestinal epithelial cells by repressing flagellin secretion. Cell Microbiol, 2008, pp. 247-261, vol. 10, No. 1.
Wolf et al., Evolution of aminoacyl tRNA synthetases—analysis of unique domain architectures and phylogenetic trees reveals a complex history of horizontal gene transfer events. Genome Res, 1999, pp. 689-710, vol. 9.
Xiao et al., Residual guanosine 39,59-bispyrophosphate synthetic activity of relA null mutants can be eliminated by spoT null mutations. J Biol Chem, 1991, pp. 5980-5990, vol. 266.
Zahorchak et al., Effect of exogenous nucleotides on Ca2+ dependence and V antigen synthesis in *Yersinia pestis*. Infect Immun, 1982, pp. 953-959, vol. 38.
Zhang et al., A "one-plasmid" system to generate influenza virus in cultured chicken cells for potential use in influenza vaccine. J. Virol., 2009, pp. 9296-9303, vol. 83.
Zhang et al., Transcription activation parameters at ara pBAD. J Mol Biol, 1996, pp. 14-24, vol. 258, No. 1.
Zinkernagel et al., Antigen localisation regulates immune responses in a dose- and time-dependent fashion: a geographical view of immune reactivity. Immunol Rev, 1997, pp. 199-209, vol. 156.
Briles et al., PspA, a protection-eliciting pneumococcal protein: immunogenicity of isolated native PspA in mice. Vaccine, 1996, pp. 858-867, vol. 14.
Hanisch, et al, The *Ralstonia eutropha* H16 phasin PhaP1 is targeted to intracellular triacylglycerol inclusions in *Rhodococcus opacus* PD630 and *Mycobacterium smegmatis* mc2155, and provides an anchor to target other proteins, Nov. 2006.
Kong et al, Regulated Delayed Expression of rfaH in an Attenuated *Salmonella enterica* Serovar *typhimurium* Vaccine Enhances Immunogenicity of Outer Membrane Proteins and Heterologous Antigen. Infec Immun. 2009, pp. 5572-5582, vol. 77, No. 12.
Lefman et al, Three-Dimensional Electron Microscopic Imaging of Membrane Invaginations in *Escherichia coli* Overproducing the Chemotaxis Receptor Tsr. Journal of Bacteriology, 2004, pp. 5052-5061, vol. 186, No. 15.
Morita et al., Antibacterial Activity of *Bacillus amyloliquefaciencs* Phage Endolysin without Holin Conjugation. Journal of Biosciences and Bioengineering, 2001, pp. 469-473, vol. 91, No. 5.
Navasa et al, Temperature has reciprocal effects on colanic acid and polysialic acid biosynthesis in *E. coli* K92. Appl Microbiol Biotechnol, 2009, pp. 721-729, vol. 82.
Stevens, Immunization with the C-Domain of alpha-Toxin Prevents Lethal Infection, Localizes Tissue Injury, and Promotes Host Responses to Challenge with *Clostridium perfringens*. JID, 2004, pp. 767-773, vol. 190.
U.S. Appl. No. 12/681,721, Office Action dated May 24, 2012.

(56) References Cited

OTHER PUBLICATIONS

U.S. Appl. No. 12/759,842, Office Action dated Jun. 7, 2012.
U.S. Appl. No. 12/599,655, Office Action dated Jul. 2, 2012.
R. Ellis, New Technologies for Making Vaccines. Vaccines, 1988, pp. 568-574, W.B. Saunders Company, Philadelphia.
Greenspan et al, Defining eptiopes: It's not as easy as it seems. Nature Biotechnology, 1999, pp. 936-937, vol. 17.
Houghten et al, Relative Importance of Position and Individual Amino Acid Residues in peptide Antigen-Antibody Interactions: Implications in the Mechanism of Antigenic Drift and Antigenic Shift. Vaccines86, 1986, Cold Spring Harbor Laboratory.

* cited by examiner

A

MTIKVGINGFGRIGRIVFRAAQERSDIEIVGINDLLDANYMAYMLKYDSTGRFNGTVEV
EEGHLIVNGKKIRVTAERDPANLKWNEIGVDVVAEATGLFLTDETARKHIAAGAKKVVM
TGPSKDATPMFVMGVNHKNYAGQAIVSNASCTTNCLAPLAKVLNDNFGIVEALMTTVHA
TTATQKTVDGPSMKDWRGGRGASQNIIPSSTGAAKAVGKVIELNGKLTGMAFRVPTPNV
SVVDLTARLAKPATYQQICEVMKAASEGEMKGVLGYTDEAVVSTDFNGEVCTSVFDADA
GISLNDNFVKLVSWYDNETGYSNKVLDLIAHISK*

B

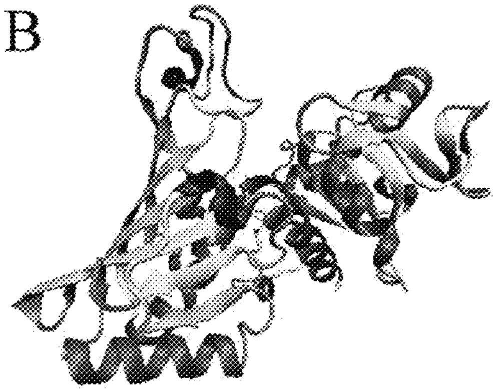

| *E. ictaluri* strains | Experiment #1 I.P Dose (CFU/ml) | Experiment #1 I.P Survivors/ Total | Experiment #2 Oral Dose (CFU/ml) | Experiment #2 Oral Survivors/ Total |
|---|---|---|---|---|
| J100 wild-type | $1.5x10^8$ | 0/6 | $1.2x10^8$ | 1/7 |
| | $1.5x10^6$ | 0/6 | $1.2x10^6$ | 2/7 |
| | $1.5x10^4$ | 1/6 | $1.2x10^4$ | 4/7 |
| J112 Δ*asdA01* | $3.0x10^8$ | 3/7* | $1.7x10^8$ | 7/8* |
| J112 Δ*asdA01* (pYA3493) | $2.1x10^8$ | 0/6 | $1.8x10^8$ | 3/7 |
| | $2.1x10^6$ | 2/6 | $1.8x0^6$ | 4/7 |
| | $2.1x10^4$ | 2/6 | $1.8x10^4$ | 5/7 |
| BSG (Control) | None | 6/6 | None | 6/6 |

B

| *E. ictaluri* strains | Experiment #1 I.M Dose (CFU/ml) | Experiment #1 I.M Survivors/ Total | Experiment #2 I.M Dose (CFU/ml) | Experiment #2 I.M Survivors/ Total |
|---|---|---|---|---|
| J100 wild-type | $1.5x10^8$ | 0/25 | $1.2x10^7$ | 0/25 |
| | $1.5x10^6$ | 0/25 | $1.2x10^5$ | 13/25 |
| | $1.5x10^4$ | 2/25 | $1.2x10^3$ | 22/25 |
| J112 Δ*asdA01* | $3.0x10^8$ | 0/10 | $1.7x10^7$ | 1/5 |
| | | | $1.7x10^5$ | 10/10 |
| | | | $1.7x10^3$ | 10/10 |
| J112 Δ*asdA01* (pYA3493) | $2.1x10^8$ | 0/10 | $1.8x10^8$ | 0/5 |
| | $2.1x10^6$ | 0/10 | $1.8x0^6$ | 0/5 |
| | $2.1x10^4$ | 10/10 | $1.8x10^4$ | 5/5 |
| BSG (Control) | None | 10/10 | None | 5/5 |

FIG. 13

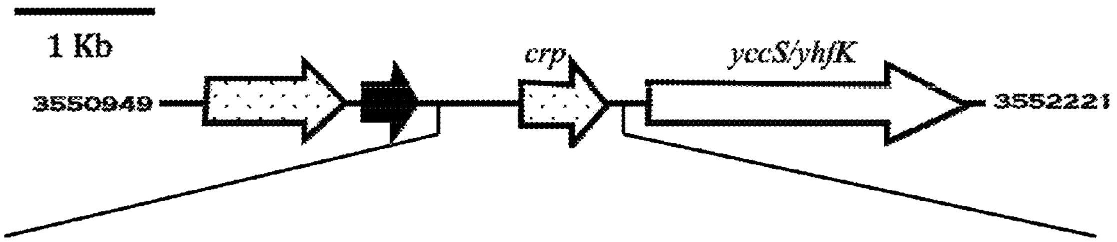

TTGCATGAAAGCGTCAATATTATGCCGCGTAGCCAGTTTAATGGCGTTGATTAGCGCACGTTGGCGTATTT
TCCCGTGCTGCGTCTGGCGCCGCGCTGTGCAAATAAAAATCAAAAGCACCACGGGGGAGAAAAAACGGTGG
CGAACAGTGAGCTATTCCATGCTGAAGCGAGACAGTGCGAGACAGTAAGGCCAAGCTATGCTACAAACTAA
GCCGATATGCACCTTTAATGGAATGGAGCGGGTATAGATCAAGATCGCCGGGGATCATCTCCCTTAGGCTA
TGGAAACTATATTCGACAAGTGCAGTGCTATAGCAGGTTACTAGGCAGTTCCCGGCCCCGTCCAGCGGGGA
-35 -10
TGCGTTTGGCGCACCGGGGATGCGATAACAACAGAGGATAATAGCGAATGGTTCTCGGCAAACCGCAAACA

GATCCAACTCTCGAATGGTTCCTGTCTCATTGCCATATTCACAAATATCCGTCCAAAAGTACCTTGATTCA
CCAAGGTGAAAAAGCGGAGACGCTTTATTACATCGTAAAGGGATCTGTAGCGGTACTGATTAAGGATGAAG
AGGGTAAGGAGATGATTCTCTCCTACCTGAACCAGGGCGACTTCATTGGCGAGCTGGGGTTGTTTGAGGAA
GGGCAGGAGCGTAGTGCCTGGGTGCGGGCGAAGACTGCCTGTGAGGTGGCTGAAATTTCCTACAAGAAATT
CCGCCAGCTGATCCAGGTTAACCCAGATATTTTGATGCGTCTGTCTTCCCAGATGGCGCGTCGTCTGCAGG
TCACGTCAGAGAAAGTCGGTAACCTGGCCTTCCTGGATGTGACAGGCCGTATTGCTCAGACGCTGTTGAAT
CTGGCCAAGCAGCCAGATGCGATGACGCACCCAGACGGCATGCAGATTAAAATCACCCGTCAGGAGATCGG
CCAGATTGTGGGTTGCTCTCGTGAAACGGTAGGACGTATCCTGAAGATGCTGGAGGATCAGAACCTGATCT
CGGCACACGGTAAAACCATCGTCGTCTACGGGACGCGTTGATTTTGCGCCCGCGCCGCACGAGCGGCGCGG
AATCTTCAACCCATCCCCAGGATGGTGCTCATGTGGCGGCGCTTTATCTACCACCCTGAAGTGAACTATGC
CCTGCGCCAGACGCTGGTTTTGTGTCTGCCGGTGCTGTTCGGGCTGATGGTAGGCCAGCTGCAGCAGGGGC
TGCTGTTTTCTCTGGTACCGGTCTGCTGTAATATCGCCGGTCTTGACACCCCCCATAAACGCTTCTTTAAA

FIG. 14

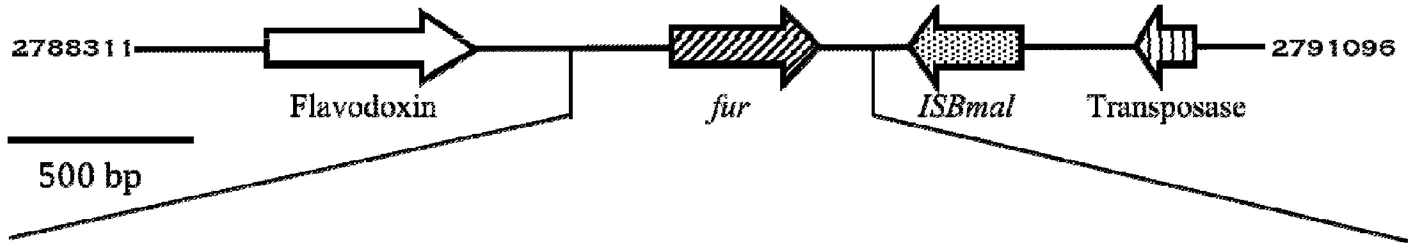

TGTCTGCCGCCTGCCGGCGCGGGACACCGTTTAATAGCCGGCAGGTATTTCAACCATCAATAAAAACGATAATGCGCAG

TTCGCTGCGTCATTTGTTTCTATCTTCCTCATTACTCGTGGGTTATATCAAGCCCGCGCCGCAGGCACCCCGTTCCGGGC

-35 -10

ACACCGCGCCACGGTTCCCATTTAGAGATATCGGCCTTATAATGAATCTCACTATTATTTTCCGTTCGGTAACGGCCCTTG

GGCGCTGCCGGGCGCTGTGACAGGACAGAATCCGAATGACCGACAACAACACCGCGTTAAAGAAAGCTGGCCTTAAAGT

SD

CACGCTTCCCCGTCTCAAGATTCTGGAAGTACTGCAAGATCCTACGTGCCATCATGTCAGTGCTGAAGACTTGTACAAGAA

GCTAATCGATATGGGCGAGGAGATCGGTCTGGCGACTGTATACCGCGTACTCAACCAGTTTGACGATGCCGGCATCGTGAC

CCGCCATAACTTTGAGGGCGGTAAATCGGTTTTTGAGCTGACCCAGCAGCACCACCACGATCACCTGATCTGCCTGGACTGC

GGCAAGGTCATCGAATTCAGCGATGAGTCCATTGAGAAGCGTCAGCGCGAAATCGCGAAAAAGCACGGCATCCAGCTGAC

CAACCACAGCCTGTATCTCTACGGCCACTGCGCCGAAGGCGACTGCCGTAGCGATGAGACCCTGCACGATGAAAAGGCCT

GAGTGACCTGGCGCCCACAGCAGGCGACGACGCGGCCCAGCGGGGCCGTTTTTTTCCCTGCGCGACAGCGGGCAAAAAA

AAGGTTCATCGCGCTTTACCGGGGAACGCTGCTTTTATCTTCAG

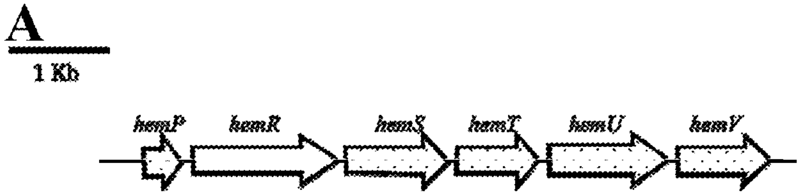

B

| Protein | Hypothetical function | BLAST (ID%:Positives%) | pI | Mass (Da) |
|---|---|---|---|---|
| **HemP** | Hemin uptake | *E. tarda* (86:94)<br>*P. stuartii* (68:76) | 10.29 | 8345.85 |
| **HemR** | TonB dependent Hemin receptor | *E. tarda* (94:97)<br>*Y. mollaretii* (61:75) | 6.13 | 72904.86 |
| **HemS** | Hemin degradation/storage | *E. tarda* (92:93)<br>*Y. pestis* (62:76) | 6.19 | 38018.77 |
| **HemT** | Periplasmatic hemin-binding protein | *E. tarda* (91:94)<br>*Y. pestis* (62:77) | 9.56 | 28631.10 |
| **HemU** | Hemin ABC transporter, permease | *E. tarda* (91:94)<br>*Y. pestis* (62:77) | 9.40 | 35576.78 |
| **HemV** | Hemin ABC transporter, ATPase | *E. tarda* (96:96)<br>*Y. intermedia* (67:77) | 9.26 | 28914.41 |

FIG. 23

RECOMBINANT *EDWARDSIELLA* BACTERIUM

CROSS REFERENCE TO RELATED APPLICATIONS

This application claims the priority of U.S. provisional application No. 61/182,569, filed May 29, 2009, which is hereby incorporated by reference in its entirety.

GOVERNMENTAL RIGHTS

This invention was made with government support under contract number 2009-65119-05703 awarded by the USDA. The government has certain rights in the invention.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821 (f).

FIELD OF THE INVENTION

The invention encompasses a recombinant *Edwardsiella* bacterium, and compositions and methods of use thereof.

BACKGROUND OF THE INVENTION

Economic loss due to infectious diseases in the global aquaculture industry is estimated to be $3 billion annually. The aquaculture industry has the fastest growth rate of all animal producing food sectors; its contribution to the global food supply by weight has increased from 3.9% in 1970 to 32.4% in 2004, with a value of $70.3 billion. As the capture fishing industry has declined and wild stocks diminished, the aquaculture industry became an important source of food. Commercial catfish production accounts for 85 to 90% of the total finfish aquaculture production in the United States, with almost 300,000 tons produced annually. The most serious bacterial pathogens affecting this industry are *Edwardsellia ictaluri* and *Flavobacterium columnare*. Loss due to these bacterial pathogens is estimated to be $50-80 million, annually. In all kinds of intensive culture, where single or multiple species are reared in high density, infectious disease agents are easily transmitted between individuals. In those intensive systems, vaccination is one of the most important enhancers of production yields.

Currently, the most common method for vaccination in the aquaculture industry is intraperitoneal (i.p.) injection. This class of immunization is expensive due to labor intensity and added costs for anesthesia, gas, needles, electricity, etc. Furthermore, i.p. vaccination is cost prohibitive for booster immunizations. Consequently, injectable vaccines are not used in catfish aquaculture. Instead, live attenuated bacterial vaccines administered in a bath are commercially used. Live recombinant attenuated vaccines, which can protect against several diseases at low cost and are biologically contained, have not previously been designed for the aquaculture industry.

SUMMARY OF THE INVENTION

One aspect of the present invention encompasses a recombinant attenuated *Edwardsiella* bacterium, wherein the bacterium is antibiotic sensitive.

Another aspect of the present invention encompasses a vaccine. The vaccine typically comprises a recombinant attenuated *Edwardsiella* bacterium, wherein the bacterium is antibiotic sensitive.

Yet another aspect of the present invention encompasses a method of eliciting an immune response in a host. The method comprises administering a recombinant attenuated *Edwardsiella* bacterium, wherein the bacterium is antibiotic sensitive.

Other aspects and iterations of the invention are described more thoroughly below.

REFERENCE TO COLOR FIGURES

The application file contains at least one photograph executed in color. Copies of this patent application publication with color photographs will be provided by the Office upon request and payment of the necessary fee.

BRIEF DESCRIPTION OF THE FIGURES

FIG. 7 depicts an illustration of (A) the amino acid sequence of *E. ictaluri* DAPDH (SEQ ID NO:1) and (B) the virtual 3D structure.

FIG. 13 depicts an illustration of (A) Survival of catfish (*I. punctatus*) infected with *E. ictaluri* wild type and *E. ictaluri* ΔasdA01 with and without $Asd^+$ vectors. The catfish were infected i.p with 100 μl and orally with 20 μl; (B) Survival of zebrafish (*D. rerio*) infected with wild type and *E. ictaluri* ΔasdA01 with and without $Asd^+$ vectors. The Zebrafish were infected I.M with 10 μl. * death within 48 h FIG. 14 depicts an illustration of *E. ictaluri* crp gene (SEQ ID NO:6). The unnamed arrows indicate unknown gene functions. In bold is the gene sequence of *E. ictaluri* crp gene. The predicted −10 region and −35 region of the crp promoter are indicated.

FIG. 19 depicts an illustration of *E. ictaluri* fur gene (SEQ ID NO:7). The unnamed arrows indicate unknown gene functions. In bold is the gene sequence of the *E. ictaluri* fur gene. The predicted −10 region and −35 region of the fur promoter are indicated.

FIG. 23 depicts an illustration of deletion of (A) *E. ictaluri* hemin receptor gene cluster and (B) predicted function of each protein.

DETAILED DESCRIPTION OF THE INVENTION

Figure 1:
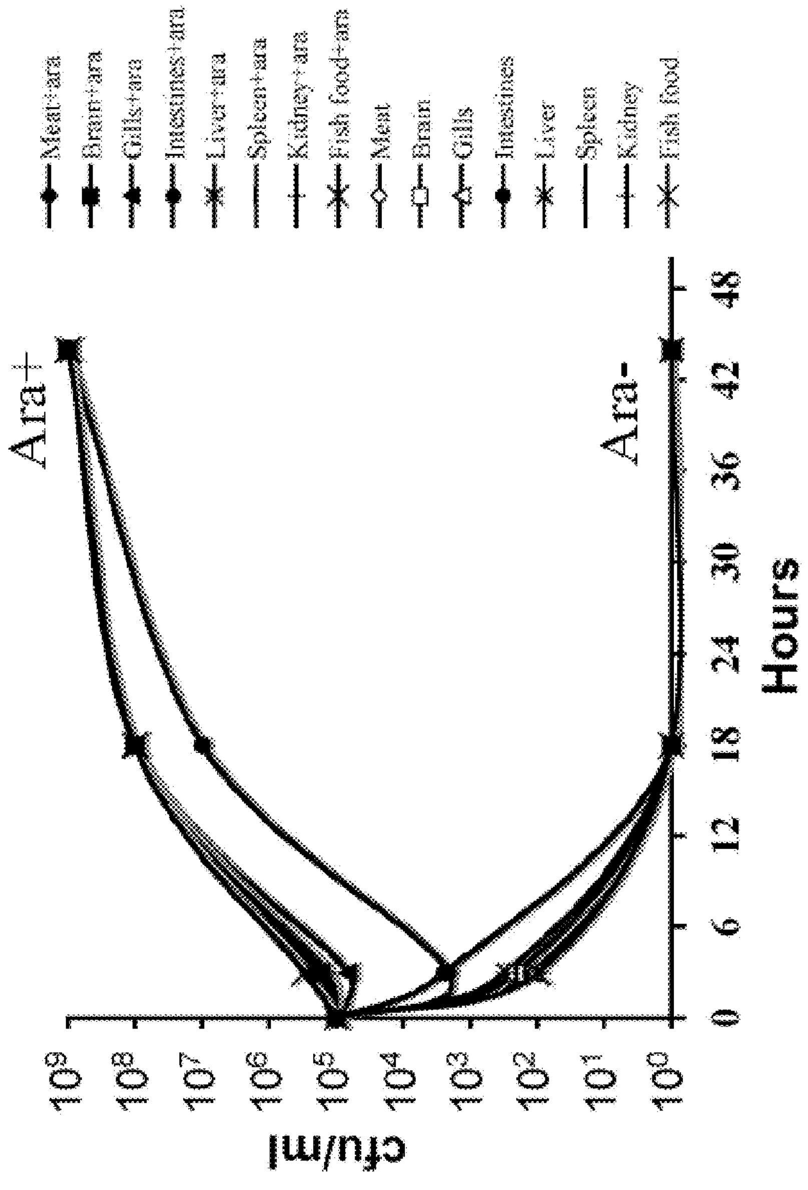
FIG. 1 depicts a graph illustrating arabinose levels in catfish tissues. The arabinose-dependent conditionally lethal *S. Typhimurium* strain $\chi$9442 ($\Delta P_{murA12}$::TT araC $P_{BAD}$ murA) was used to detect the presence of arabinose in catfish that would support growth and prevent lysis. Filter sterilized Nutrient broth (media devoid of arabinose), supplemented with 1% of fish tissue was inoculated with $10^5$ CFU of $\chi$9442 in presence and absence of L-arabinose (0.05% wt/vol). Nutrient broth non-supplemented with fish tissues was used as control. At 36 h no viable bacteria were detected in the absence of arabinose.

The present invention provides a recombinant *Edwardsiella* bacterium. The bacterium may be used to induce an immune response from a host, typically a fish. In particular, the bacterium may be used to induce an immune response to more than one pathogen. For instance, the bacterium may be used to induce an immune response to one or more of the pathogens *E. ictaluri, F. columnare*, and *E. tarda*. Advantageously, the bacterium may be capable of regulated lysis to facilitate biocontainment.

I. Recombinant *Edwardsiella* Bacterium

One aspect of the present invention is a recombinant *Edwardsiella* bacterium. Typically, the bacterium is derived from an *E. ictaluri* strain. For instance, the bacterium may be derived from *E. ictaluri* strain J100. Alternatively, a bacterium of the invention may be a strain listed in Table A below.

TABLE A

| Strains | Characteristics |
|---|---|
| *Escherichia coli* | |
| χ6097 | $F^-$ araD139 Δ(proAB-lac) $1^-$ f80dlacZΔM15 rpsL ΔasdA4 Δ(zhf-2 :: Tn10) thi-1 |
| χ6212 | $F^-$ Δ(argF-lacZYA)-U169 glnV44 $1^-$ deoR f80dlacZΔM15 gyrA96 recA1 relA1 endA1 ΔasdA4 Δ(zhf-2::Tn10) thi-1 hsdR17 |
| χ7213 | thr-1 leuB6 fhuA21 lacY1 glnV44 recA1 DasdA4 D(zhf-2::Tn10) thi-1 RP4-2-Tc::Mu [λpir]; $Km^r$ |
| χ7232 | endA1 hsdR17 (rK−, mk+) supE44 thi-1 recA1 gyrA relA1 Δ(lacZYAargF) U169 λ pir deoR (ϕ80dlacΔ(lacZ)M15) |
| χ7370 | $F^-$ araD139 Δ(ara-leu)-7697 ΔlacX74 Δlon-4 galK deoR ΔcsgA4::cat mcrA galU f80dlacZΔM15 ΔfliC38 Δ(wcaL-wza)-19 recA1 endA1 nupG rpsL ΔfimA-H Δ(mcrBC-hsdRMS-mrr) |
| χ7592 | Top10 F− mcrA Δ(mrr-hsdRMS-mcrBC) 80lacZDM15 ΔlacX74 recA1 araD139 Δ(ara-leu)7697 galU galK rpsL ($Str^R$) endA1 nupG |
| BL21 DE3 | $F^-$ ompT $hsdS_B$ ($r_B$ -$m_B$ -) gal dcm (DE3) |
| BL21 DE3 LysS+ | $F^-$ ompT $hsdS_B$ ($r_B$ -$m_B$ -) gal dcm (DE3) pLysS |
| *Edwardsiella ictaluri* | |
| J100 | 2003/C strain; isolated from Channel catfish, (*Ictalurus punctatus*); infect Zebrafish (*Danio rerio*) and Channel catfish; $pEI1^+$; $pEI2^+$ API20E 40040057 100% *Ed. ictaluri* ; smooth LPS; $Col^r$ $H_2$ $O_2^+$ $Fim^-$ |
| J101 | Isolated from Zebrafish (*Danio rerio*); $pEI1^+$; $pEI2^+$ API20E 40040057 100% Ed. ictaluri; smooth LPS; $Col^r$ $H_2$ $O_2^+$ $Fim^-$ |
| J102 | Isolated from Channel catfish, *Ictalurus punctatus* ; $pEI1^+$; $pEI2^+$ API20E 40040057 100% *Ed. ictaluri* ; smooth LPS; $Col^r$ $H_2$ $O_2^+$ $Fim^-$ |
| J103 | Isolated from Channel catfish, *Ictalurus punctatus* Alabama; $pEI1^+$; $pEI2^+$ AP20E 40040057 100% Ed. ictaluri; smooth LPS; $Col^r$ |
| J104 | Isolated from Channel catfish, *Ictalurus punctatus* Georgia; $pEI1^+$; $pEI2^+$ API20E 40040057 100% Ed. ictaluri; smooth LPS; $Col^r$ $H_2$ $O_2^+$ $Fim^-$ |
| J105 | Isolated from Channel catfish, *Ictalurus punctatus* Maryland; $pEI1^+$; $pEI2^+$ API20E 40040057 100% *Ed. ictaluri* ; smooth LPS; $Col^r$ $H_2$ $O_2^+$ $Fim^-$ |
| J106 | Isolated from Channel catfish, *Ictalurus punctatus* Mississippi; $pEI1^+$; $pEI2^+$ API20E 40040057 100% Ed. ictaluri; smooth LPS; $Col^r$ $H_2$ $O_2^+$ $Fim^-$ |
| J107 | Isolated from kidney of Channel catfish (*Ictalurus punctatus*); $pEI1^+$; $pEI2^+$; API20E 40040057 100% *E. ictaluri* ; smooth LPS; $Col^r$ $H_2$ $O_2^+$ $Fim^-$ |
| J108 | Isolated from head of Channel catfish (*Ictalurus punctatus*); pEI1+; pEI2+; API20E 40040057 100% *E. ictaluri* ; smooth LPS; Colr $H2O2^+$ $Fim^-$ |
| J109 | Isolated from kidney of Channel catfish (*Ictalurus punctatus*); $pEI1^+$; $pEI2^+$; API20E 40040057 100% *E. ictaluri* ; smooth LPS; $Col^r$ $H_2$ $O_2^+$$Fim^-$ |
| J110 | Isolated from Channel catfish (*Ictalurus punctatus*); $pEI1^+$; $pEI2^+$; API20E 40040057 100% *E. ictaluri* ; smooth LPS; $Col^r$ $H_2$ $O_2^+$ $Fim^-$ |
| J111 | ΔasdA01 J102 2003/c derivative, *Ictalurus punctatus* ; $pEI1^+$; $pEI2^+$ AP20E 40040057 100% *E. ictaluri* ; smooth LPS; $Dap^-$; $Col^r$ $H_2$ $O_2^+$ $Fim^-$; Constructed by conjugation pEZ102 |
| J112 | ΔasdA01 J101 2003/c derivative, *Ictalurus punctatus* ; $pEI1^+$; $pEI2^+$ AP20E 40040057 100% *E. ictaluri* ; smooth LPS; $Dap^-$; $Col^r$ $H_2$ $O_2^+$ $Fim^-$: Constructed by conjugation pEZ102 |
| J113 | Δcrp-10 J101 2003/c derivative, *Ictalurus punctatus* ; $pEI1^+$; $pEI2^+$ AP20E 40040057 100% *E. ictaluri* ; smooth LPS; $Col^r$ $H_2$ $O_2^+$ $Fim^-$: Constructed by conjugation pEZ104 |
| J114 | ΔgalE20 J101 2003/c derivative, *Ictalurus punctatus* ; $pEI1^+$; $pEI2^+$ AP20E 40040057 100% *E. ictaluri* ; smooth LPS Gal independent; $Gal^-$; $Col^r$ $H_2$ $O_2^+$ $Fim^-$: Constructed by conjugation pEZ105 |
| J120 | Δgne-30 J100 2003/c derivative; $pEI1^+$; $pEI2^+$ AP20E 40040057 100% *E. ictaluri* ; rough LPS Gal independent; $Gal^+$; $Col^r$ $H_2$ $O_2^+$ $Fim^-$: Autoagglutination Constructed by conjugation pEZ108 |
| J121 | Δgne-30 ΔasdA01 J120; $pEI1^+$; $pEI2^+$ AP20E 40040057 100% *E. ictaluri* ; rough LPS Gal independent; $Gal^+$; $Col^r$ $H_2$ $O_2^+$ $Fim^-$; $DAP^-$; Constructed by conjugation pEZ102 |
| J122 | ΔgalE20 Δgne-30 J114 derivative; $pEI1^+$; $pEI2^+$ AP20E 40040057 100% *E. ictaluri* ; rough LPS Gal independent; $Gal^-$; $Col^r$ $H_2$ $O_2^+$ $Fim^-$: Constructed by conjugation |
| J123 | ΔgalF91 J100 2003/c derivative; $pEI1^+$; $pEI2^+$ AP20E 40040057 100% *E. ictaluri* ; smooth LPS Gal independent; $Gal^+$; $Col^r$ $H_2$ $O_2^+$ $Fim^-$: Constructed by conjugation pEZ110 |

TABLE A-continued

| Strains | Characteristics |
|---|---|
| J124 | ΔwibT90 J100 2003/c derivative; pEI1$^+$; pEI2$^+$ AP20E 40040057 100% *E. ictaluri* ; rough LPS Gal independent; Gal$^+$; Col$^r$ $H_2$ $O_2^+$ Fim$^-$: Constructed by conjugation pEZ111 |
| J125 | ΔesrB70100 J100 2003/c derivative; pEI1$^+$; pEI2$^+$ AP20E 40040057 100% *E. ictaluri* ; smooth LPS Gal independent; Gal$^+$; Col$^r$ $H_2$ $O_2^+$ Fim$^-$: Constructed by conjugation pEZ109 |
| J126 | Δgne-31 J100 2003/c derivative; pEI1$^+$; pEI2$^+$ AP20E 40040057 100% *E. ictaluri* ; rough LPS Gal independent; Gal$^+$; Col$^r$ $H_2$ $O_2^+$ Fim$^-$: Constructed by conjugation pEZ112 |
| J128 | ΔwibT90 ΔgalE20 J124 2003/c derivative; pEI1$^+$; pEI2$^+$ AP20E 40040057 100% *E. ictaluri* ; rough LPS Gal independent; Gal$^-$; Col$^r$ $H_2$ $O_2^+$ Fim$^-$: Constructed by conjugation pEZ105 |
| J129 | Δcrp-10 ΔasdA01 J113 2003/c derivative; pEI1$^+$; pEI2$^+$ AP20E 40040057 100% *E. ictaluri* ; smooth LPS; Dap$^-$; Col$^r$ $H_2$ $O_2^+$ Fim$^-$: Constructed by conjugation pEZ102 |
| J130 | ΔesrB70 ΔasdA01 J125 2003/c derivative; pEI1$^+$; pEI2$^+$ AP20E 40040057 100% *E. ictaluri* ; smooth LPS Gal independent; Gal$^+$; Col$^r$ $H_2$ $O_2^+$ Fim$^-$: DAP-Constructed by conjugation pEZ102 |
| J132 | Δfur-35n frame deletion of fur, leaving the stop codon. J100 2003/c derivative; pEI1$^+$; pEI2$^+$ AP20E 40040057 100% *E. ictaluri* ; smooth LPS Gal independent; Gal$^+$; Col$^r$ $H_2$ $O_2^+$ Fim$^-$: Constructed by conjugation pEZ123; IROMPs up-regulated independent of Fe concentration in the media |
| J133 | Δpmi-10 J100 2003/c derivative; pEI1$^+$; pEI2$^+$ AP20E 40040057 100% *E. ictaluri* ; smooth LPS Mann independent; Man$^-$; Gal$^+$; Col$^r$ ; $H_2$ $O_2^+$ Fim$^-$; Constructed by conjugation pEZ122 |
| J135 | Δugd-11 J100 2003/c derivative; pEI1$^+$; pEI2$^+$ AP20E 40040057 100% *E. ictaluri* ; rough LPS Gal independent; Gal$^+$; Col$^s$ $H_2$ $O_2^+$ Fim$^-$; Constructed by conjugation pEZ124 |
| *Edwardsiella tarda* | |
| J115 | Wild type Ed. tarda ATCC 15947, isolated from human; serotype O1483: H1, Col$^r$ |
| J116 | Wild type *Ed. tarda* EIH202, highly virulent, fish isolated, Col$^r$ , Cm$^r$ , Tef$^r$ |
| J117 | Wild type *Ed tarda* PPD 130/90, highly virulent, fish isolated, Col$^r$ |
| *Flavobacterium columnare* | |
| J201 | *Flavobacterium columnare* , Wild-type strain from Dr. Kennett Craig, Iowa University |
| Plasmids | |
| pYA232 | pSC101 ori lacI$^q$ , 10.2 kb, Tc$^R$ |
| pYA3332 | p15A ori Aad$^+$, 3425 bp |
| pYA3337 | pSC101 ori Asd$^+$, 4343 bp |
| pYA3341 | pUC ori Asd$^+$, 2771 bp |
| pYA3342 | pBR ori Asd$^+$, 3012 bp |
| pYA3493 | pBR ori bla SS, Asd$^+$, 3113 bp |
| pYA3620 | pBR ori bla SS bla CT, Asd$^+$, 3169 bp |
| pYA4111 | pBR ori Asd+ GST gene fusion vector, 3.7 kb |
| pYA3700 | pUC ori TTaraCPBAD Ampr |
| pYA3784 | oriV ΔrelA198::araCPBAD::lacITT Cmr pR112 derivate |
| pYA4138 | oriV ΔasdA27::TT araC PBAD c2 Cmr pR112 derivate |
| pYA3832 | oriV ΔPcrp527::TT araC PBAD crp Cmr pR112 derivate |
| pYA4179 | oriV ΔPfur33::TT araC PBAD fur Cmr |
| pR112 | oriV Suicide vector Cm¶ |
| pMEG-375 | R6K ori Suicide vector Ampr Cmr |
| pCR2.1-TOPO | pUC ori ApR, KanR PCR cloning vector, 3931 bp |
| pET23a(+) | pBR ori PT7 N-terminal T7 tag/C-terminal His-tag, ApR, 3663 bp |
| pET28a(+) | pBR ori PT7 lacO N-terminal His-tag/thrombin/T7-tag/C-terminal His-tag, KanR, 5368 bp |
| pET30a(+) | pBR ori PT7 lacO N-terminal His-tag/thrombin/S-tag/C-terminal His-tag, KanR, 5422 bp |
| pGEX4T-2 | pBR ori GST gene fusion vector ApR, 4970 bp |
| pEZ101 | Cmr; pR112 derivative; contains the flanking regions to delete asd |
| pEZ102 | Cmr, Apr; pMEG-375 derivative; contains the flanking regions to delete asd |
| pEZ104 | Cmr, Apr; pMEG-375 derivative; contains the flanking regions to delete crp |
| pEZ105 | Cmr, Apr; pMEG-375 derivative; contains the flanking regions to delete galE |
| pEZ109 | Cm$^r$ , Ap$^r$ ; pMEG-375 derivative; contains the flanking regions to delete esrB |
| pEZ110 | Cm$^r$ , Ap$^r$ ; pMEG-375 derivative; contains the flanking regions to delete galF |
| pEZ111 | Cm$^r$ , Ap$^r$ ; pMEG-375 derivative; contains the flanking regions to delete wibT |
| pEZ112 | Cm$^r$ , Ap$^r$ ; pMEG-375 derivative; contains the flanking regions to delete gne |

TABLE A-continued

| Strains | Characteristics |
|---|---|
| pEZ115 | His6-HA-GAPDH; gapA gene from *E. ictaluri* clone into pET30a |
| pEZ116 | His6-HA-GAPDH; gapA gene from *E. tarda clone* into pET30a |
| pEZ117 | His6-HA-GAPDH; gapA gene from *V. anguillarum* clone into pET30a |
| pEZ118 | His6-HA-GAPDH; gapA gene from *Flavobacterium* clone into pET30a |
| pEZ121 | $Cm^r$, $Ap^r$; pMEG-375 derivative; contains the flanking regions to delete rpoS |
| pEZ122 | $Cm^r$, $Ap^r$; pMEG-375 derivative; contains the flanking regions to delete pmi |
| pEZ123 | $Cm^r$, $Ap^r$; pMEG-375 derivative; contains the flanking regions to delete fur |
| pEZ124 | $Cm^r$, $Ap^r$; pMEG-375 derivative; contains the flanking regions to delete ugd |
| pEZ141 | 1003 bp of *Flavobacterium* gapA gene cloned into pYA3498 |
| pEZ145 | $Cm^r$, $Ap^r$; pMEG-375 derivative; contains the flanking regions to insert $\Delta P_{murA10}$::TT araC$P_{BAD}$ murA |
| pEZ148 | $Cm^r$, $Ap^r$; pMEG-375 derivative; contains the flanking regions to delete phoP |

Usually, a bacterium of the invention is antibiotic sensitive. The phrase "antibiotic sensitive," as used herein, means that the bacterium has not been genetically manipulated to enhance antibiotic resistance. In certain embodiments, the bacterium may be sensitive to ampicillin, kanamycin, and/or rifampicin.

Generally speaking, a bacterium of the invention may be attenuated. Methods of attenuating a bacterium are detailed in section I(b) below. Additionally, the bacterium may be capable of the regulated expression of a nucleic acid encoding an antigen, and/or capable of regulated lysis. In an exemplary embodiment, a bacterium of the invention may be attenuated, may be capable of the regulated expression of a nucleic acid encoding an antigen, and may be capable of regulated lysis. Each is described in more detail below.

In certain embodiments, a bacterium of the invention may elicit an immune response against *Edwardsiella* in a host. In other embodiments, a bacterium of the invention may elicit an immune response against a fish pathogen other than *Edwardsiella* in a host.

In an exemplary embodiment, a bacterium of the invention may comprise one or more mutations selected from the group comprising Δcrp-10; ΔwibT-10; Δfur-35; ΔasdA01; Δugd-11; ΔgalE20; Δpmi-10; $\Delta P_{crp11}$::TT araC $P_{BAD}$ crp; $\Delta P_{fur70}$::TT araC $P_{BAD}$ fur; $\Delta P_{insA40}$::TT araC $P_{BAD}$ insA or Δgne-31; ΔesrB70; ΔrelA50::araC $P_{BAD}$ lacI TT; ΔasdA02::TT araC $P_{BAD}$ c2; and $\Delta P_{murA60}$::TT araC $P_{BAD}$ murA.

(a) Regulated Expression of a Nucleic Acid Encoding an Antigen

The present invention encompasses a recombinant bacterium capable of regulated expression of at least one nucleic acid sequence encoding an antigen of interest. Generally speaking, the bacterium comprises a chromosomally integrated nucleic acid sequence encoding a repressor and a vector. Each is discussed in more detail below. In some embodiments, the bacterium comprises a ΔrelA::araC $P_{BAD}$ lacI TT mutation, such as $\Delta_{relA50}$::araC $P_{BAD}$ lacI TT, or a ΔasdA::TT araC $P_{BAD}$ c2 mutation, such as ΔasdA02::TT araC $P_{BAD}$ c2, or a combination thereof.

i. Chromosomally Integrated Nucleic Acid Sequence Encoding a Repressor

A recombinant bacterium of the invention that is capable of the regulated expression of at least one nucleic acid sequence encoding an antigen comprises, in part, at least one chromosomally integrated nucleic acid sequence encoding a repressor. Typically, the nucleic acid sequence encoding a repressor is operably linked to a regulatable promoter. The nucleic acid sequence encoding a repressor and/or the promoter may be modified from the wild-type nucleic acid sequence so as to optimize the expression level of the nucleic acid sequence encoding the repressor.

Methods of chromosomally integrating a nucleic acid sequence encoding a repressor operably-linked to a regulatable promoter are known in the art and detailed in the examples. Generally speaking, the nucleic acid sequence encoding a repressor should not be integrated into a locus that disrupts colonization of the host by the recombinant bacterium, or attenuates the bacterium. In one embodiment, the nucleic acid sequence encoding a repressor may be integrated into the relA nucleic acid sequence. Alternatively, a nucleic acid sequence encoding a repressor may be integrated into a locus comprising a nucleic acid sequence that was previously removed (e.g. knocked out) from the bacterium's genome.

In some embodiments, at least one nucleic acid sequence encoding a repressor is chromosomally integrated. In other embodiments, at least two, or at least three nucleic acid sequences encoding repressors may be chromosomally integrated into the recombinant bacterium. If there is more than one nucleic acid sequence encoding a repressor, each nucleic acid sequence encoding a repressor may be operably linked to a regulatable promoter, such that each promoter is regulated by the same compound or condition. Alternatively, each nucleic acid sequence encoding a repressor may be operably linked to a regulatable promoter, each of which is regulated by a different compound or condition.

A. Repressor

As used herein, "repressor" refers to a biomolecule that represses transcription from one or more promoters. Generally speaking, a suitable repressor of the invention is synthesized in high enough quantities during the in vitro growth of the bacterial strain to repress the transcription of the nucleic acid encoding an antigen of interest on the vector, as detailed below, and not impede the in vitro growth of the strain. Additionally, a suitable repressor will generally be substantially stable, i.e. not subject to proteolytic breakdown. Furthermore, a suitable repressor will be diluted by about half at every cell division after expression of the repressor ceases, such as in a non-permissive environment (e.g. an animal or human host).

The choice of a repressor depends, in part, on the species of the recombinant bacterium used. For instance, the repressor is usually not derived from the same species of bacteria as the recombinant bacterium. For instance, the repressor may be derived from *E. coli* if the recombinant bacterium is from the genus *Edwardsiella*. Alternatively, the repressor may be from a bacteriophage.

Suitable repressors are known in the art, and may include, for instance, LacI of *E. coli*, C2 encoded by bacteriophage P22, or C1 encoded by bacteriophage λ. Other suitable repressors may be repressors known to regulate the expression of a regulatable nucleic acid sequence, such as nucleic acid sequences involved in the uptake and utilization of sugars. In one embodiment, the repressor is LacI.

B. Regulatable Promoter

The chromosomally integrated nucleic acid sequence encoding a repressor is operably linked to a regulatable promoter. The term "promoter", as used herein, may mean a synthetic or naturally-derived molecule that is capable of conferring, activating or enhancing expression of a nucleic acid. A promoter may comprise one or more specific transcriptional regulatory sequences to further enhance expression and/or to alter the spatial expression and/or temporal expression of a nucleic acid. The term "operably linked," as used herein, means that expression of a nucleic acid is under the control of a promoter with which it is spatially connected. A promoter may be positioned 5' (upstream) of the nucleic acid under its control. The distance between the promoter and a nucleic acid to be expressed may be approximately the same as the distance between that promoter and the native nucleic acid sequence it controls. As is known in the art, variation in this distance may be accommodated without loss of promoter function.

The regulated promoter used herein generally allows transcription of the nucleic acid sequence encoding a repressor while in a permissive environment (i.e. in vitro growth), but ceases transcription of the nucleic acid sequence encoding a repressor while in a non-permissive environment (i.e. during growth of the bacterium in an animal or human host). For instance, the promoter may be sensitive to a physical or chemical difference between the permissive and non-permissive environment. Suitable examples of such regulatable promoters are known in the art.

In some embodiments, the promoter may be responsive to the level of arabinose in the environment. Generally speaking, arabinose may be present during the in vitro growth of a bacterium, while typically absent from host tissue. In one embodiment, the promoter is derived from an araC-$P_{BAD}$ system. The araC-$P_{BAD}$ system is a tightly regulated expression system that has been shown to work as a strong promoter induced by the addition of low levels of arabinose. The araC-araBAD promoter is a bidirectional promoter controlling expression of the araBAD nucleic acid sequences in one direction, and the araC nucleic acid sequence in the other direction. For convenience, the portion of the araC-araBAD promoter that mediates expression of the araBAD nucleic acid sequences, and which is controlled by the araC nucleic acid sequence product, is referred to herein as $P_{BAD}$. For use as described herein, a cassette with the araC nucleic acid sequence and the araC-araBAD promoter may be used. This cassette is referred to herein as araC-$P_{BAD}$. The AraC protein is both a positive and negative regulator of $P_{BAD}$. In the presence of arabinose, the AraC protein is a positive regulatory element that allows expression from $P_{BAD}$. In the absence of arabinose, the AraC protein represses expression from $P_{BAD}$. This can lead to a 1,200-fold difference in the level of expression from $P_{BAD}$.

Other enteric bacteria contain arabinose regulatory systems homologous to the araC-araBAD system from *E. coli*. For example, there is homology at the amino acid sequence level between the *E. coli* and the *S. Typhimurium* AraC proteins, and less homology at the DNA level. However, there is high specificity in the activity of the AraC proteins. For example, the *E. coli* AraC protein activates only *E. coli* $P_{BAD}$ (in the presence of arabinose) and not *S. Typhimurium* $P_{BAD}$. Thus, an arabinose regulated promoter may be used in a recombinant bacterium that possesses a similar arabinose operon, without substantial interference between the two, if the promoter and the operon are derived from two different species of bacteria.

Generally speaking, the concentration of arabinose necessary to induce expression is typically less than about 2%. In some embodiments, the concentration is less than about 1.5%, 1%, 0.5%, 0.2%, 0.1%, or 0.05%. In other embodiments, the concentration is 0.05% or below, e.g. about 0.04%, 0.03%, 0.02%, or 0.01%. In an exemplary embodiment, the concentration is about 0.05%.

In some embodiments, a regulatable promoter may be sensitive to rhamnose or xylose. For instance, a rhamnose or xylose regulatory system from *E. coli* may be used. In both cases the regulatable promoter allows transcription in the presence of the sugar and ceases transcription in the absence of the sugar.

The nucleic acid sequences of the promoters detailed herein are known in the art, and methods of operably-linking them to a chromosomally integrated nucleic acid sequence encoding a repressor are known in the art and detailed in the examples.

C. Modification to Optimize Expression

A nucleic acid sequence encoding a repressor and regulatable promoter detailed above, for use in the present invention, may be modified so as to optimize the expression level of the nucleic acid sequence encoding the repressor. The optimal level of expression of the nucleic acid sequence encoding the repressor may be estimated, or may be determined by experimentation (see the Examples). Such a determination should take into consideration whether the repressor acts as a monomer, dimer, trimer, tetramer, or higher multiple, and should also take into consideration the copy number of the vector encoding the antigen of interest, as detailed below. In an exemplary embodiment, the level of expression is optimized so that the repressor is synthesized while in the permissive environment (i.e. in vitro growth) at a level that substantially inhibits the expression of the nucleic acid encoding an antigen of interest, and is substantially not synthesized in a non-permissive environment, thereby allowing expression of the nucleic acid encoding an antigen of interest.

As stated above, the level of expression may be optimized by modifying the nucleic acid sequence encoding the repressor and/or promoter. As used herein, "modify" refers to an alteration of the nucleic acid sequence of the repressor and/or promoter that results in a change in the level of transcription of the nucleic acid sequence encoding the repressor, or that results in a change in the level of synthesis of the repressor. For instance, in one embodiment, modify may refer to altering the start codon of the nucleic acid sequence encoding the repressor. Generally speaking, a GTG or TTG start codon, as opposed to an ATG start codon, may decrease translation efficiency ten-fold. In another embodiment, modify may refer to altering the Shine-Dalgarno (SD) sequence of the nucleic acid sequence encoding the repressor. The SD sequence is a ribosomal binding site generally located 6-7 nucleotides upstream of the start codon. The SD consensus sequence is AGGAGG, and variations of the consensus sequence may alter translation efficiency. In yet another embodiment, modify may refer to altering the distance between the SD sequence and the start codon. In still another embodiment, modify may refer to altering the −35 sequence for RNA polymerase recognition. In a similar embodiment, modify may refer to altering the −10 sequence for RNA polymerase binding. In an additional embodiment, modify may refer to altering the number of nucleotides between the −35 and −10 sequences. In an alternative embodiment, modify may refer to optimizing the codons of the nucleic acid sequence encoding the repressor to alter the level of translation of the mRNA encoding the repressor. For instance, non-A rich codons initially after the start codon of the nucleic acid sequence encoding the repressor may not maximize translation of the mRNA encoding the repressor. Similarly, the codons of the nucleic acid sequence encoding the repressor may be altered so as to mimic the codons from highly synthesized proteins of a particular organism. In a further embodiment, modify may refer to altering the GC content of the nucleic acid sequence encoding the repressor to change the level of translation of the mRNA encoding the repressor.

In some embodiments, more than one modification or type of modification may be performed to optimize the expression level of the nucleic acid sequence encoding the repressor. For instance, at least one, two, three, four, five, six, seven, eight, or nine modifications, or types of modifications, may be performed to optimize the expression level of the nucleic acid sequence encoding the repressor.

By way of non-limiting example, when the repressor is LacI, then the nucleic acid sequence of LacI and the promoter may be altered so as to increase the level of LacI synthesis. In one embodiment, the start codon of the LacI repressor may be altered from GTG to ATG. In another embodiment, the SD sequence may be altered from AGGG to AGGA. In yet another embodiment, the codons of lacI may be optimized according to the codon usage for *Edwardsiella*. In a further embodiment, the start codon of lacI may be altered, the SD sequence may be altered, and the codons of lacI may be optimized.

Methods of modifying the nucleic acid sequence encoding the repressor and/or the regulatable promoter are known in the art and detailed in the examples.

D. Transcription Termination Sequence

In some embodiments, the chromosomally integrated nucleic acid sequence encoding the repressor further comprises a transcription termination sequence. A transcription termination sequence may be included to prevent inappropriate expression of nucleic acid sequences adjacent to the chromosomally integrated nucleic acid sequence encoding the repressor and regulatable promoter.

ii. Vector for the Regulated Expression of a Nucleic Acid Encoding an Antigen

A recombinant bacterium of the invention that is capable of the regulated expression of at least one nucleic acid sequence encoding an antigen comprises, in part, a vector. The vector comprises a nucleic acid sequence encoding at least one antigen of interest operably linked to a promoter. The promoter is regulated by the chromosomally encoded repressor, such that the expression of the nucleic acid sequence encoding an antigen is repressed during in vitro growth of the bacterium, but the bacterium is capable of high level synthesis of the antigen in an animal or human host. The vector may be a part of a balanced-lethal or balanced-attenuation host vector system As used herein, "vector" refers to an autonomously replicating nucleic acid unit. The present invention can be practiced with any known type of vector, including viral, cosmid, phasmid, and plasmid vectors. The most preferred type of vector is a plasmid vector.

As is well known in the art, plasmids and other vectors may possess a wide array of promoters, multiple cloning sequences, transcription terminators, etc., and vectors may be selected so as to control the level of expression of the nucleic acid sequence encoding an antigen by controlling the relative copy number of the vector. In some instances in which the vector might encode a surface localized adhesin as the antigen, or an antigen capable of stimulating T-cell immunity, it may be preferable to use a vector with a low copy number such as at least two, three, four, five, six, seven, eight, nine, or ten copies per bacterial cell. A non-limiting example of a low copy number vector may be a vector comprising the pSC101 ori.

In other cases, an intermediate copy number vector might be optimal for inducing desired immune responses. For instance, an intermediate copy number vector may have at least 10, 11, 12, 13, 14, 15, 16, 17, 18, 19, 20, 21, 22, 23, 24, 25, 26, 27, 28, 29, or 30 copies per bacterial cell. A non-limiting example of an intermediate copy number vector may be a vector comprising the p15A ori.

In still other cases, a high copy number vector might be optimal for the induction of maximal antibody responses. A high copy number vector may have at least 31, 35, 40, 45, 50, 55, 60, 65, 70, 75, 80, 85, 90, 95, or 100 copies per bacterial cell. In some embodiments, a high copy number vector may have at least 100, 125, 150, 175, 200, 225, 250, 275, 300, 325, 350, 375, or 400 copies per bacterial cell. Non-limiting examples of high copy number vectors may include a vector comprising the pBR ori or the pUC ori.

Additionally, vector copy number may be increased by selecting for mutations that increase plasmid copy number. These mutations may occur in the bacterial chromosome but are more likely to occur in the plasmid vector.

Preferably, vectors used herein do not comprise antibiotic resistance markers to select for maintenance of the vector.

A. Antigen

As used herein, "antigen" refers to a biomolecule capable of eliciting an immune response in a host. In some embodiments, an antigen may be a protein, or fragment of a protein, or a nucleic acid. In an exemplary embodiment, the antigen elicits a protective immune response. As used herein, "protective" means that the immune response contributes to the lessening of any symptoms associated with infection of a host with the pathogen the antigen was derived from or designed to elicit a response against. For example, a protective antigen from a pathogen, such as *Mycobacterium*, may induce an immune response that helps to ameliorate symptoms associated with *Mycobacterium* infection or reduce the morbidity and mortality associated with infection with the pathogen. The use of the term "protective" in this invention does not necessarily require that the host is completely protected from the effects of the pathogen.

Antigens may be from bacterial, viral, fungal, protozoan, and parasitic pathogens of fish, and may be designed to protect against bacterial, viral, fungal, protozoan, and parasitic infections of fish, respectively. It is contemplated that antigens from organisms newly identified or newly associated with a disease or pathogenic condition, or new or emerging pathogens of animals or humans, including those now known or identified in the future, may be expressed by a bacterium detailed herein. Furthermore, antigens for use in the invention are not limited to those from pathogenic organisms. The selection and recombinant synthesis of antigens has been previously described by Schodel (Schödel F et al., Adv Exp Med Biol. 1996; 397:15-21) and Curtiss (Curtiss, R. III. Mucosal Immunology, 3rd ed., p. 1009-1037 (2005) Elsevier Academic Press.). Immunogenicity of the bacterium may be augmented and/or modulated by constructing strains that also express sequences for cytokines, adjuvants, and other immunomodulators.

Some examples of microorganisms useful as a source for antigen are listed below. These may include *E. ictaluri*, *E. tarda*, *Flavobacterium columnare*, *Renibacterium salmoni-*

*narum, Yersinia ruckeri, Vibrio* species such as *V. acquilarium, Aeromonas* species, including *A. hydrophila, A. sobria, A. caviae, A. schuberti, A. veronii* and *A. salmonicida*, certain *Nocardia* species, certain *Pasteurella* species, certain *Photobacterium* species, certain *Tenacibaculum* species, certain *Flexibacter* species, certain *Cytophaga* species, certain *Francisella* species, certain *Mycobacterium* species, certain *Streptococcus* species (*S. iniae*), and certain *Lactococcus* species. Fish viral pathogens, such as Infectious Salmon Anaemia Virus (ISAV) and Infectious Pancreatic Necrosis Virus (IPNV) may also serve as useful sources of antigen. Antigens may also be derived from pathogenic fungi, protozoa and parasites.

It is not necessary that the vector comprise the complete nucleic acid sequence of the antigen. It is only necessary that the antigen sequence used be capable of eliciting an immune response. The antigen may be one that was not found in that exact form in the parent organism. For example, a sequence coding for an antigen comprising 100 amino acid residues may be transferred in part into a recombinant bacterium so that a peptide comprising only 75, 65, 55, 45, 35, 25, 15, or even 10, amino acid residues is produced by the recombinant bacterium. Alternatively, if the amino acid sequence of a particular antigen or fragment thereof is known, it may be possible to chemically synthesize the nucleic acid fragment or analog thereof by means of automated nucleic acid sequence synthesizers, PCR, or the like and introduce said nucleic acid sequence into the appropriate copy number vector.

In another alternative, a vector may comprise a long sequence of nucleic acid encoding several nucleic acid sequence products, one or all of which may be antigenic. In some embodiments, a vector of the invention may comprise a nucleic acid sequence encoding at least one antigen, at least two antigens, at least three antigens, or more than three antigens. These antigens may be encoded by two or more open reading frames operably linked to be expressed coordinately as an operon, wherein each antigen is synthesized independently. Alternatively, the two or more antigens may be encoded by a single open reading frame such that the antigens are synthesized as a fusion protein.

In further embodiments, a nucleic acid sequence encoding an antigen of the invention may comprise a secretion signal. In other embodiments, an antigen of the invention may be toxic to the recombinant bacterium.

Additionally, the vectors may be designed for various types of antigen delivery systems. The system that is selected will depend, in part, on the immune response desired. For example, if an antibody response is desired, then a Type II secretion system may be used. Examples of Type II secretion systems are well-known in the art. Alternatively, if a cytotoxic T lymphocyte (CTL) response is desired, then a Type III secretion system may be used. Type III secretion systems are known in the art. This type of antigen delivery system delivers the antigen to the cytoplasm of cells in the host to enhance induction of CTL responses. Yet another type of antigen delivery strategy that may be used is regulated delayed lysis of a bacterium in vivo to release protein antigen(s) and/or viral proteins. The viral proteins may include viral core particles with or without epitope fusion. Regulated antigen delivery systems are known in the art. See, for example, U.S. Pat. No. 6,780,405, hereby incorporated by reference in its entirety. In other embodiments, the antigen may be delivered to the cytosol of a host cell by lysis of the recombinant bacterium. Such lysis may be regulated as described herein.

In one embodiment, the antigen may be a GAPDH protein derived from a fish pathogen such as *E. ictaluri, E. tarda*, or *F. columnare.*

In an exemplary embodiment, an antigen may be used to elicit a protective immune response to one or more fish pathogens. As used herein, “fish pathogen” refers to a bacterium virus, fungus, parasite, or protozoan organism capable of causing disease in a fish. For instance, an antigen may be used to elicit a protective immune response to both *E. ictaluri* and *F. columnaris*. Alternatively, an antigen may be used to elicit a protective immune response to *E. ictaluri, E. tarda*, and/or *F. columnare.*

B. Promoter Regulated by Repressor

The vector comprises a nucleic acid sequence encoding at least one antigen operably-linked to a promoter regulated by the repressor, encoded by a chromosomally integrated nucleic acid sequence. One of skill in the art would recognize, therefore, that the selection of a repressor dictates, in part, the selection of the promoter operably-linked to a nucleic acid sequence encoding an antigen of interest. For instance, if the repressor is LacI, then the promoter may be selected from the group consisting of LacI responsive promoters, such as $P_{trc}$, $P_{lac}$, $P_{T7lac}$ and $P_{tac}$. If the repressor is C2, then the promoter may be selected from the group consisting of C2 responsive promoters, such as P22 promoters $P_L$ and $P_R$. If the repressor is C1, then the promoter may be selected from the group consisting of C1 responsive promoters, such as λ promoters $P_L$ and $P_R$.

In each embodiment herein, the promoter regulates expression of a nucleic acid sequence encoding the antigen, such that expression of the nucleic acid sequence encoding an antigen is repressed when the repressor is synthesized (i.e. during in vitro growth of the bacterium), but expression of the nucleic acid sequence encoding an antigen is high when the repressor is not synthesized (i.e. in an animal or human host). Generally speaking, the concentration of the repressor will decrease with every cell division after expression of the nucleic acid sequence encoding the repressor ceases. In some embodiments, the concentration of the repressor decreases enough to allow high level expression of the nucleic acid sequence encoding an antigen after about 2, 3, 4, 5, 6, 7, 8, 9, 10, 11, or 12 divisions of the bacterium. In an exemplary embodiment, the concentration of the repressor decreases enough to allow high level expression of the nucleic acid sequence encoding an antigen after about 5 divisions of the bacterium in an animal or human host.

In certain embodiments, the promoter may comprise other regulatory elements. For instance, the promoter may comprise lacO if the repressor is LacI. This is the case with the lipoprotein promoter $P_{lpp}$ that is regulated by LacI since it possesses the LacI binding domain lacO.

In one embodiment, the repressor is a LacI repressor and the promoter is $P_{trc}$.

C. Expression of the Nucleic Acid Sequence Encoding an Antigen

As detailed above, generally speaking the expression of the nucleic acid sequence encoding the antigen should be repressed when the repressor is synthesized. For instance, if the repressor is synthesized during in vitro growth of the bacterium, expression of the nucleic acid sequence encoding the antigen should be repressed. Expression may be “repressed” or “partially repressed” when it is about 50%, 45%, 40%, 35%, 30%, 25%, 20%, 15%, 10%, 5%, 1%, or even less than 1% of the expression under non-repressed conditions. Thus although the level of expression under conditions of “complete repression” might be exceeding low, it is likely to be detectable using very sensitive methods since repression is generally not absolute.

Conversely, the expression of the nucleic acid sequence encoding the antigen should be high when the expression of the nucleic acid sequence encoding the repressor is repressed. For instance, if the nucleic acid sequence encoding the repressor is not expressed during growth of the recombinant bacterium in the host, the expression of the nucleic acid sequence encoding the antigen should be high. As used herein, "high level" expression refers to expression that is strong enough to elicit an immune response to the antigen. Consequently, the copy number correlating with high level expression can and will vary depending on the antigen and the type of immune response desired. Methods of determining whether an antigen elicits an immune response such as by measuring antibody levels or antigen-dependant T cell populations or antigen-dependant cytokine levels are known in the art, and methods of measuring levels of expression of antigen encoding sequences by measuring levels of mRNA transcribed or by quantitating the level of antigen synthesis are also known in the art.

D. Inhibiting Recombination

Although extrachromosomal vectors, such as plasmids, may be designed with unique nucleotide sequences, there is some potential for vector-vector recombination to occur that might lead to deletion of and/or alterations in one or more nucleic acid sequences encoding an antigen of interest. This could potentially expose a host to unintended antigens. Accordingly, in some embodiments, a recombinant bacterium of the invention may be deficient in one or more of the enzymes that catalyzes recombination between extrachromosomal vectors. If a bacterium comprises only a single extrachromosomal vector, then such mutations are not necessary. If two or more extrachromosomal vectors are used, however, then the recombinant bacterium may be modified so that one or more recombination enzymes known to catalyze vector-vector recombination are rendered non-functional.

In certain embodiments, the recombination enzymes do not participate in recombinations involving chromosomal nucleic acid sequences. For instance, the recombinant bacterium may comprise a ΔrecF and a ΔrecJ mutation. These mutations do not alter the virulence attributes of the recombinant bacterium, nor its ability to effectively colonize effector lymphoid tissues after immunization of a host. One of skill in the art will appreciate that other recombination enzymes known to catalyze vector-vector recombination but not to participate in recombinations involving chromosomal nucleic acid sequences may be targeted for deletion or mutation in addition to recF and recJ.

Alternatively, the recombinant bacterium may be modified by introducing a ΔrecA mutation that prevents all recombination, whether between vectors or chromosomal nucleic acid sequences. A recombinant bacterium with a ΔrecA mutation may also be attenuated.

(b) Attenuation

A recombinant bacterium of the invention is typically attenuated. "Attenuated" refers to the state of the bacterium wherein the bacterium has been weakened from its wild type fitness by some form of recombinant or physical manipulation. This includes altering the genotype of the bacterium to reduce its ability to cause disease. However, the bacterium's ability to colonize the host and induce immune responses is, preferably, not substantially compromised.

Methods for attenuating a bacterium are known in the art. Non-limiting examples of attenuation methods are detailed below.

i. Regulated Attenuation

In some embodiments, the attenuation may be regulated attenuation. In these embodiments, the bacterium generally comprises a chromosomally integrated regulatable promoter. The promoter replaces the native promoter of, and is operably linked to, at least one nucleic acid sequence encoding an attenuation protein, such that the absence of the function of the protein renders the bacterium attenuated. In some embodiments, the promoter is modified to optimize the regulated attenuation.

A. Attenuation Protein

Herein, "attenuation protein" is meant to be used in its broadest sense to encompass any protein the absence of which attenuates a bacterium. For instance, in some embodiments, an attenuation protein may be a protein that helps protect a bacterium from stresses encountered in the gastrointestinal tract or respiratory tract. Non-limiting examples may be the Fur and Crp proteins. In other embodiments, the protein may be a necessary component of the cell wall of the bacterium, such as the protein encoded by murA. In still other embodiments, the protein may be involved in the production of LPS, such as the protein encoded by the insA or gne nucleic acid sequence.

The native promoter of at least one, two, three, four, five, or more than five attenuation proteins may be replaced by a regulatable promoter as described herein. In one embodiment, the promoter of one of the proteins Fur or Crp may be replaced. In another embodiment, the promoter of both Fur and Crp may be replaced.

If the promoter of more than one attenuation protein is replaced, each promoter may be replaced with a regulatable promoter, such that the expression of each attenuation protein encoding sequence is regulated by the same compound or condition. Alternatively, each promoter may be replaced with a different regulatable promoter, such that the expression of each attenuation protein encoding sequence is regulated by a different compound or condition such as by the sugars arabinose, rhamnose or xylose.

B. Regulatable Promoter Operably Linked to a Nucleic Acid Encoding an Attenuation Protein The native promoter of a nucleic acid encoding an attenuation protein is replaced with a regulatable promoter operably linked to the nucleic acid sequence encoding an attenuation protein. The term "operably linked," is defined above.

The regulatable promoter used herein generally allows transcription of the nucleic acid sequence encoding the attenuation protein while in a permissive environment (i.e. in vitro growth), but ceases transcription of the nucleic acid sequence encoding an attenuation protein while in a non-permissive environment (i.e. during growth of the bacterium in an animal or human host). For instance, the promoter may be responsive to a physical or chemical difference between the permissive and non-permissive environment. Suitable examples of such regulatable promoters are known in the art and detailed above.

In some embodiments, the promoter may be responsive to the level of arabinose in the environment, as described above. In other embodiments, the promoter may be responsive to the level of rhamnose, or xylose in the environment. The promoters detailed herein are known in the art, and methods of operably linking them to a nucleic acid sequence encoding an attenuation protein are known in the art.

In certain embodiments, a recombinant bacterium of the invention may comprise a $\Delta P_{fur}$::TT araC $P_{BAD}$ fur mutation, $\Delta P_{crp}$::TT araC $P_{BAD}$ crp mutation, a $\Delta P_{insA}$::TT araC $P_{BAD}$ insA mutation, a Δgne-25 mutation, or a combination thereof. For instance, a bacterium may comprise a $\Delta P_{fur70}$::TT araC $P_{BAD}$ fur mutation, a $\Delta P_{crp11}$::TT araC $P_{BAD}$ crp mutation, or a $\Delta P_{insA40}$::TT araC $P_{BAD}$ insA mutation, or a combination thereof. Growth of such strains in the presence of arabinose leads to transcription of the fur and/or crp and/or insA nucleic acid sequences, but nucleic acid sequence expression ceases in a host because there is no free arabinose (FIG. 1). Attenuation develops as the products of the fur and/or the crp and/or the insA nucleic acid sequences are diluted at each cell division.

Generally speaking, the concentration of arabinose necessary to induce expression is typically less than about 2%. In some embodiments, the concentration is less than about 1.5%, 1%, 0.5%, 0.2%, 0.1%, or 0.05%. In certain embodiments, the concentration may be about 0.04%, 0.03%, 0.02%, or 0.01%. In an exemplary embodiment, the concentration is about 0.05%. Higher concentrations of arabinose or other sugars may lead to acid production during growth that may inhibit desirable cell densities. The inclusion of mutations such as ΔaraBAD or mutations that block the uptake and/or breakdown of rhamnose, or xylose, however, may prevent such acid production and enable use of higher sugar concentrations with no ill effects.

When the regulatable promoter is responsive to arabinose, the onset of attenuation may be delayed by including additional mutations that would prevent use of arabinose or enhance retention of arabinose. Thus, inclusion of these mutations may be beneficial in at least two ways: first, enabling higher culture densities, and second enabling a further delay in the display of the attenuated phenotype that may result in higher densities in effector lymphoid tissues to further enhance immunogenicity.

C. Modifications

Attenuation of the recombinant bacterium may be optimized by modifying the promoter and/or the nucleic acid sequence encoding an attenuation protein. Methods of modifying a promoter and/or a nucleic acid sequence encoding an attenuation protein are the same as those detailed above with respect to repressors in Section I(a).

In some embodiments, more than one modification may be performed to optimize the attenuation of the bacterium. For instance, at least one, two, three, four, five, six, seven, eight or nine modifications may be performed to optimize the attenuation of the bacterium.

In various exemplary embodiments of the invention, the SD sequences and/or the start codons for the fur nucleic acid sequences may be altered so that the production levels of these nucleic acid products are optimal for regulated attenuation.

D. Regulated Attenuation and Regulated Expression of a Nucleic Acid Sequence Encoding an Antigen In an exemplary embodiment, a recombinant bacterium may be attenuated as described above and may be capable of the regulated expression of a nucleic acid sequence encoding an antigen, as described in section I(a) above. In which case, both regulated attenuation and regulated expression of an antigen encoding sequence may be dependent upon an arabinose regulatable system. Consequently, the concentration of arabinose needed for optimal expression of the regulated antigen encoding sequence may not be the same as the concentration for optimal expression of attenuation. In an exemplary embodiment, the concentration of arabinose for the optimization of both regulated attenuation and regulated expression of sequences encoding antigen will be substantially the same.

Accordingly, the promoter and/or the nucleic acid sequence encoding an attenuation protein may be modified to optimize the system. Methods of modification are detailed above. One of skill in the art will appreciate that other nucleic acid sequences, in addition to fur, may also be altered as described herein in combination with other well-known protocols. In addition, these attenuating nucleic acid sequences may be regulated by other systems using well-established protocols known to one of skill in the art. For example, they may be regulated using promoters dependent on addition of rhamnose, or xylose rather than arabinose.

ii. Other Attenuation Methods

Figure 32:
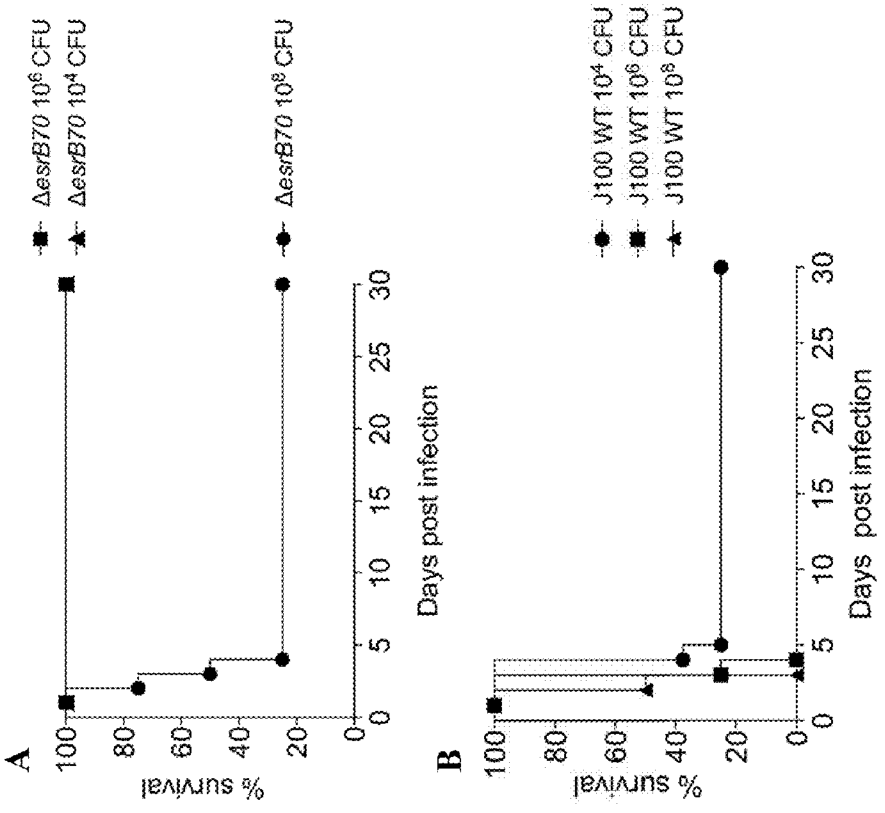
FIG. 32 depicts an illustration of zebrafish survival post I.M. infection with J100 *E. ictaluri* 2003/C wild type (n=50 per dose)(B) and *E. ictaluri* ΔesrB70 (n=15 per dose)(A); the experiments were performed twice, independently.
Figure 33:
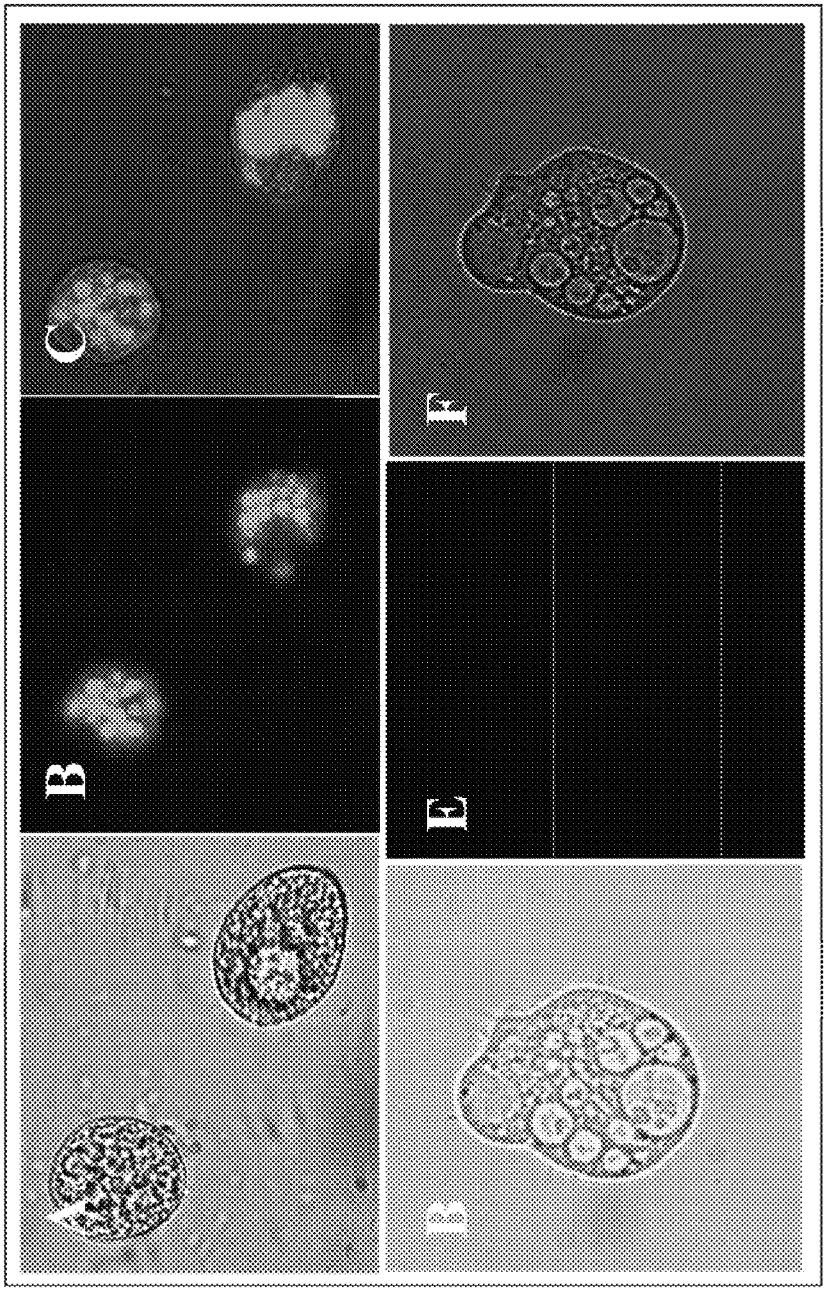
FIG. 33 depicts an illustration of deletion the protozoa *Paramecium* sp, a typical source of live food for fish frys, colonized by (A-C) *E. ictaluri* J112 (pYA3994) $Asd^+$ $GFP^+$. Paramecium not fed *E. ictaluri* was used as control (D-E)

Other methods of attenuation are known in the art. For instance, attenuation may be accomplished by altering (e.g., deleting) native nucleic acid sequences found in the wild type bacterium. In some embodiments, the bacterium may comprise a mutation in a transcription factor as a means to attenuate the bacterium. By way of non-limiting example, the bacterium may comprise a ΔesrB70 mutation (FIG. 32).

In certain embodiments, the above nucleic acid sequences may be placed under the control of a sugar regulated promoter wherein the sugar is present during in vitro growth of the recombinant bacterium, but substantially absent within an animal or human host. The cessation in transcription of the nucleic acid sequences listed above would then result in attenuation and the inability of the recombinant bacterium to induce disease symptoms.

In another embodiment, the recombinant bacterium may contain one and in some embodiments, more than one, deletion and/or deletion-insertion mutation present in the strains listed in Table A above. Vectors listed in Table A and described in the Examples below, along with other plasmid vectors, may be used to introduce these deletion and deletion-insertion mutations into strains during their construction.

The bacterium may also be modified to create a balanced-lethal host-vector system, although other types of systems may also be used (e.g., creating complementation heterozygotes).

(c) Crp Cassette

In some embodiments, a recombinant bacterium of the invention may also comprise a $\Delta P_{crp}$::TT araC $P_{BAD}$ crp deletion-insertion mutation. Since the araC $P_{BAD}$ cassette is dependent both on the presence of arabinose and the binding of the catabolite repressor protein Crp, a $\Delta P_{crp}$::TT araC $P_{BAD}$ crp deletion insertion mutation may be included as an additional means to reduce expression of any nucleic acid sequence under the control of the $P_{BAD}$ promoter. This means that when the bacterium is grown in a non-permissive environment (i.e. no arabinose) both the repressor itself and the Crp protein cease to be synthesized, consequently eliminating both regulating signals for the araC $P_{BAD}$ regulated nucleic acid sequence. This double shut off of araC $P_{BAD}$ may constitute an additional safety feature ensuring the genetic stability of the desired phenotypes.

Generally speaking, the activity of the Crp protein requires interaction with cAMP (FIGS. 14-18), but the addition of glucose, which may inhibit synthesis of cAMP, decreases the ability of the Crp protein to regulate transcription from the araC $P_{BAD}$ promoter. Consequently, to avoid the effect of glucose on cAMP, glucose may be substantially excluded from the growth media, or variants of crp may be isolated that synthesize a Crp protein that is not dependent on cAMP to regulate transcription from $P_{BAD}$. This strategy may also be used in other systems responsive to Crp, such as the systems responsive to rhamnose and xylose described above.

(d) Regulated Lysis

A recombinant bacterium of the invention may be capable of regulated lysis. For instance, the bacterium may be modified by manipulating its ability to synthesize various essential constituents needed for synthesis of the rigid peptidoglycan layer of its cell wall. In one example, the constituent is diaminopimelic acid (DAP). Various enzymes are involved in the eventual synthesis of DAP. In one example, the bacterium is modified by using a ΔasdA mutation to eliminate the bacterium's ability to produce β-aspartate semialdehyde dehydrogenase, an enzyme essential for the synthesis of DAP. One of skill in the art can also use the teachings of U.S. Pat. No. 6,872,547 for other types of mutations of nucleic acid sequences that result in the abolition of the synthesis of DAP. These nucleic acid sequences may include, but are not limited to, dapA, dapB, dapC, dapD, dapE, dapF, and asd. Other modifications that may be employed include modifications to a bacterium's ability to synthesize D-alanine or to synthesize D-glutamic acid (e.g., Δalr and ΔmurI mutations), which are both unique constituents of the peptidoglycan layer of the bacterial cell wall Similarly, various embodiments may comprise the araC $P_{BAD}$ c2 cassette inserted into the asd nucleic acid sequence that encodes aspartate semialdehyde dehydrogenase. Such a mutation may comprise ΔasdA02::TT araC $P_{BAD}$ c2. Since the araC nucleic acid sequence is transcribed in a direction that could lead to interference in the expression of adjacent nucleic acid sequences and adversely affect vaccine strain performance, a transcription termination (TT) sequence is generally inserted 3' to the araC nucleic acid sequence. The chromosomal asd nucleic acid sequence is typically inactivated to enable use of plasmid vectors encoding the wild-type asd nucleic acid sequence in the balanced lethal host-vector system. This allows stable maintenance of plasmids in vivo in the absence of any drug resistance attributes that are not permissible in live bacterial vaccines. In some of these embodiments, the wild-type asd nucleic acid sequence may be encoded by the vector described above. The vector enables the regulated expression of an antigen encoding sequence through the repressible promoter.

In another example, a recombinant bacterium may comprise a $\Delta P_{murA}$::TT araC $P_{BAD}$ murA deletion-insertion mutation. This mutation modifies the bacterium such that the synthesis of an essential constituent of the rigid layer of the bacterial cell wall is dependent on a nutrient (e.g., arabinose) that can be supplied during the growth of the microorganism. This type of mutation makes synthesis of muramic acid (a unique essential constituent of the peptidoglycan layer of the bacterial cell wall) dependent on the presence of arabinose that can be supplied during growth of the bacterium in vitro.

When arabinose is absent, however, as it is in an animal or human host, the essential constitutent of the peptidoglycan layer of the cell wall is not synthesized. This mutation represents an arabinose dependant lethal mutation. In the absence of arabinose, synthesis of muramic acid ceases and lysis of the bacterium occurs because the peptidoglycan layer of the cell wall is not synthesized. It is not possible to generate ΔmurA mutations because they are lethal. The necessary nutrient, a phosphorylated muramic acid, can not be exogenously supplied because enteric bacteria cannot take the nutrient up from the media. Recombinant bacteria with a $\Delta P_{murA}$::TT araC $P_{BAD}$ murA deletion-insertion mutation grown in the presence of arabinose exhibit effective colonization of effector lymphoid tissues after oral vaccination prior to undergoing lysis due to the inability to synthesize muramic acid.

II. Vaccine Compositions and Administration

A recombinant bacterium of the invention may be administered to a host as a vaccine composition. As used herein, a vaccine composition is a composition designed to elicit an immune response to the recombinant bacterium, including any antigens that may be expressed by the bacterium. In an exemplary embodiment, the immune response is protective, as described above. Immune responses to antigens are well studied and widely reported. A survey of immunology is given by Paul, W E, Stites D et al. and Ogra P L. et al. Mucosal immunity is also described by Ogra P L et al.

Vaccine compositions of the present invention may be administered to a host capable of mounting an immune response. Preferably, the host is a fish. In an exemplary embodiment, the host is a fish used in aquaculture. The vaccine can be administered as a prophylactic or for treatment purposes.

In exemplary embodiments, the recombinant bacterium is alive when administered to a host in a vaccine composition of the invention. In another exemplary embodiment, the recombinant bacterium administered to a host in a vaccine composition comprises one or more of the mutations selected from the group comprising $\Delta P_{crp11}$::TT araC $P_{BAD}$ crp, $\Delta P_{fur70}$::TT araC $P_{BAD}$ fur; $\Delta P_{insA40}$::TT araC $P_{BAD}$ insA or Δgne-25; ΔesrB80; ΔrelA50::araC $P_{BAD}$ lacI TT; ΔasdA02::TT araC $P_{BAD}$ c2; and $\Delta P_{murA60}$::TT araC $P_{BAD}$ murA. For instance, the bacterium may comprise one, two, three, four, five, six, or seven mutations from the group comprising $\Delta P_{crp11}$::TT araC $P_{BAD}$ crp, $\Delta P_{fur70}$::TT araC $P_{BAD}$ fur; $\Delta P_{insA40}$::TT araC $P_{BAD}$ insA or Δgne-25; ΔesrB80; ΔrelA50::araC $P_{BAD}$ lacI TT; ΔasdA02::TT araC $P_{BAD}$ c2; and $\Delta P_{murA60}$::TT araC $P_{BAD}$ murA. With the exception of asd mutations that are used in the balanced-lethal vector-host system and are complemented in vaccine bacterium strains, all of the above mutations do not impose any auxotrophic requirements for nutrients. Bacteria; strains with these mutations are therefore not auxotrophs.

In certain embodiments, a vaccine of the invention may elicit an immune response against *Edwardsiella* in a host. In other embodiments, a vaccine of the invention may elicit an immune response against a fish pathogen other than *Edwardsiella* in a host. For instance, a vaccine composition of the invention may elicit an immune response to *E. ictalui* and/or *F. columnare*. In an exemplary embodiment, a vaccine composition of the invention may elicit an immune response to *E. ictalui, F. columnare*, and *E. tarda*. In further embodiments, a vaccine of the invention may elicit an immune response to a viral, fungal, protozoan, or parasitic pathogen of a fish in a host. In each of the above embodiments, the immune response may be a protective immune response.

Suitable vaccine composition formulations and methods of administration are detailed below.

(a) Vaccine Composition

A vaccine composition comprising a recombinant bacterium of the invention may optionally comprise one or more possible additives, such as carriers, preservatives, stabilizers, adjuvants, and other substances.

In one embodiment, the vaccine comprises an adjuvant. In exemplary embodiments, the use of a live attenuated recombinant bacterium may act as a natural adjuvant.

In another embodiment, the vaccine may comprise a pharmaceutical carrier (or excipient). Such a carrier may be any solvent or solid material for encapsulation that is non-toxic to the inoculated host and compatible with the recombinant bacterium. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995).

Care should be taken when using additives so that the live recombinant bacterium is not killed, or have its ability to effectively colonize lymphoid tissues such as the GALT, and NALT compromised by the use of additives. Stabilizers, such as lactose or monosodium glutamate (MSG), may be added to stabilize the vaccine formulation against a variety of conditions, such as temperature variations or a freeze-drying process.

In exemplary embodiments, a vaccine composition of the invention is administered in a bath. For instance, a vaccine composition may be administered to fish fry in a bath. In other exemplary embodiments, a vaccine composition of the invention may be administered in a live fish food, such as protozoa. In certain exemplary embodiments, a vaccine composition of the invention may be administered via food pellets for oral consumption. By way of non-limiting example, booster administration may be given via food pellets.

The dosages of a vaccine composition of the invention can and will vary depending on the recombinant bacterium, the regulated antigen, and the intended host, as will be appreciated by one of skill in the art. Generally speaking, the dosage need only be sufficient to elicit a protective immune response in a majority of hosts. Routine experimentation may readily establish the required dosage. Typical initial dosages of vaccine for oral administration or uptake via gills could be about $1\times10^7$ to $1\times10^{10}$ CFU depending upon the age of the host to be immunized. Administering multiple dosages may also be used as needed to provide the desired level of protective immunity.

(b) Methods of Administration

In order to simplify aquaculture use, bath/oral administration is preferred. Other routes of administration may include intranasal administration, gastric intubation, intravenous, intramuscular, subcutaneous injection or other parenteral routes, are possible.

In some embodiments, these compositions are formulated for administration by injection (e.g., intraperitoneally, intravenously, subcutaneously, intramuscularly, etc.). Accordingly, these compositions are preferably combined with pharmaceutically acceptable vehicles such as saline, Ringer's solution, dextrose solution, and the like.

III. Kits

The invention also encompasses kits comprising any one of the compositions above in a suitable aliquot for vaccinating a host in need thereof. In one embodiment, the kit further comprises instructions for use. In other embodiments, the composition is lyophilized such that addition of a hydrating agent (e.g., buffered saline) reconstitutes the composition to generate a vaccine composition ready to administer, preferably orally.

IV. Methods of Use

A further aspect of the invention encompasses methods of using a recombinant bacterium of the invention. For instance, in one embodiment the invention provides a method for modulating a host's immune system. The method comprises administering to the host an effective amount of a composition comprising a recombinant bacterium of the invention. One of skill in the art will appreciate that an effective amount of a composition is an amount that will generate the desired immune response (e.g., mucosal, humoral or cellular). Methods of monitoring a host's immune response are well-known to veterinarians and other skilled practitioners. For instance, assays such as ELISA may be used. Effectiveness may be determined by monitoring the amount of the antigen of interest remaining in the host, or by measuring a decrease in disease incidence caused by a given pathogen in a host. For certain pathogens, cultures or swabs taken as biological samples from a host may be used to monitor the existence or amount of pathogen in the individual.

In another embodiment, the invention provides a method for eliciting an immune response against an antigen in a host. The method comprises administering to the host an effective amount of a composition comprising a recombinant bacterium of the invention.

In still another embodiment, a recombinant bacterium of the invention may be used in a method for eliciting an immune response against a pathogen in an individual in need thereof. The method comprises administrating to the host an effective amount of a composition comprising a recombinant bacterium as described herein. In a further embodiment, a recombinant bacterium described herein may be used in a method for ameliorating one or more symptoms of an infectious disease in a host in need thereof. The method comprises administering an effective amount of a composition comprising a recombinant bacterium as described herein.

Definitions

The term "altered," as used herein, refers to any change in the nucleic acid sequence that results in the nucleic acid sequence not being expressed. In an exemplary embodiment, the alteration results in the nucleic acid sequence not being expressed in a host. In one embodiment, the alteration is a deletion. In another embodiment, the alteration places an essential nucleic acid under the control of a regulatable promoter, such that the nucleic acid is not expressed in a host.

The term "balanced-lethal" or "balanced attenuated" host vector systems refers to a recombinant bacterium comprising at least one chromosomally encoded essential nucleic acid sequence, wherein the essential nucleic acid sequence is altered so that it is not expressed, and at least one extrachromosomal vector. An "essential nucleic acid" is a native nucleic acid whose expression is necessary for cell viability or a metabolic activity essential for virulence. Consequently, a bacterium of the invention is non-viable and/or avirulent if an essential nucleic acid sequence is not expressed. Therefore, the bacterium further comprises at least one extrachromosomal vector. The vector comprises a nucleic acid sequence, that when expressed, substantially functions as the essential nucleic acid. Hence, the bacterium is viable and/or virulent when the vector is expressed. This promotes stable maintenance of the vector.

The term "native," as used herein, refers to a biomolecule in a form typically found in the strain a recombinant bacterium of the invention is derived from.

The term "promoter", as used herein, may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same.

The term "virulence," as used here, refers to the ability of the recombinant bacterium to infect a host.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Example 1

Genetically Attenuated *E. ictaluri* and Immunogenicity Enhancement

In terms of efficacy, the RAEV should offer protection to the diseases caused by the target bacterial pathogens and this will depend on the ability to induce a protective immune response. Typically, a desirable immune response includes a combination of humoral, cell-mediated and mucosal immunity. Live attenuated bacterial vaccines achieve these goals through colonization of external and deep lymphoid tissues, like the kidney, spleen and liver of the fish. However, hyper attenuation will not trigger the required immune response since it usually results in modest colonization of these internal lymphoid organs. The attenuation design must therefore maintain a balance between colonization and attenuation. In this regard, use of a regulated delayed attenuation system achieves this goal.

We have developed means to permit a regulated delayed attenuation phenotype so that vaccine strains at the time of immunization exhibit nearly wild-type attributes for survival and colonization of the lymphoid tissues and then as a function of cell division become avirulent and unable to cause any disease symptoms or depress growth. Regulated delayed attenuation relies on substituting an araC $P_{BAD}$ activator-promoter that is more tightly regulated than the original araC $P_{BAD}$ for a promoter of a virulence gene such that in the absence of arabinose in vivo attenuation is manifest. Thus virulence gene expression is restricted to the presence of arabinose included in the vaccine growth medium. We have evaluated the presence of arabinose in catfish tissues and food by using a genetically modified *Salmonella* strain that depends on arabinose to replicate. We found that $\chi$9442 *S. Typhimurum* $\Delta P_{murA12}$::TT araC $P_{BAD}$ murA (A=deletion; P=promotor; TT=transcriptional terminator) did not replicate and underwent muramic acid-less death by lysis in catfish tissues and fish food, indicating the absence of free-arabinose in the environment that RAEV will likely encounter (FIG. 1). We also evaluated Zebrafish and Trout meat with similar results.

Three means will ultimately be used for RAEV construction. Deletion of the crp gene attenuates *S. Typhimurium* in mice and chickens and also attenuates *E. ictaluri* for Zebrafish (*Danio rerio*) (Table 1).

TABLE 1

Virulence by *E. ictaluri* following intramuscular injection (10 μL) of Zebrafish (*Danio Rerio*) 8-12 weeks

| Strain | Dose | Route | Survivors/death |
|---|---|---|---|
| Wild-type | $8.5 \times 10^8$ | I.M | 0/25 |
| | $8.5 \times 10^6$ | I.M | 0/25 |
| | $8.5 \times 10^4$ | I.M | 2/25 |
| Δcrp-10 | $1.6 \times 10^8$ | I.M | 0/15 |
| | $1.6 \times 10^6$ | I.M | 3/15 |
| | $1.6 \times 10^4$ | I.M | 13/15 |
| BSG (control) | — | I.M | 10/10 |

Figure 2:
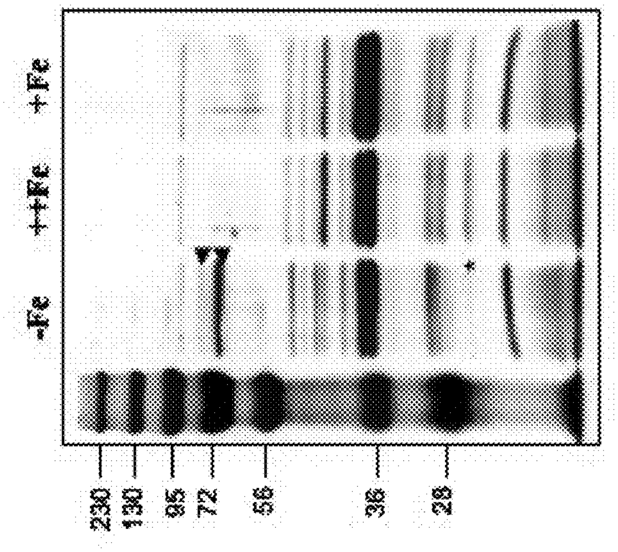
FIG. 2 depicts a protein blot illustrating *E. ictaluri* IROMP expression. *E. ictaluri* OMP profile. The arrows indicate the IROMPs expression in absence of iron (−Fe); the * indicate the down regulated OMP in absence of iron. ++Fe excess of iron; +Fe iron from the media.

Deletion of gne attenuates *E. ictaluri* in catfish and precludes the synthesis of LPS. The gne gene shares high similarity with the galE gene. Deletion of galE in *Salmonella* or *E. coli* precludes the interconversion of UDP-glucose and UDP-galactose, thus in the absence of galactose the full LPS core and O-antigen are not synthesized. We identified and deleted galE in *E. ictaluri*, but this only affects galactose utilization. Therefore deletion of gne to regulate LPS synthesis can be used as a second means to attenuate *E. ictaluri* (see below). On the other hand, gradual elimination of LPS O-antigen exposes the immunologically reactive OMPs and IROMPs (FIG. 2). IROMPs are down regulated by the ferric uptake regulator protein (Fur). Deletion of fur attenuates *Salmonella* and *Edwardsiella* and leads to constitutive synthesis of immunogenic IROMPs. Control of fur expression by replacing the promoter for fur ($P_{fur}$) with the tightly regulated araC $P_{BAD}$ cassette enables expression of the *E. ictaluri* IROMPs to be dependant on presence or absence of arabinose. Use of the $\Delta P_{fur70}$::TT araC $P_{BAD}$ fur deletion-insertion mutation not only attenuates, but also should enhance immunogenicity.

Deletion of the promoter, including sequences for activator or repressor protein binding, for crp, insA (LPS O-antigen gene cluster, including gne) and fur genes and substituting the araC $P_{BAD}$ cassette will yield *Edwardsiella* strains with the $\Delta P_{crp11}$::TT araC $P_{BAD}$ crp, ΔPinsA31::TT araC $P_{BAD}$ insA, and $\Delta P_{fur70}$::TT araC $P_{BAD}$ fur deletion-insertion mutations as means to attenuate and enhance immunogenicity. We predict that each of these deletion-insertion mutations will confer a regulated delayed attenuation phenotype. This will be tested for strains with each as well as with combinations of these mutations. We have sequenced and identified crp and fur genes in *E. ictaluri* and deleted crp. Insertion of a regulatory sequence within a deleted gene is flanked by TT to preclude interference in expression of linked flanking genes. Growth of such strains in the presence of arabinose leads to transcription of the crp, fur and LPS O-antigen genes, but expression ceases in vivo since there is no free arabinose in fish tissues (FIG. 1).

Attenuation develops as the products of these genes are diluted at each cell division. Because *Edwardsiella* do not metabolize arabinose, this pentose will only regulate gene expression. Transcription of the $P_{BAD}$ promoter is dependent on both interaction of arabinose with the AraC protein and the Crp protein with the promoter sequence. We will include the $\Delta P_{crp11}$::TT araC $P_{BAD}$ crp mutation as an added safety feature in all vaccine strains since Crp synthesis will also cease and serve as a second means to shut off expression of the fur, LPS and crp genes fused to $P_{BAD}$.

Example 2

Balanced-lethal System and Heterologous Antigen Secretion

Figure 3:
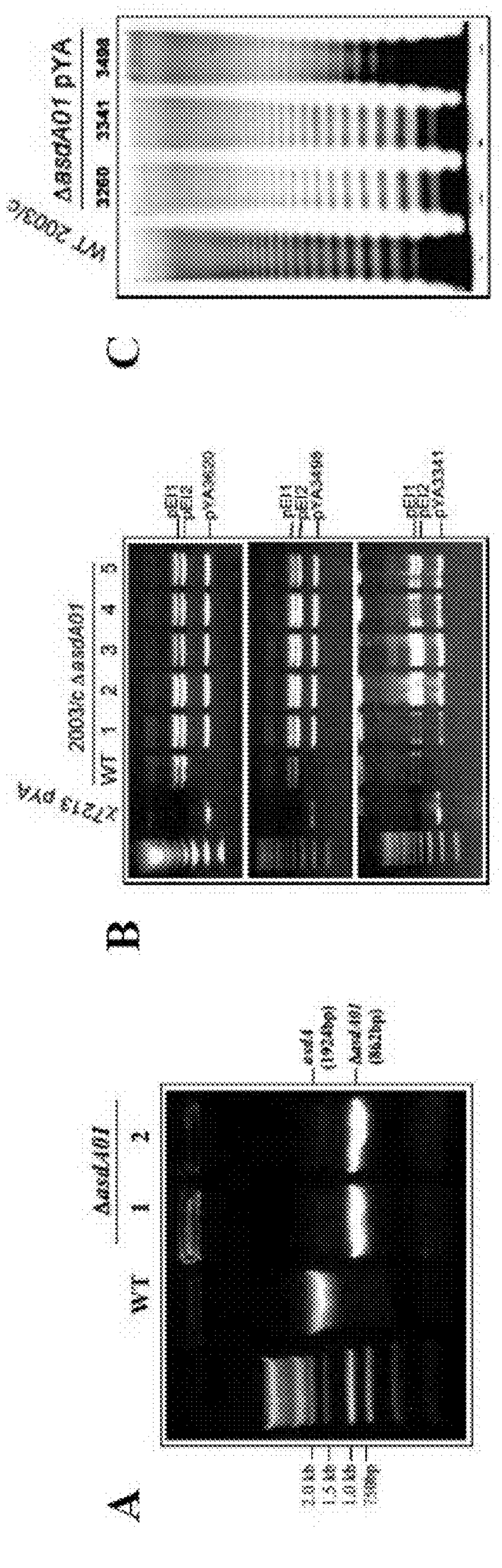
FIG. 3 depicts a series of gel images. (A) PCR verification of J112 *E. ictaluri* ΔasdA01; (B) Plasmid profile of J112 *E. ictaluri* 2003/c ΔasdA01 harboring asd-vectors (lanes1-5); (C) LPS profile of J112 *E. ictaluri* 2003/c ΔasdA01 harboring asd-vectors.
Figure 4:
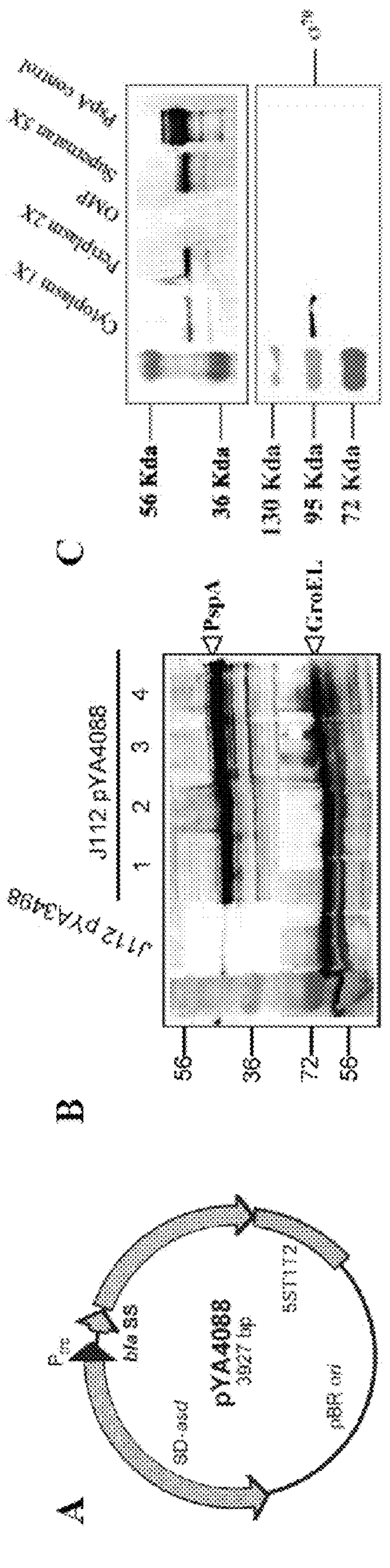
FIG. 4 depicts a drawing and gel images of PspA antigen production. (A) pYA4088, balance-lethal plasmid to secrete PspA by type II secretion system. (B) Western blot, synthesis and secretion of PspA antigen by J112 *E. ictaluri* ΔasdA01 harboring pYA4088. (C) Secretion of PspA by J112 *E. ictaluri* ΔasdA01 harboring pYA4088; the purified PspA protein is represented by PspA control; RpoD was used as cytoplasmic marker.

To eliminate use of plasmid vectors with drug resistance genes (ampicillin, chloramphenicol, kanamycin, tetracycline, rifampicin) and to stabilize plasmid vectors encoding antigens in RAEVs in vivo, the balanced-lethal host-vector system uses the deletion of the asdA gene to impose an obligate requirement for diaminopimlic acid (DAP) and a plasmid vector with the wild-type asdA gene. We deleted asdA in J101 *E. icataluri* and also in J103 *E. ictaluri* ATCC 33202. The ΔasdA01 strains are completely dependent on DAP and were complemented by plasmid vectors with the *S. Typhimurium* asdA gene and having pSC101 ori, p15A ori, pBR on and pUC ori. These $AsdA^+$ plasmid vectors are compatible with pEI1 and pEI2 present in *E. ictaluri* (FIG. 3). We also tested the expression of heterologous antigens by using a gram-positive antigen. PspA, a protective antigen from *Streptococcus pneumoniae*, was synthesized and secreted through type II secretion system in *E. ictaluri* (FIG. 4). These results indicated that *E. ictaluri* is able to synthesize gram-positive heterologous antigens, and secreted it through the hypothetic type II secretion system. So far, we have successfully developed the first balanced-lethal vector-host system in *E. ictaluri*, a key to constructing RAEVs. Although $AsdA^+$ vectors with the *Salmonella* asdA gene seem to be satisfactory, we will substitute the *E. ictaluri* asdA gene to see if there is any improvement. These strains are sensitive to all antibiotics, an attribute of extreme importance in using live attenuated vaccines that are released into the environment.

Example 3

Regulated Delayed Protective Antigen Synthesis

Over expression of protective antigens can be deleterious to the vector bacterial strain, reducing growth rate and colonizing ability and thus immunogenicity. On the other hand, high-level expression of recombinant protective antigens is very important to induce significant protective mucosal and systemic antibody responses. Guanosine tetraphosphate (ppGpp) is a low-molecular-weight effector molecule, which accumulates to high levels during amino acid starvation and correlates with a rapid inhibition of RNA synthesis, both phenotypes being associated with the stringent response. The enzyme responsible for the synthesis of ppGpp during amino acid starvation is a ribosome-associated protein encoded by the relA gene. ReIA dependent synthesis of ppGpp occurs during an idling reaction of ribosomes stalled during translation of mRNA in the presence of uncharged tRNAs. Mutations in relA severely reduce or abolish the accumulation of this nucleotide during amino acid starvation, and, consistent with the inverse correlation of ppGpp levels and RNA synthesis, there is an increase in RNA synthesis, the bulk of which is stable rRNA and tRNA. Deletion of relA precludes stringent control, thus antigen synthesis is carried on during starvation conditions. Therefore, delayed antigen synthesis is constructed by replacement of the relA gene with a TT araC $P_{BAD}$ lacI cassette. The LacI repressor is synthesized in the presence of arabinose. LacI binds to the $P_{trc}$ promoter, which controls transcription of the antigen encoding sequences in the plasmid vector (FIG. 4). Thus, in the presence of arabinose, antigen synthesis does not occur until the levels of arabinose and cytoplasmic LacI decrease through cell division after the vaccine strain is multiplying in host lymphoid tissues. The $P_{trc}$ that we have used is constitutive under most environments but actually is more transcriptionally active both anaerobically and aerobically than other promoters selected for in vivo activity. For this reason, the ΔrelA50::araC $P_{BAD}$ lacI TT deletion-insertion mutation will be generated, so the vaccine strain growing in culture in the presence of arabinose will synthesize the LacI repressor at high levels to repress transcription from $P_{trc}$ on the $Asd^+$ plasmid vectors until after immunization when the vaccine strain is already colonizing internal lymphoid tissues. This has been achieved by increasing the expression of the lacI gene by changing the SD sequence from AGGG to AGGA, the lacI start codon from GTG to ATG and optimizing all codons for high-level expression of lacI in *Salmonella* and this is expected in *Edwardsiella*. We have identified the relA gene and are currently constructing the ΔrelA50::araC $P_{BAD}$ lacI TT deletion-insertion mutation in *E. ictaluri.*

Example 4

Regulated Programmed Cell Lysis

Figure 5:
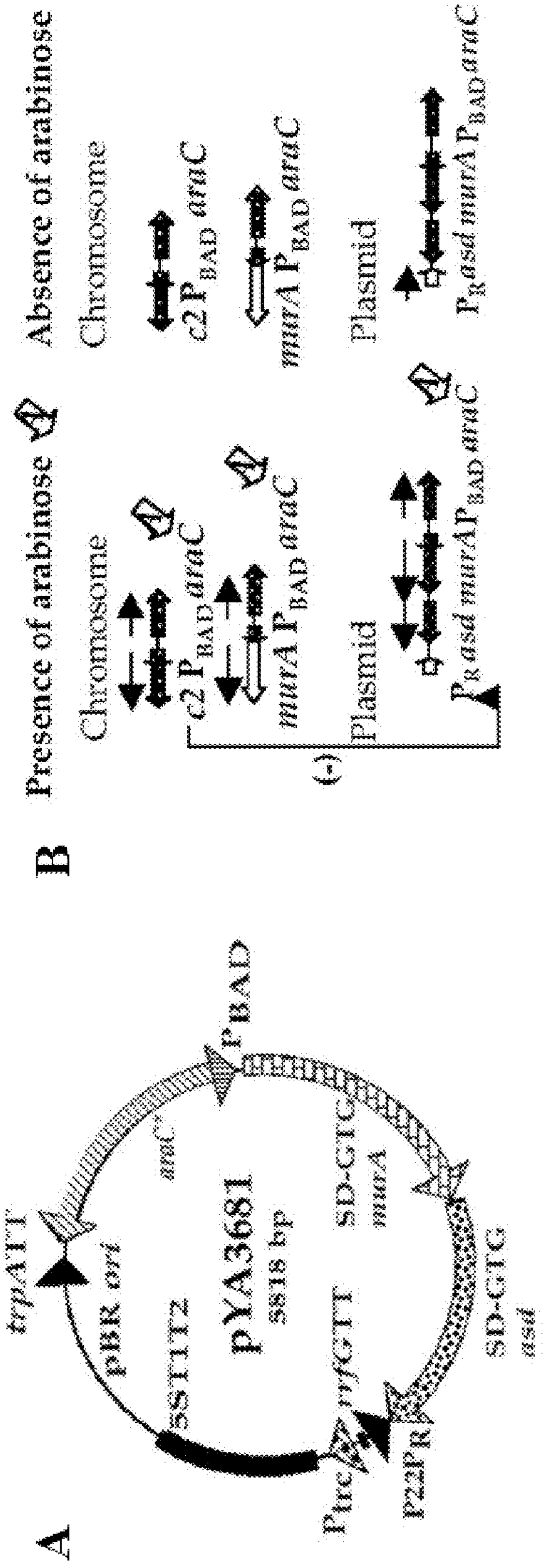
FIG. 5 depicts illustrations showing a regulated programmed lysis system. (A) Map of the plasmid pYA3681. The sequence trpA, rrfG, and 5S ribosomal RNA correspond to transcriptional terminators; $P_{BAD}$, $P_{trc}$, and P22 $P_R$ correspond to promoters. (B) Illustration of the regulatory interactions of the programmed lysis system.

The regulated delayed lysis system relies on asdA and murA genes. DAP and muramic acid are essential components of the peptidoglycan layer of the bacterial cell wall. The asdA gene encodes an enzyme essential for DAP synthesis and the murA gene encodes the first enzyme in muramic acid synthesis. asdA mutants rely on the presence of DAP in the media to support growth. DAP is only synthesized by bacteria and is not present in animal tissues. Unlike lethal deletions, which can be overcome by the addition of DAP to the growth medium, murA deletions, also lethal, cannot be overcome by nutritional supplements. It is therefore necessary to create a conditional-lethal murA mutation by replacing the chromosomal murA promoter with the araC $P_{BAD}$ activator-promoter. Strains with this mutation are dependent on addition of arabinose in all growth media and lyse in the absence of arabinose due to inability to synthesize the peptidoglycan cell wall layer (FIG. 1). The regulated programmed cell lysis is achieved by using a strain with the ΔasdA02::TT araC $P_{BAD}$ c2 and $\Delta P_{murA60}$::TT araC $P_{BAD}$ murA deletion-insertion mutations and complementing the two mutations by a plasmid vector that possesses the wild-type asdA and murA genes under control of araC $P_{BAD}$ (FIG. 5). The plasmid vector pYA3681 contains P22 $P_R$, a C2-regulated promoter, with opposite polarity at the 3' end of the asdA and murA genes. P22 $P_R$ directs synthesis of antisense mRNA to block translation of mRNA transcribed from asdA and murA genes during programmed lysis when arabinose is absent (FIG. 5). Therefore the host strain design for this system contains the ΔasdA02::TT araC $P_{BAD}$ c2 and $\Delta P_{murA60}$::TT araC $P_{BAD}$ murA chromosomal deletion-insertion mutations.

Example 5

Vaccine Design and Construction

Figure 6:
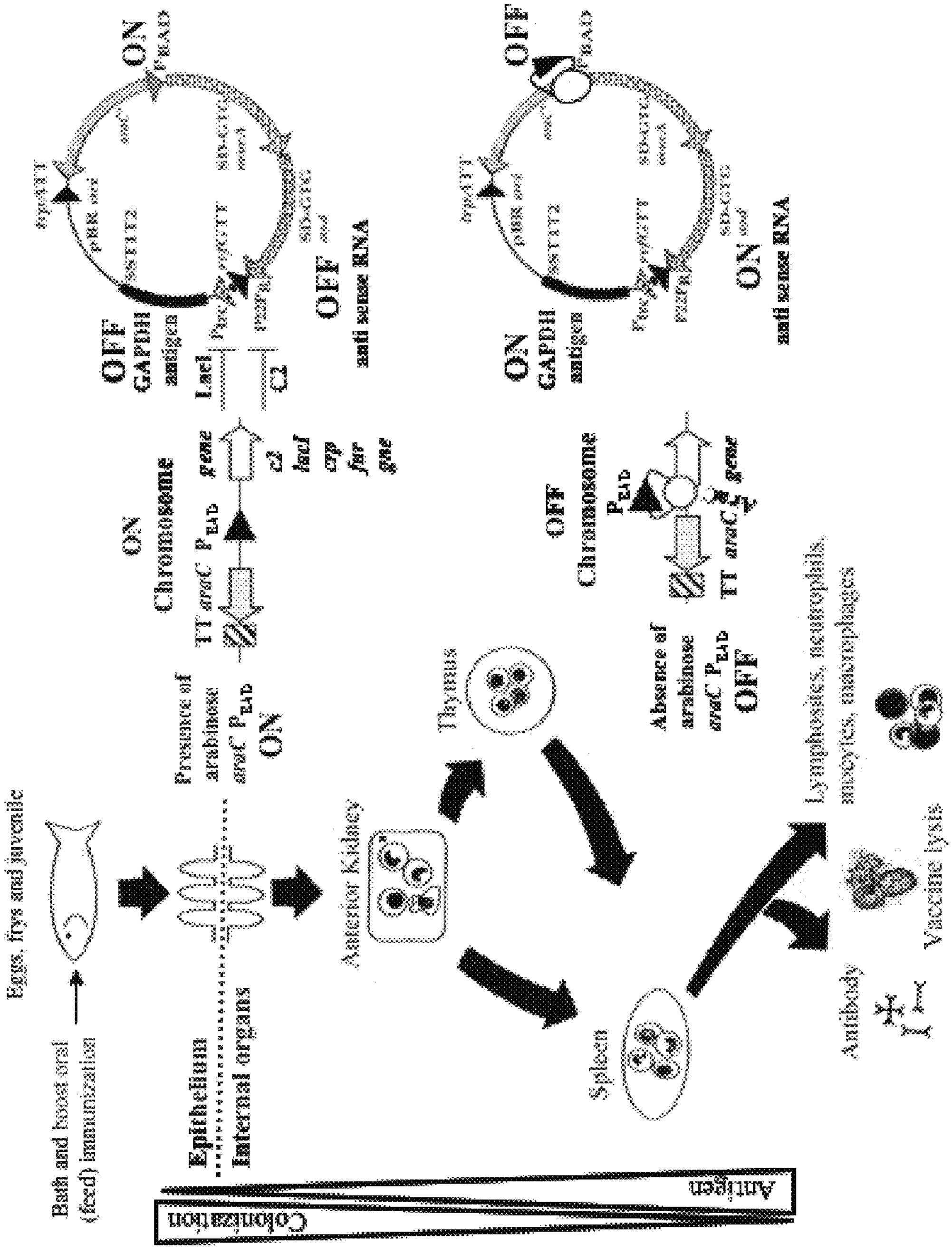
FIG. 6 depicts an illustration of the mechanism of immunization for catfish eggs and/or frys and juveniles by Recombinant Attenuated *Edwardsiella* Vaccine (RAEV). First, RAEV will infect the epithelial cells and cross the mucosal barrier in presence of arabinose. Once the mucosal barrier is crossed no arabinose is available in the fish tissues. Thus, RAEV will slowly turn off the genes under araC $P_{BAD}$ control and will become attenuated and increase antigen secretion in the lymphoid tissues. After several generations RAEV will lyse, delivering high levels of synthesized antigen.

The parent strain *E. ictaluri* 2003/c presents a low oral $LD_{50}$ in channel catfish and also in Zebrafish (*Danio rerio*) followed by i.p injection. We have isolated J100 *E. ictaluri* from multiple passages in Zebrafish. J100 *E. ictaluri* presents a low $LD_{50}$ in Zebrafish (~$10^3$ CFU/ml), and is currently utilized as the parent strain for vaccine development. The $LD_{50}$ in catfish will be evaluated as well. We have identified *E. ictaluri* genes for the RAEV design from the *E. ictaluri* genome sequence (published in NCBI) by using Blastn and Blastp. The bath/oral RAEV design will consist of more than 2 non-auxotrophic, genetic modifications (deletions and/or insertions) with the exception of Δasd used for the balanced lethal system selected from the following: Δcrp-10; $\Delta P_{crp11}$::TT araC $P_{BAD}$ crp; Δfur-35; $\Delta P_{fur70}$::TT araC $P_{BAD}$ fur; $\Delta P_{insA40}$::TT araC $P_{BAD}$ insA; ΔwibT; Δgne-31; Δugd-11; ΔesrB70; ΔrelA50::araC $P_{BAD}$ lacI TT; ΔasdA02::TT araC $P_{BAD}$ c2; and $\Delta P_{murA60}$::TT araC $P_{BAD}$ murA. The GAPDH antigens from *E. tarda* and *E. ictaluri* have been sequenced, cloned and expressed in pET30a vector. We cloned GAPDH from *Flavobacterium* (TABLE A). We anticipate that the vaccine will trigger a potent protective immune response, without vaccine survival, either by bath or oral (feed) immunization (FIG. 6).

We developed the first balanced-lethal vaccine system for use in aquaculture using *E. ictaluri* by mutation of the asdA gene and $AsdA^+$ vectors (FIGS. 10-17). Using the balanced-lethal system, we created the first recombinant strain that secretes antigens (FIG. 4) and the presence of the $Asd^+$ plasmid complements the ΔasdA01 mutation to restore virulence in zebrafish and catfish hosts (FIG. 13).

Example 6

Construction and Evaluation of *E. ictaluri* Strains with Genetic Alterations to Result in a Suitable Host Strain to Deliver a Protective Antigen Introduction. As we described above, *E. ictaluri* host construction has begun for suicide vector constructions. As we are finishing the suicide vector constructions, the genetic modification of *E. ictaluri* is carried out in parallel.

Figure 18:
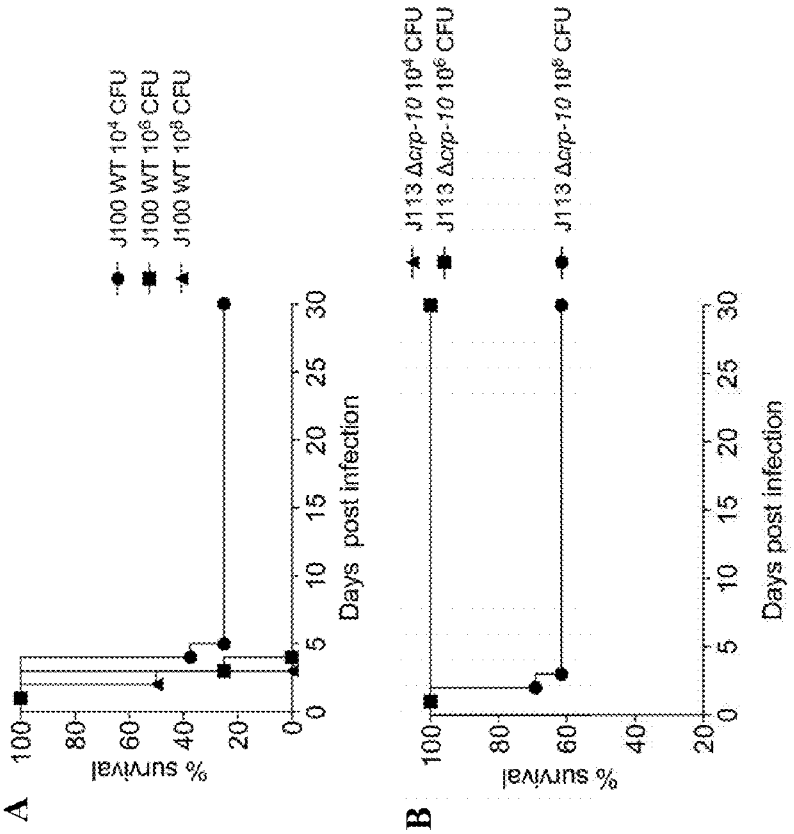
FIG. 18 depicts an illustration of Zebrafish survival post I.M. infection with (A) J100 *E. ictaluri* 2003/C wild type (n=50 per dose) and (B) J113 *E. ictaluri* Δcrp-10 (n=15 per dose). The experiments were done two times independently for each strain.
Figure 20:
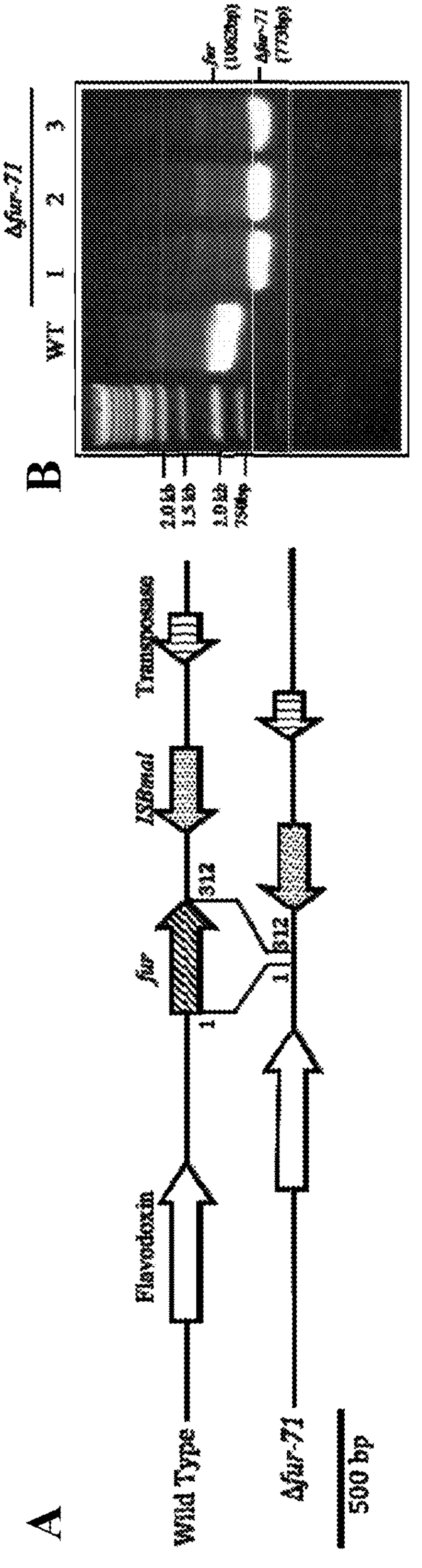
FIG. 20 depicts an illustration of deletion of (A) *E. ictaluri* fur gene and (B) genotype verification of *E. ictaluri* Δfur-71 mutation.
Figure 21:
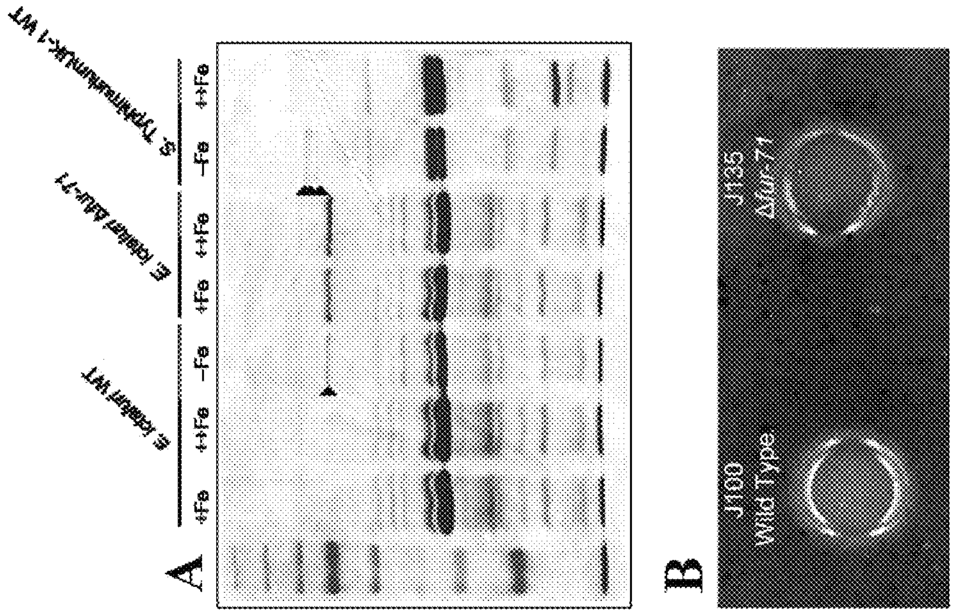
FIG. 21 depicts an illustration of (A) outer membrane proteins up-regulated in the absence of iron and by the *E. ictaluri* Δfur-71 mutant strain in comparison with *S. Typhimurium* χ3761 and (B) growth on CAS plates of *E. ictaluri* wild-type J100 and *E. ictaluri* Δfur-71 mutant J135.
Figure 22:
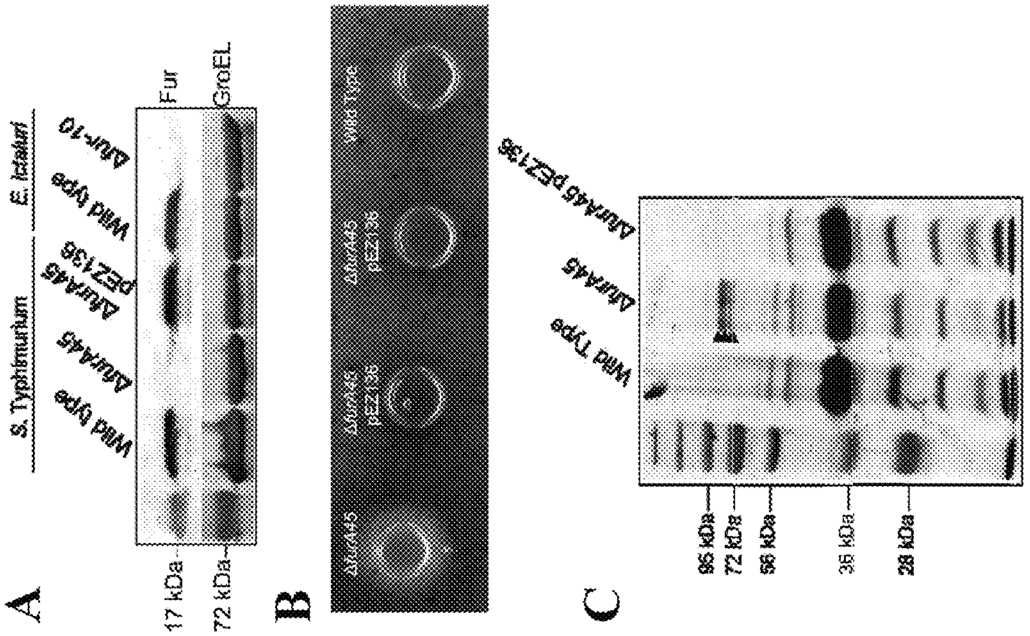
FIG. 22 depicts an illustration of deletion and complementation of *S. enterica* fur mutation by *E. ictaluri* fur gene cloned in pEZ136. (A) Synthesis of Fur verified by western blot analysis. (B) CAS phenotype. C. Outer membrane profile.
Figure 24:
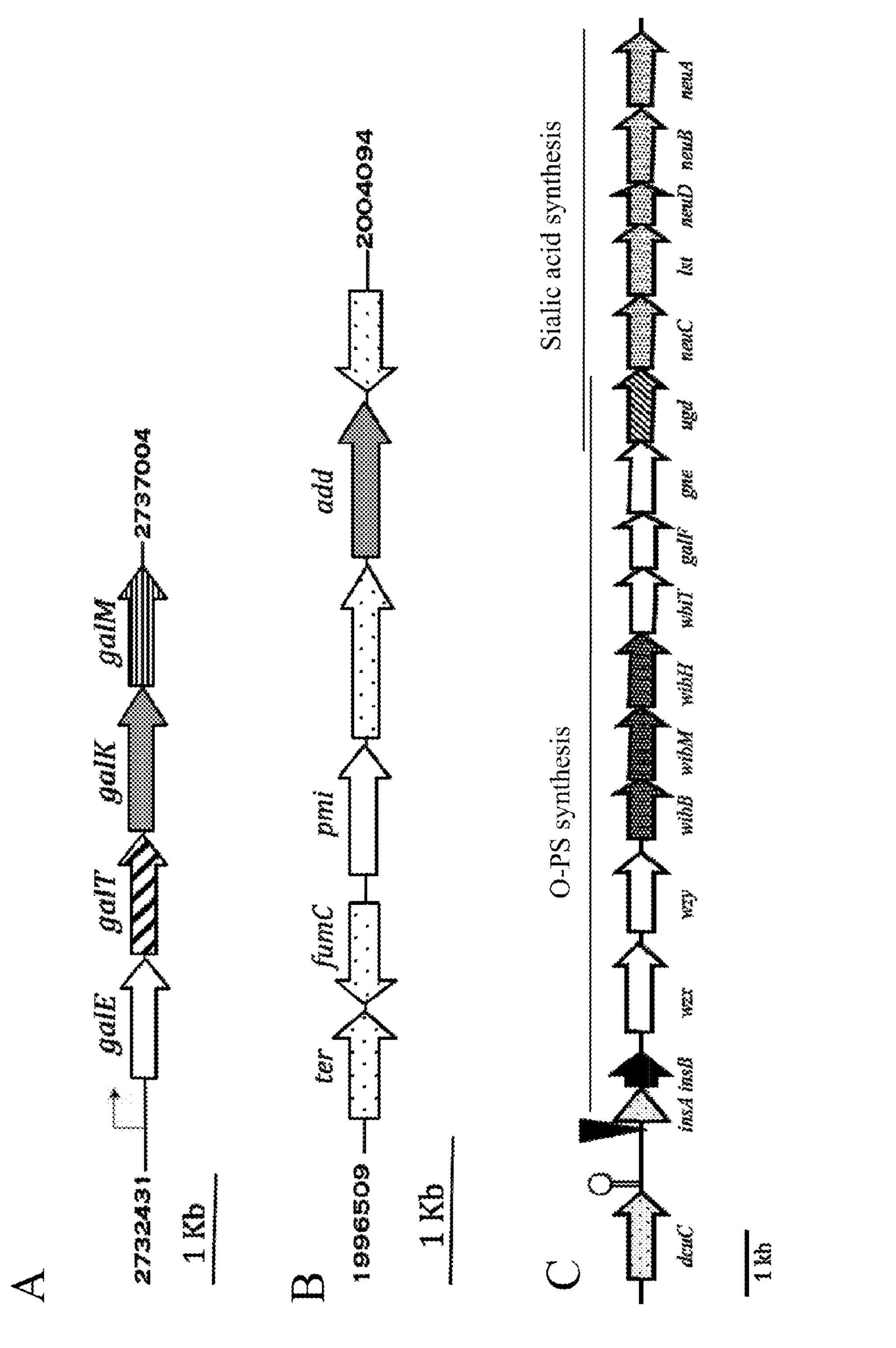
FIG. 24 depicts an illustration of deletion of: (A) Galactose utilization genes; (B) Phospho-mannose isomerase gene (pmi); (C) Lipopolysaccharide and sialic acid gene cluster.
Figure 25:
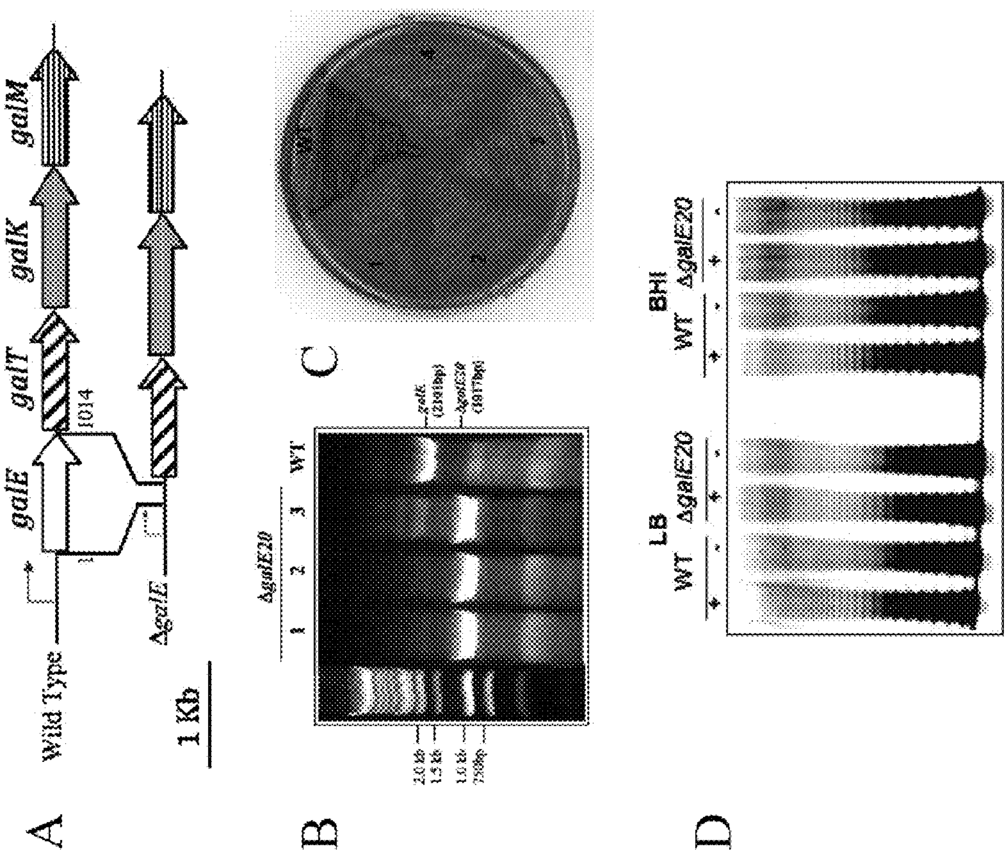
FIG. 25 depicts an illustration of: (A) *E. ictaluri* ΔgalE20 deletion map; (B) Genotype verification of *E. ictaluri* ΔgalE20; (C) Phenotype of *E. ictaluri* ΔgalE20 mutants (1-4) and *E. ictaluri* wild-type on MacConckey agar supplemented with 1% of galactose; (D) LPS profile of *E. ictaluri* ΔgalE20 mutants in presence and absence of galactose.
Figure 26:
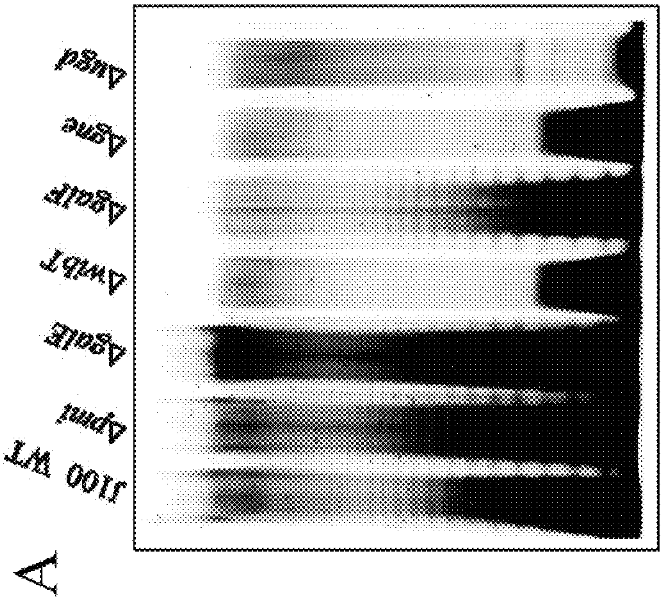
FIG. 26 depicts an illustration of (A) LPS profiles of *E. ictaluri* O-PS single mutants.
Figure 27:
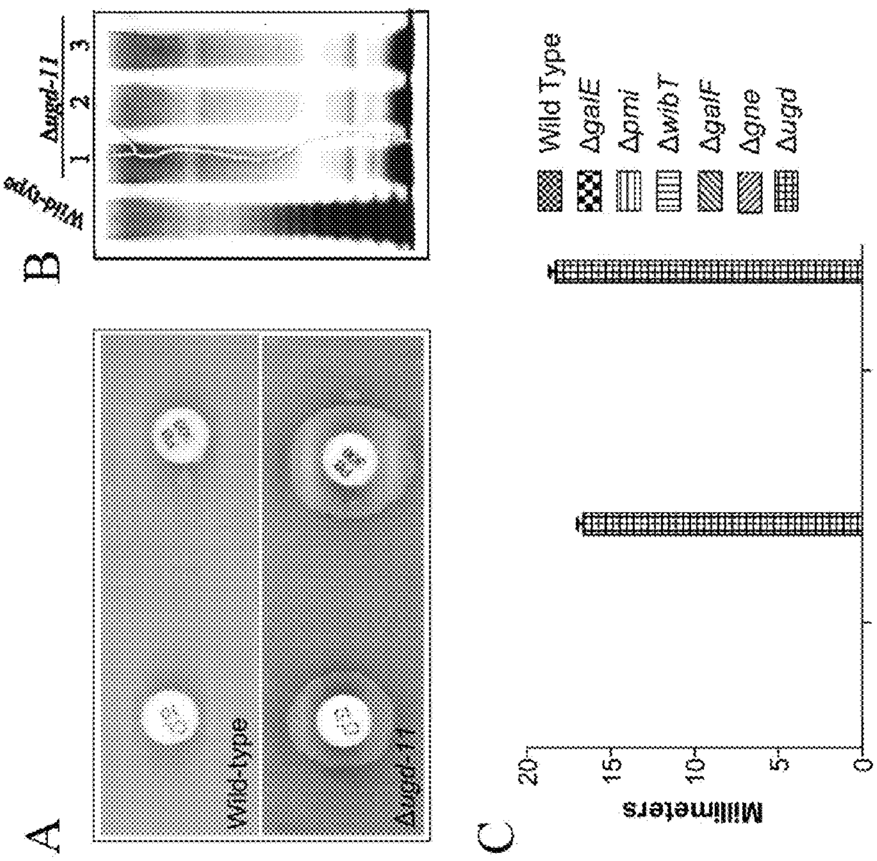
FIG. 27 depicts an illustration of: (A) sensitivity to colistin sulphate and polymixyn B of *E. ictaluri* Δugd-11 by using sencidisks. The strain were grown in BHI agar plates; (B) LPS profile of *E. ictaluri* Δugd-11; (C) Antibiogram profile of O-PS mutants of *E. ictaluri*
Figure 28:
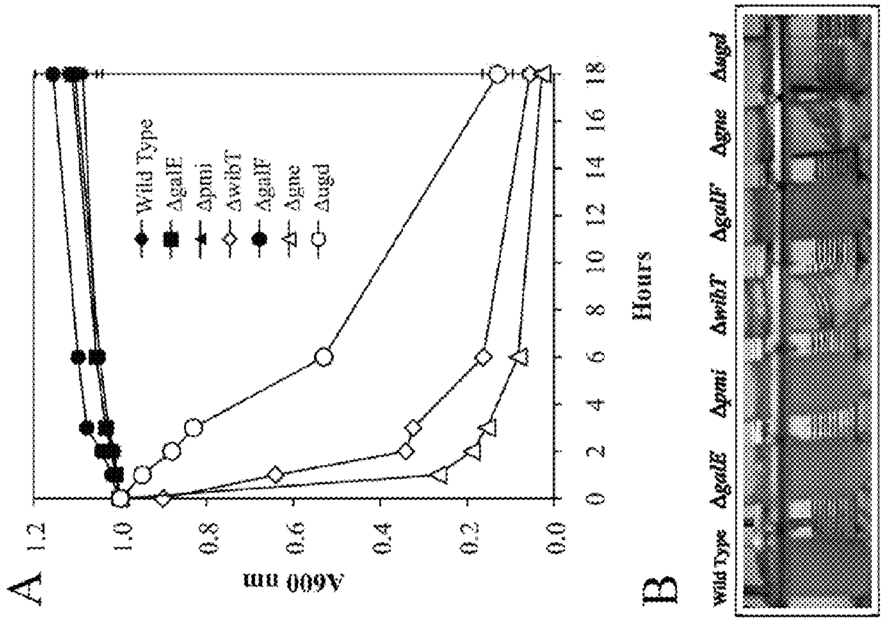
FIG. 28 depicts an illustration of: (A) auto-agglutination and precipitation of O-PS mutant strains grown in BHI at 28° C. ΔwibT, Δgne and Δugd presented auto-agglutination and precipitation; (B) Auto-agglutination after 18 h of static incubation of O-PS mutant strains.
Figure 29:
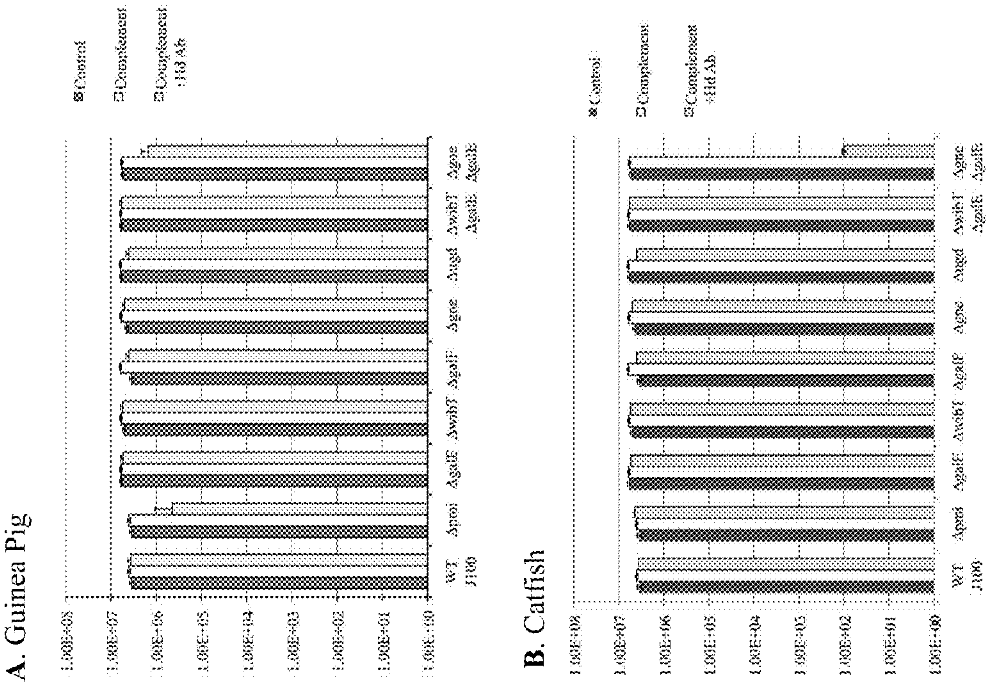
FIG. 29 depicts an illustration of sensitivity to complement and activation of complement from guinea pig and catfish against *E. ictaluri* O-PS mutant strain
Figure 30:
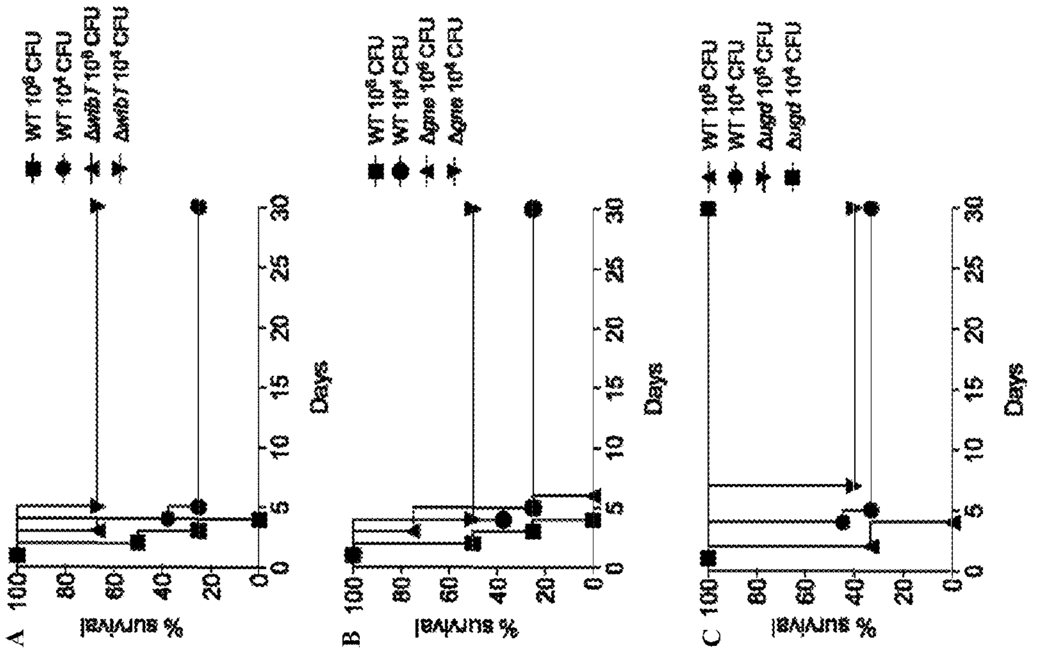
FIG. 30 depicts an illustration of Zebrafish survival post I.M. infection with (A) J100 *E. ictaluri* 2003/C wild type (n=50 per dose) and *E. ictaluri* ΔwibT (n=10 per dose); (B) J100 *E. ictaluri* 2003/C wild type (n=50 per dose) and *E. ictaluri* Δgne-31 (n=10 per dose); (C) J100 *E. ictaluri* 2003/C wild type (n=50 per dose) and *E. ictaluri* Δugd (n=10 per dose). The experiments were done two times independently for each strain.
Figure 31:
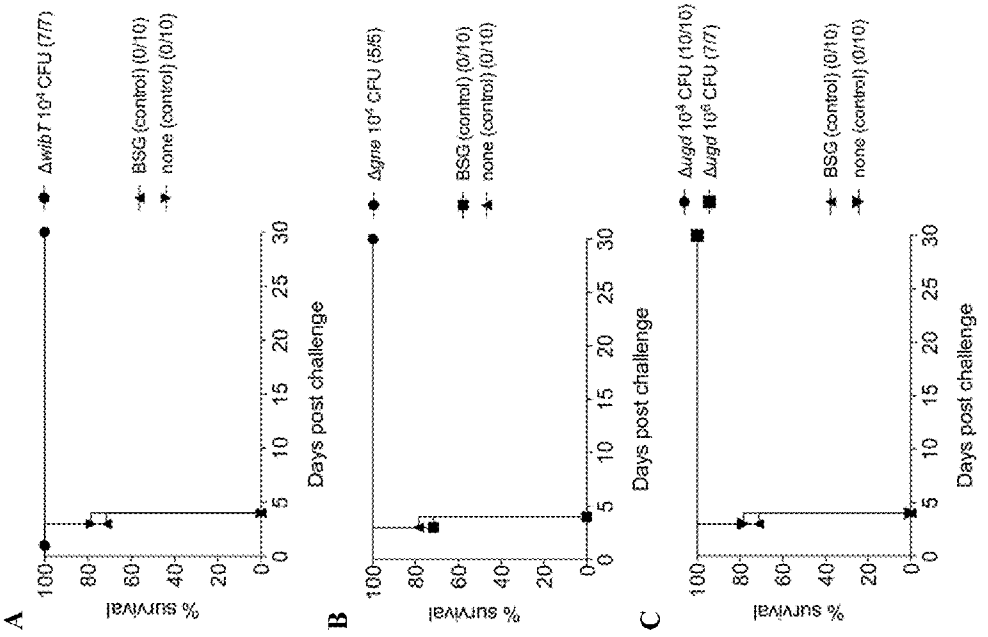
FIG. 31 depicts an illustration of zebrafish survival post I.M. challenge with $10^5$ CFU J100 *E. ictaluri* 2003/C wild type, 4 weeks post immunization independently with (A) ΔwibT, (B) Δgne, or (C) Δugd. Two control groups were utilized, BSG injected and non-infected or injected.

Construction of *E. ictaluri* vaccine host strain. We already started the construction of the regulated delayed attenuation phenotype in *E. ictaluri* by introducing $\Delta P_{crp11}$::TT araC $P_{BAD}$ crp, $\Delta P_{fur70}$::TT araC $P_{BAD}$ fur, and LPS control through gne-25 or $\Delta P_{insA40}$::TT araC $P_{BAD}$ insA. Additionally, deletion of the transcriptional factor esrB70 were evaluated for attenuation (FIG. 32). Also the wibT, gne and ugd genes were evaluated for LPS control, attenuation (FIG. 30) and immune protection to challenge (FIG. 31). We anticipate that LPS and IROMPs are the key virulence factors to regulate to obtain a functional regulated delayed attenuation that will trigger induction of a potent immune response, like single mutants (FIG. 31). Regulation of crp and deletion of esrB are added as extra measures of safety (FIGS. 18 and 32). We will validate the complete avirulence of the constructed strains by an i.p. injection in 2-month-old fish and by bath inoculation in 10-day post hatch fish. The regulated delayed antigen synthesis and balanced-lethal vector-host system will require introducing the ΔrelA50::TT araC $P_{BAD}$ lacI TT and ΔasdA02::TT araC $P_{BAD}$ c2 deletion-insertion mutations. We identified the *E. ictaluri* relA gene and we are currently replacing this gene with the improved TT araC $P_{BAD}$ lacI cassette. LacI expression will be evaluated in the absence and presence of arabinose by routine western blot analysis using rabbit anti-LacI antibody. The balanced-lethal system has been developed in *E. ictaluri* and we are currently combining this system with the programmed regulated delayed cell lysis system, which requires the regulated synthesis of C2 repressor. We are currently replacing asd by an improved TT araC $P_{BAD}$ c2 cassette. The synthesis of C2 will be evaluated by routine western blot analysis using rabbit anti-C2 antibody. The regulated programmed cell lysis phenotype will require the replacement of P murA by araC $P_{BAD}$, thus murA expression will be controlled by the presence of arabinose. The suicide vector to attain this objective is currently under construction.

Discussion. The regulated delayed attenuation constructions provide several alternatives. We are confident that over expression of IROMPs (FIGS. 19-23) and under expression of LPS O-antigen (FIG. 30) will achieve an excellent attenuation (FIG. 31) or delayed attenuation. The presence of the $\Delta P_{crp11}$::TT araC $P_{BAD}$ crp mutation provides both attenuation and acts as a second means to shut off virulence gene expression under $P_{BAD}$ control since transcription requires both arabinose and the Crp protein. We expect that the Δgne-25 or Δugd deletions will permit regulation of LPS O-antigen and core synthesis by the presence or absence of galactose in the media. Alternatively, the LPS O-antigen gene cluster will be controlled by arabinose through inclusion of the $\Delta P_{insA40}$::TT araC $P_{BAD}$ insA mutation. The structurally essential genes, such as asdA and murA, and regulatory control genes, such as relA, are highly conserved. Therefore the balanced-lethal system (FIGS. 10-13), regulated delayed antigen synthesis, and regulated programmed cell lysis development will rely on our genetic expertise to modify these genes. The basic expected genetic construction for RAEV is $\Delta P_{fur70}$::TTaraC $P_{BAD}$ fur $\Delta P_{crp11}$::TT araC $P_{BAD}$ crp; Δgne-25 or Δugd or $\Delta P_{insA40}$::TT araC $P_{BAD}$ insA, ΔrelA50::araC $P_{BAD}$ lacI TT, ΔasdA02::TT araC $P_{BAD}$ c2 and $\Delta P_{murA60}$::TT araC $P_{BAD}$ murA.

Example 7

GAPDH Cross Protection

Introduction. As we described above, GAPDH has been used as a monovalent injectable vaccine, because it has the ability to stimulate a protective immune response against several pathogens. GAPDH from *E. tarda* also confers cross-protective immunity to *Edwardsiella* and *Vibrio*. Therefore, we will evaluate GAPDH from *Edwardsiella* and *F. columnare* strains as cross-immune protective antigens.

Figure 8:
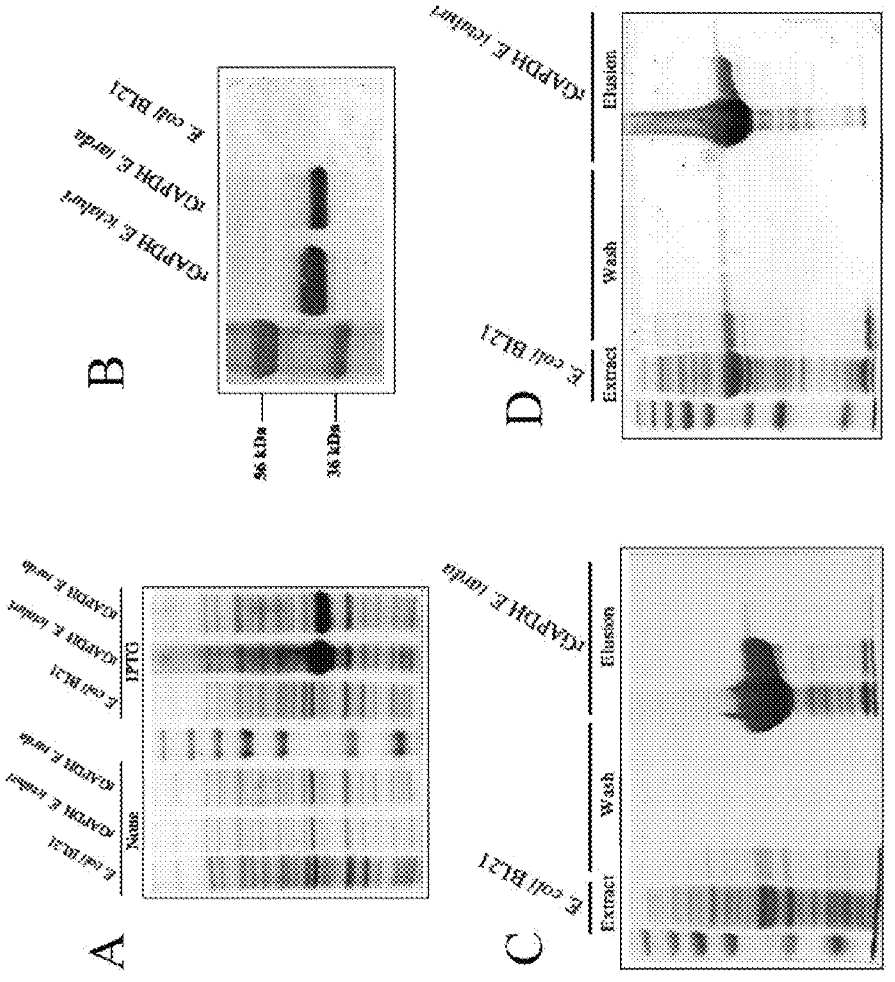
FIG. 8 depicts an illustration of (A) the synthesis of rGAPDH from *Edwardsiella* in *E. coli*; (B) detection of His-tag by western blot; (C) the purification of *E. tarda* rGAPDH and (D) *E. ictaluri* rGAPDH.

Cloning and purification of GAPDH. Using the *E. tarda* gapA gene and *F. psychophilum* gapA gene bank sequences, we have amplified, sequenced and cloned the gapA gene form *E. ictaluri* and *E. tarda* (FIG. 7 and FIG. 8). We are currently sequencing the gapA gene from *F. columnare*. GAPDH protein from these three pathogens will be purified from pET vectors (Table A) to yield His-tagged GAPDH. The purified proteins will be used for mouse or rabbit anti-GAPDH antibody production and fish immunizations.

Evaluation of cross-immune protection. 2-month-old fish will be immunized i.p. with GAPDH from these different pathogens and boosted 2 weeks after the primary immunization. The humoral immunogenicity in blood and skin will be evaluated by ELISA. After eight weeks, the animals will be challenged by bath with *E. ictaluri, E. tarda* and *F. columnare* individually. We will thus determine which GAPDH induces the highest levels of homologous and heterologous protection.

Co-localization of GAPDH in the bacterial cell. Different strains of *E. ictaluri, E. tarda* and *F. columnare* will be grown in the absence and presence of glucose (additional conditions will be tested as well). The cells will be fractionated by osmotic shock and the presence in the different cellular fractions will be analyzed by western blots. RpoD and/or GroEL monoclonal antibodies (Neoclone), which cross-react with these bacterial strains, will be used as a control. Electron microscopy and immuno-gold cytochemistry will be used to visualize the localization of GAPDH in the cell. This procedure will be done in the Electron Microscopy Laboratory of the School of Life Sciences at Arizona State University.

Figure 34:
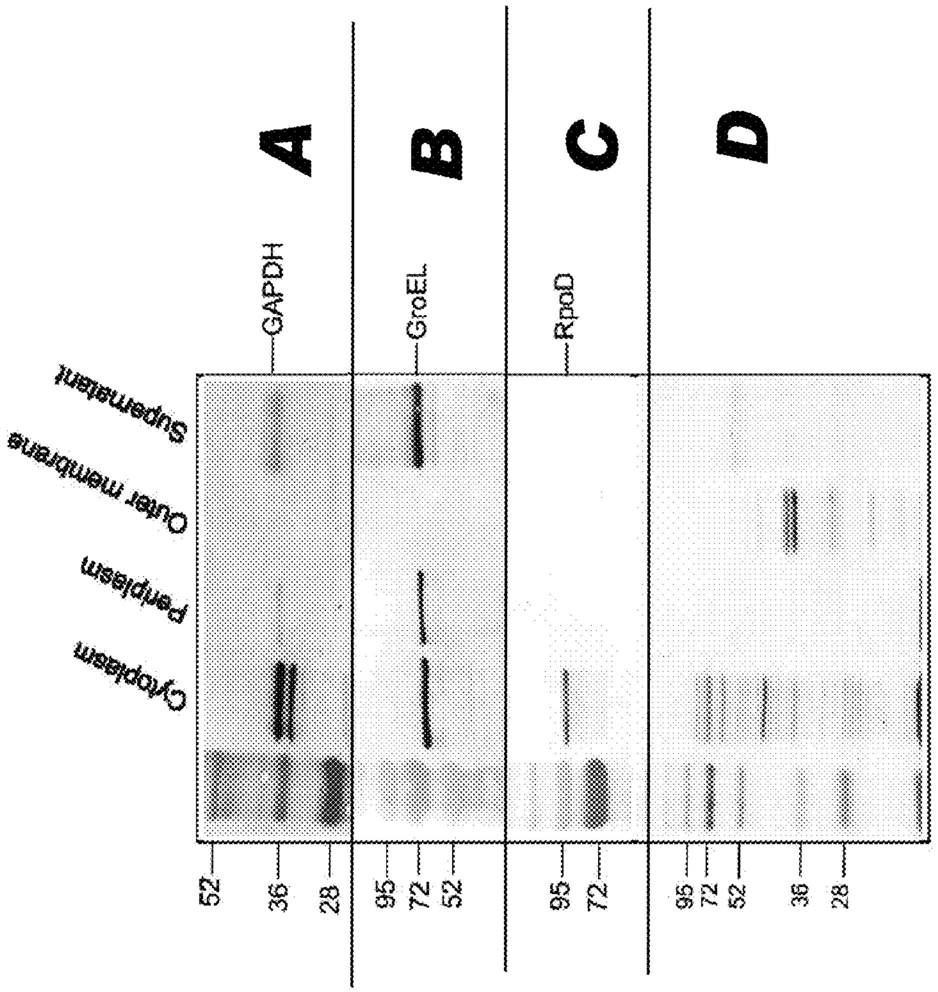
FIG. 34 depicts an illustration of (A) GAPDH and (B) GroEL secretion in *E. ictaluri*. (C) RpoD was used as cytoplasm protein control; (D) Commassie blue of the bacterial cell fractionation.

Discussion. GAPDH has several families of conserved proteins. The prokaryotic GAPDH in Gram positive bacteria is secreted and acts as a virulent factor by suppression of the immune system, serves as a transferrin-binding protein, and plasminogen-binding protein. In Gram negative bacteria, GAPDH only has been used as a protective antigen. We expect to find novel functions for GAPDH in gram negative bacteria, which will help to answer why a predicted cytoplasmic protein is immunogenic. We expect to find variations between *Edwardsiella* and *F. columnare* GAPDHs. We will chose the GAPDH that has the best cross-immune protection to clone the encoding sequence in the plasmid vector and be expressed in RAEV. If GAPDH from these organisms do not confer cross-immune protection, we will use GAPDH from *F. columnare* as an antigen to confer protection against *F. columnare*. We determined that GAPDH is secreted by *Edwardsiella, Flavobacterium* and *Vibrio* species (FIG. 34). The N-terminal residues of each of these GAPDH sequences are conserved. Hence, we predict that the N-terminal (N-peptide) may confer immune protection to all three species.

Example 8

Plasmid Vector Construction and Antigen Delivery

Introduction. As described above the balanced-lethal system was successfully developed by using several plasmid vectors that have been designed for antigen delivery through type II secretion. The plasmid vector pYA3681 designed to deliver antigens through regulated programmed cell lysis described above will be modified for antigen secretion and lysis antigen delivery.

Antigen cloning and evaluation of antigen delivery. The DNA sequence encoding GAPDH will be cloned as a fusion into the plasmid vector pYA3493 (Table A), which possesses the N-terminal segment of the bla-SS. Functional secretion of GAPDH will initially be evaluated in J112 *E. ictaluri* ΔasdA01 in the presence and absence of IPTG (1 mM). The cloned fusion sequence will then be subcloned into the pYA3681 regulated delayed lysis vector. The final plasmid vector will be evaluated in the *E. ictaluri* bacterial vector for secretion in different concentrations of arabinose and for a release of a bolus of antigen after growth in the absence of arabinose.

Discussion. We expect that GAPDH antigen will be over secreted trough the type II secretion system present in *E. ictaluri*, when is cloned in $AsdA^+$ vectors. If we observe that the antigen has difficulties being secreted, we will use the N-peptide of GAPDH. If we observe that GAPDH or the N-peptide cannot be secreted from *E. ictaluri* when is cloned in $AsdA^+$ vectors, we will use the programmed cell lysis as the main delivery strategy.

Example 9

Evaluation of Programmed Cell Lysis for Biological Containment of RAEV

Introduction. As we described above, regulated programmed cell lysis relies on the presence/absence of arabinose. Therefore the objective here is to evaluate the RAEV ability to grow in the nutritional components that are likely to be encountered by RAEV when used to immunize catfish (FIG. 1).

Evaluation of programmed cell lysis in vitro. To evaluate the predicted arabinose-dependent lysis, the strain will be inoculated with and without arabinose into several media containing nutritional components that are likely to be encountered by a vaccine strain, including 1% fish food, 1% catfish meat, and 1% catfish internal-organs in minimal medium (see FIG. 1). Evaluation of programmed cell lysis in vivo is described below.

Discussion. We expect that RAEV would grow only in the presence of arabinose. We are confident that RAEV will behave in catfish tissues in presence and absence of arabinose, as has been determined for *Salmonella* in chickens, mice, catfish, Zebrafish and trout tissues (FIG. 1).

Example 10

Evaluate Abilities of the RAEV Strain to Colonize Lymphoid Tissues in Channel Catfish, Exhibit Programmed Cell Lysis, and Induce Protective Immunity to *Edwardsiella* and *F. columnare* Challenges Introduction. The objective of these in vivo studies is to accurately evaluate the attributes of the vaccine construction. Many of the testing strategies and protocols have been described in preceding sections.

In vivo evaluation for colonization and persistence. After full in vitro characterization of the bacterial host strain, the plasmid vector, and the recombinant host-vector recombinant strain, we will examine the ability of the RAEV grown in BHI at 28° C. with 0.05% arabinose and 0.05% galactose (if it is required for LPS synthesis) to $OD_{600nm}$ of ~0.85 to colonize intestines, gills, kidney, liver and spleen. 2-month-old fish will be inoculated by bath ($10^7$ CFU/ml) and orally ($10^9$ CFU/ml). We will determine the CFU/g of tissue for each tissue and time. We will use different media supplemented with arabinose, galactose and DAP, to facilitate recovery of cells. Three tissue samples from three different animals will be obtained at 3, 7, 14, 21, 35, and 42 days post immunization. These studies will reveal the time for commencement of cell lysis of RAEV. Thus, the vaccine strain is rigorously evaluated for complete biological containment with no survivors in tissues and in intestinal continents. We will also sample the water in which fish are swimming for detection of any surviving vaccine strain.

Immunogenicity evaluations. RAEV deemed to have satisfactory performance criteria will be analyzed for capacity to elicit appropriate immune responses to GAPDHs and *E. ictaluri* antigens (OMP and LPS). Groups of five 2-month-old fish will be inoculated by bath ($10^7$ CFU/ml) and orally ($10^9$ CFU/ml) immunized with RAEV grown in BHI at 28° C. with 0.05% arabinose and 0.05% galactose (if it is required for LPS synthesis). Blood serum and skin will be assessed by ELISA. We will monitor antibody responses to GAPDHs, *E. ictaluri* LPS, and a mixture of *E. ictaluri* OMPs and IROMPs obtained from *E. ictaluri* $\Delta P_{fur70}$::TT araC $P_{BAD}$ fur gne-25 mutant grown in presence and absence of arabinose and from other *E. ictaluri* and *E. tarda* strains growing in iron limiting conditions.

Evaluation of cross-protective immunity. For *E. ictaluri, E. tarda* and *F. columnare* challenges, groups of eggs and frys 10 days post hatch will be immunized by bath with $10^7$ CFU/ml of RAEV. Hatching and frys survival will be monitored. A second RAEV immunized group will be orally boosted three weeks post immunization. At eight weeks post immunization, the fish will be bath challenged with *E. ictaluri, E. tarda*, and *F. columnare* independently. Fish will be monitored daily for mortality. Protection against *E. ictaluri* and *F. columnare* will be monitored in 5 fish euthanized 5 days after challenge and in 5 fish euthanized 14 days after challenge with determination of quantitative bacterial titers in the fish body (small frys) or specific tissues.

Discussion. We anticipate success in developing the first recombinant bacterial vaccine to protect catfish against *E. ictaluri* and *F. columnare* infections that also will enhance food safety by preventing *E. tarda* infection. We also anticipate making discoveries during the course of these studies to enable additional improvements not described above to further ensure a successful outcome of these studies. When we identify a vaccine construction with the optimal combination of attributes: total attenuation with induction of no disease symptoms and no inhibitions of physiology or growth, ability to induce high cross-protective immunity to all challenge organisms, and inability to persist in immunized fish or survive if excreted, we will do multiple tests to obtain statistically significant results.

Materials and Methods for the Above Examples

Bacterial strains, plasmids and culture conditions. The bacterial strains and plasmids are listed in Table A. Bacteriological media and components are from Difco (Franklin Lakes, N.J.). Antibiotics and reagents are from Sigma (St. Louis, Mo.). LB broth (tryptone, 10 g; yeast extract 5 g; NaCl, 10 g; $ddH_2O$, 114 Brain Heart Infusion (BHI), Trypticase Soy Broth (TSB), and FCGM media (tryptone, 8.0 g; yeast extract, 0.8 g; NaCl, 5.0 g; $CaCl_2$, 1.0 g; $SrCl_2.6H_2O$, 0.74 g; sodium citrate, 1.5 g; $ddH_2O$ 1 L; pH 7.0) are used as complex media for bacteria propagation. MacConkey agar, FCGM agar and Shotts & Waltman agar supplemented with D-lactose (0.5% wt/vol), L-arabinose (0.05% wt/vol), D-maltose (0.02% wt/vol) or L-galactose (0.05% wt/vol), are used to count bacteria from fish tissues. Nutrient broth, which is devoid of arabinose and mannose, and minimal media will also be used. When required, the media are supplemented with 1.5% agar, colistin sulphate (Col; 12.5 μg/ml), ampicillin (Amp; 50 μg/ml), chloramphenicol (Cm; 25 μg/ml), kanamycin (Km; 50 μg/ml), or tetracycline (Tet; 12.5 μg/ml). Bacterial growth is monitored spectrophotometrically and/or by plating.

Molecular and genetic procedures. Methods for DNA isolation, restriction enzyme digestion, DNA cloning and use of PCR for construction and verification of vectors are standard. We use *E. coli* K-12 χ6097, χ6212, χ7213, and χ7232 for initial cloning (Table A). DNA sequencing analysis will be performed at nominal charge in the DNA sequencing laboratory of the School of Life Sciences at Arizona State University. All oligonucleotide and/or gene segment synthesis will be done commercially. Conjugation is used to transfer suicide vectors from the donor χ7213 to *E. ictaluri*. Plasmid constructs will be evaluated by DNA sequencing, ability to complement *S. Typhimurium* mutant strains, and for the ability to synthesized specific proteins. The protein synthesis will be evaluated by using sodium dodecyl sulfate-polyacrylamide gel electrophoresis (SDS-PAGE) and western blot analyses. His- and GST-tagged proteins have and will be produced and used to obtain anti-protein rabbit, mouse and/or fish antibodies for western blot analysis.

Strain construction and characterization. The RAEV strains will be constructed by defined unmarked deletion-mutations using suicide vectors and conjugation. The suicide vector will be conjugated from χ7213 *E. coli*. The counter selection will be performed on TSA agar plates supplemented with 10% sucrose and Col. Vaccine strains will be fully characterized before immunization studies. Lipopolysaccharide (LPS) profile will be evaluated by SDS-PAGE and visualized by silver staining, to make sure that we do not select rough variants. Plasmid profiles will be verified by alkaline lysis and agarose gel (0.5%) electrophoresis. Comparative growth analyses also will be conducted, since our objective is to have single and multiple mutant strains grow at almost the same rate and to the same density as the wild-type parental strains when grown under permissive conditions. The strains are also evaluated for biochemical patterns by using the API 20E (bioMériux, Marcy l'Etoile, France), metabolic attributes, and sensitivity to antibiotics and drugs. Molecular genetic attributes will be confirmed by PCR. Motility tests will be used to reveal presence or absence of flagella.

Cell biology. The ability of various constructed *E. ictaluri* strains to attach to, invade and survive in channel catfish ovary (CCO) cell lines and head kidney derived macrophages (HKDM) is quantified by established methods.

Animal experimentation. Channel catfish egg masses will be obtained from Arizona commercial producers and/or academic institutions with no history of ESC or columnaris outbreaks. Fingerling channel catfish, *I. punctatus*, will be acquired from commercial producers and/or academic institutions as well. Preliminary animal assays will be conducted in the Biodesign Institute vivarium at Arizona State University. Confirmatory assays with a larger quantity of animals will be conducted in the College of Veterinary Medicine, Mississippi State University and/or in Department of Fisheries and Allied Aquacultures at Auburn University. Certificate Specific Pathogen Free (SPF) adult catfish for primary cell line preparation will be acquired from academic institutions. The tanks are maintained with dechlorinated water at ~28° C., periodically tested for water quality. $LD_{50}$ and immunizations with the vaccine candidates will be conducted in fish of different ages. i.p. and bath inoculation will be used to evaluate complete attenuation of the mutant strains. Boosting immunization will be given one week (for 2 month old fish) or three weeks (for eggs and frys) post primary immunization. Oral immunization will be conducted in 2 month old fish. The fish will be deprived of food 6 h prior to inculcation and anesthetized with MS22 (100 mg/L; Sigma) for easy handling. Oral inoculation will predict immunization through the food, for further practical boosting immunization. Candidate vaccine strains will be quantitatively enumerated in various tissues (head kidney, liver, spleen, gills, and intestines) as a function of time after inoculation. Generally, five fish will be used per time point. Immunized fish (bath, and/or bath-oral boosted) will be challenged 6 weeks post inoculation by immersion exposure with $10^7$ CFU/ml of *E. ictaluri, E. tarda* and *F. columnare*. Euthanasia of fish will be performed by over dose of MS22 (500 mg/ml). The determination of $LD_{50}$ in zebrafish is performed as follows. Zebrafish infections were performed by the methodology described by Petri-Hanson et al. (2007) with modifications. The temperature of the water was 26±1° C., the fish were acclimated during the 2 weeks before experimentation. Adult zebra fish (average weight, 0.5 g) were sedated in 100 mg/L tricaine methanesulfonate (MS-222, Sigma), then injected intramuscularly (IM). Groups of zebrafish (typically 15 fish per group) were injected IM with 10 μl of the bacterial suspension ($10^3$-$10^9$ CFU) into each fish. 3/10-cc U-100 ultrafine insulin syringe with a 0.5-in.-long (ca. 1-cm-long) 29-gauge needle (catalog no. BD-309301; VWR) was used to inject the fish. Two sets of controls were used: fish that were injected with 10 μl of sterile phosphate-buffered saline containing 0.01% gelatin (BSG) and fish that were non injected. Moribund fish demonstrating clinical signs were euthanized and necropsied, and bacteria isolated. The fish were feed daily with TetraMin Tropical Fish Flake Feed twice daily. During the experiments, the fish were observed daily, and every other day water quality was monitored for pH and $NO_2$ with standards kits. The $LD_{50}$ was calculated by the method of Reed-Muench. Fish care and use was performed in accordance with the requirements of the Arizona State University, Institutional Animal Care and Use Committee.

Figure 9:
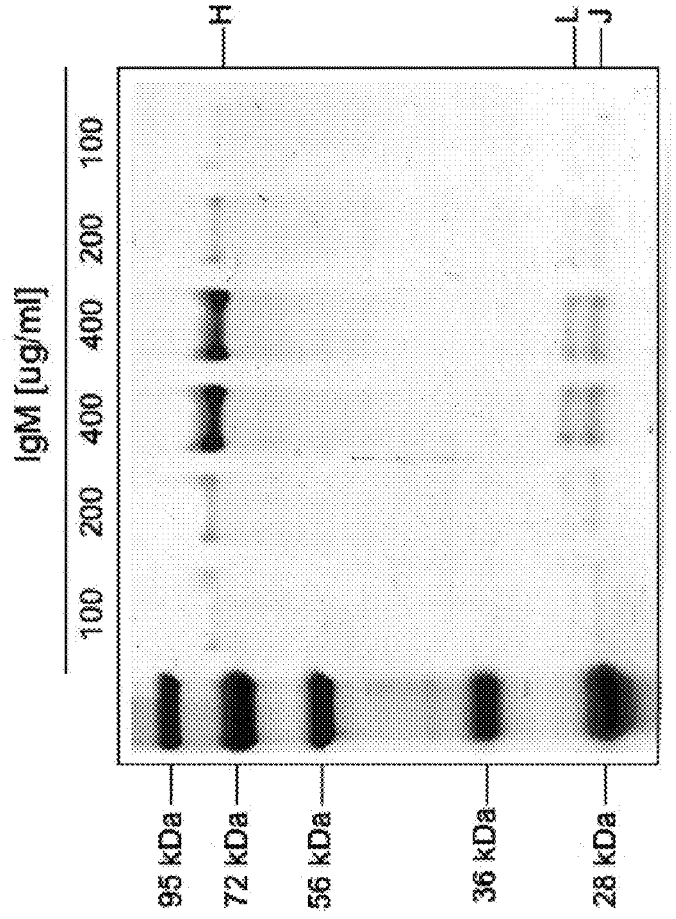
FIG. 9 depicts an illustration of IgM purification from catfish serum. H. heavy chain; L. light chain; J. J chain.
Figure 10:
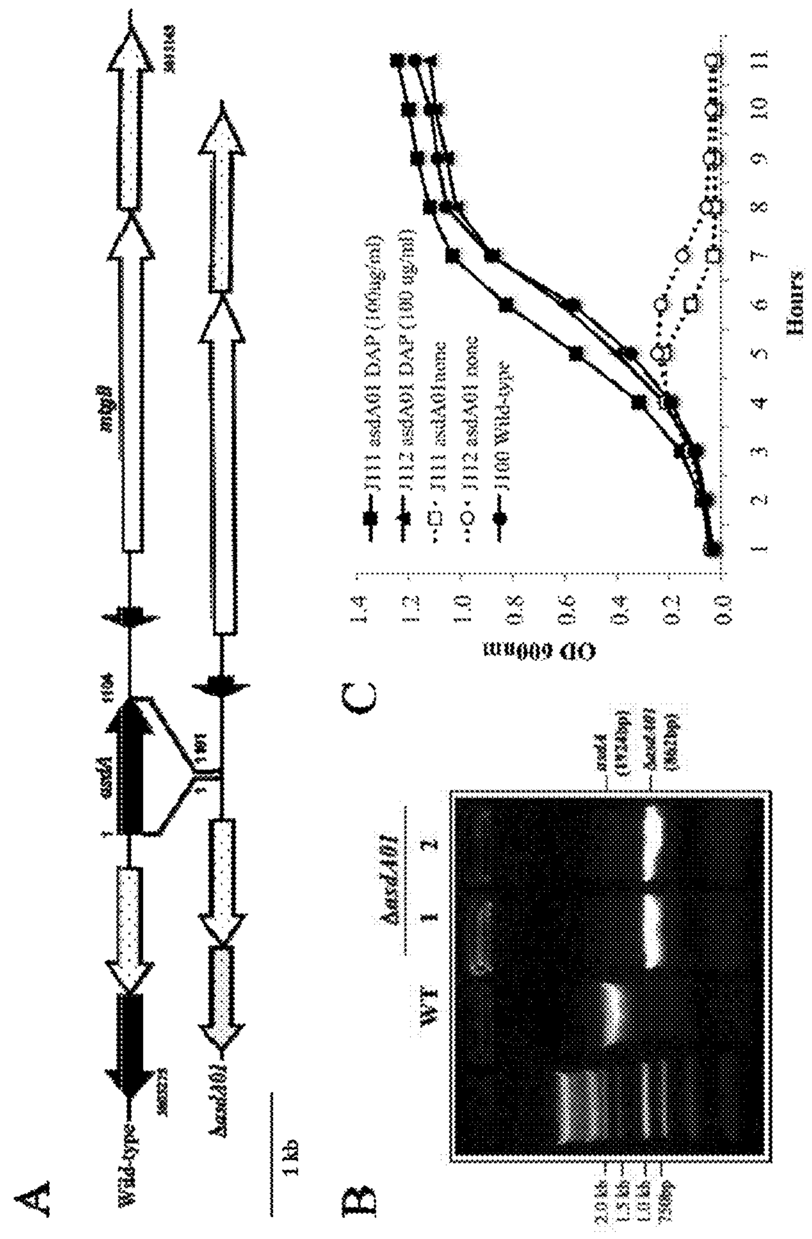
FIG. 10 depicts an illustration of deletion of asdA gene. (A) Deletion map; (B) Genotype verification of J112 ΔasdA01 by PCR; (C) Phenotype of J112 ΔasdA01 mutants.
Figure 11:
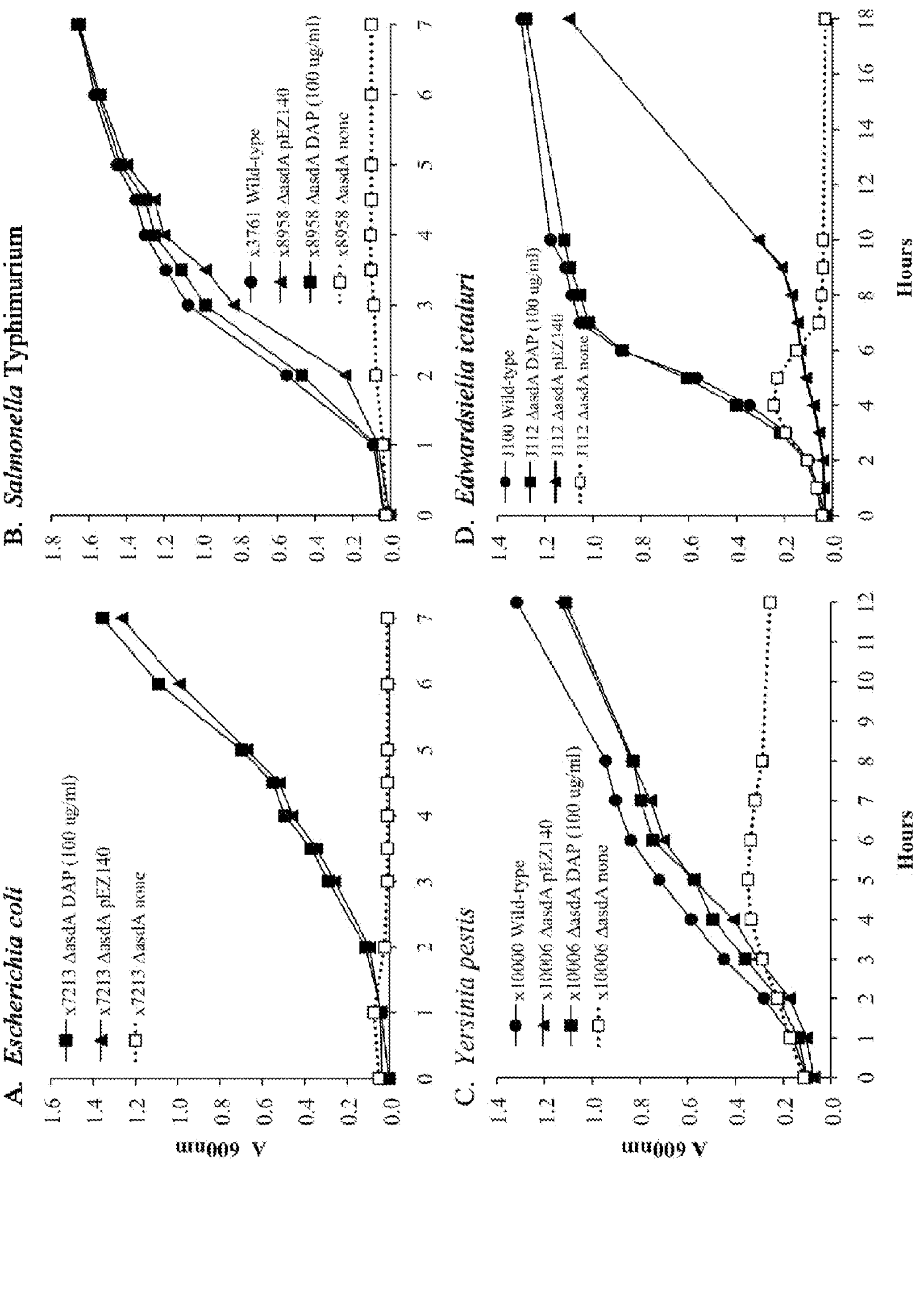
FIG. 11 depicts an illustration of complementation of asdA gene in other Enterobactericeae, including (A) *Escherichia coli*; (B) *Salmonella Typhimurium*; (C) *Yersinia pestis*; and (D) *Edwardsiella ictaluri*. (E) Promoter region of asdA gene in four bacterial species: *E. ictaluri; E. coli; S. Typhimurium*; and *Y. pestis*.
Figure 11:
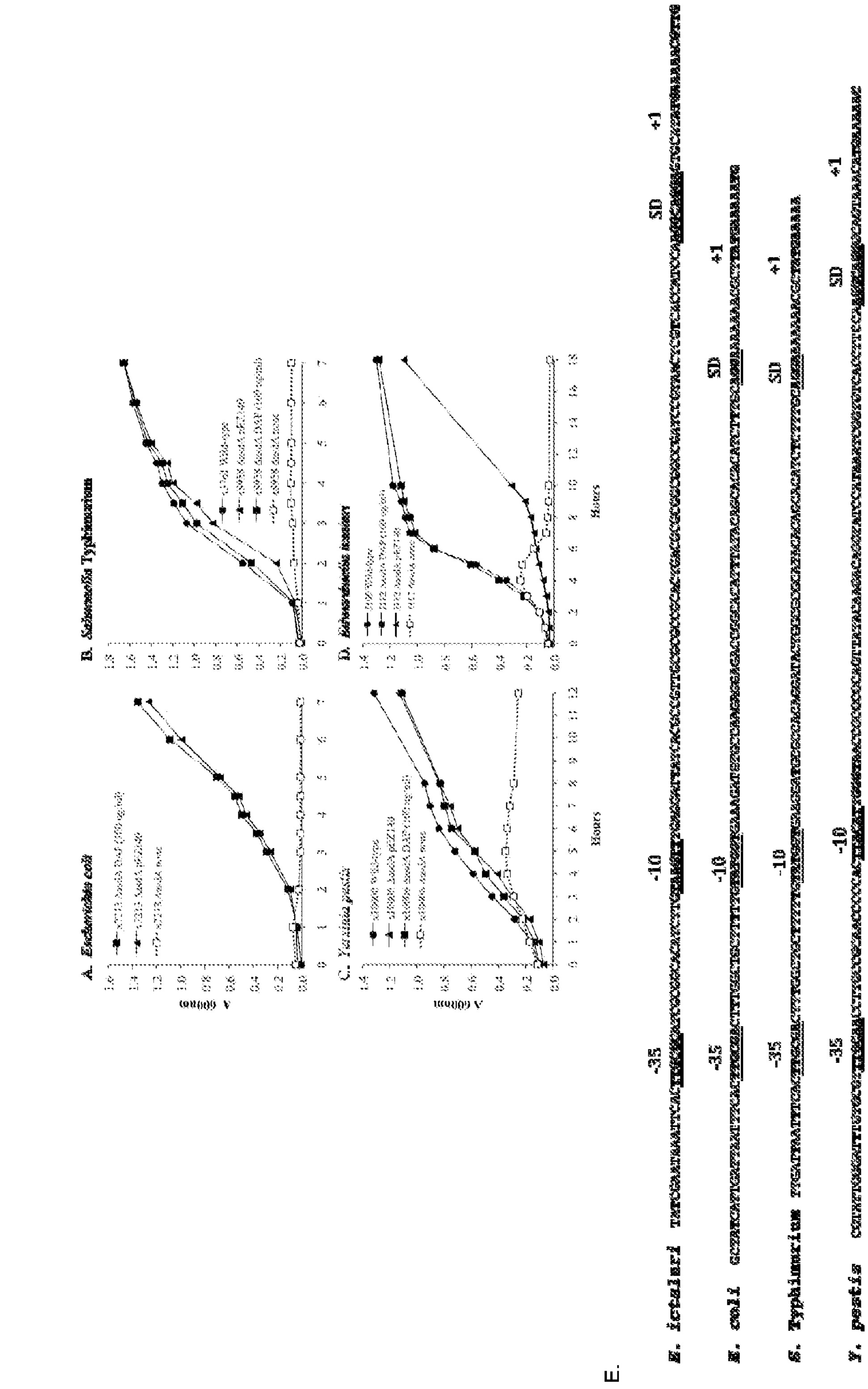
Figure 12:
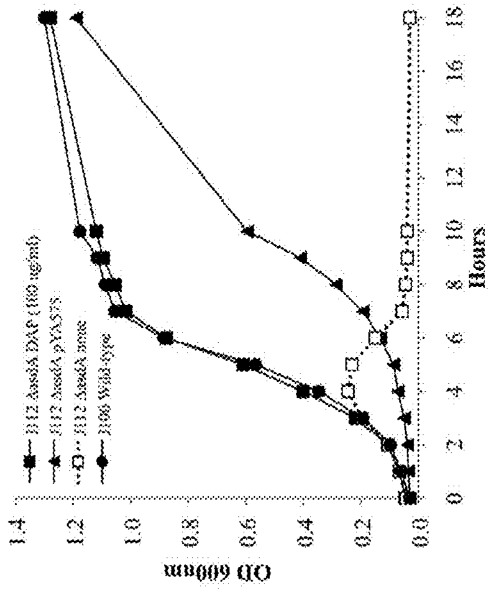
FIG. 12 depicts an illustration of *E. ictaluri* ΔasdA01 mutant complemented with a plasmid specifying asdB from *Streptococcus mutants.*
Figure 15:
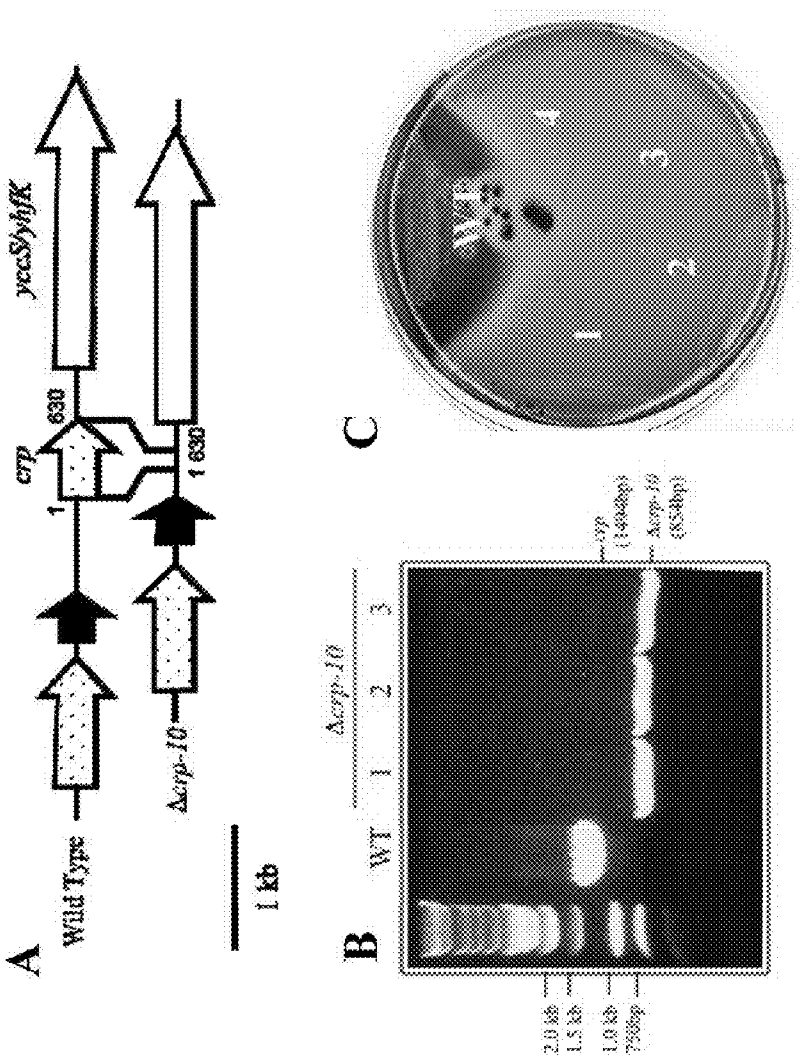
FIG. 15 depicts an illustration of deletion of crp gene. (A) Deletion map; (B) Genotype verification of J113 Δcrp-10 by PCR; C. Phenotype verification on MacConkey agar plates supplemented with 1% of maltose; WT: *E. ictaluri* J100 wild type; 1-4 *E. ictaluri* J113 Δcrp-10 mutants.
Figure 16:
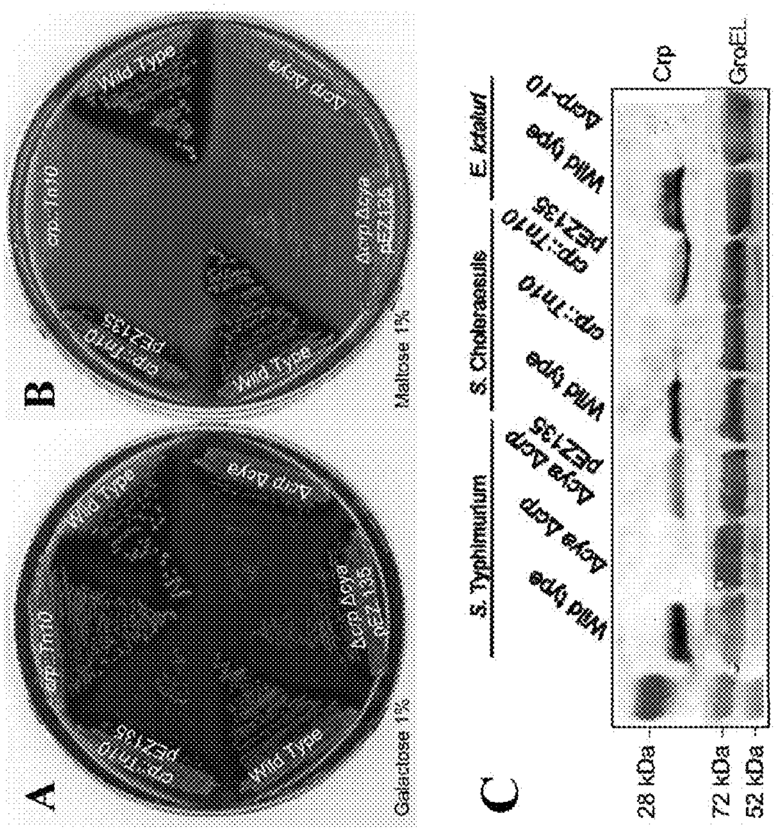
FIG. 16 depicts an illustration of complementation of *S. enterica* crp mutants by *E. ictaluri* crp cloned in pEZ135 and failure to complement crp cya double mutants. (A) Phenotype verification of functionality of *E. ictaluri* crp gene on MacConkey agar plates supplemented with galactose (control) and maltose; (B) Synthesis of Crp verified by western blot analysis.
Figure 17:
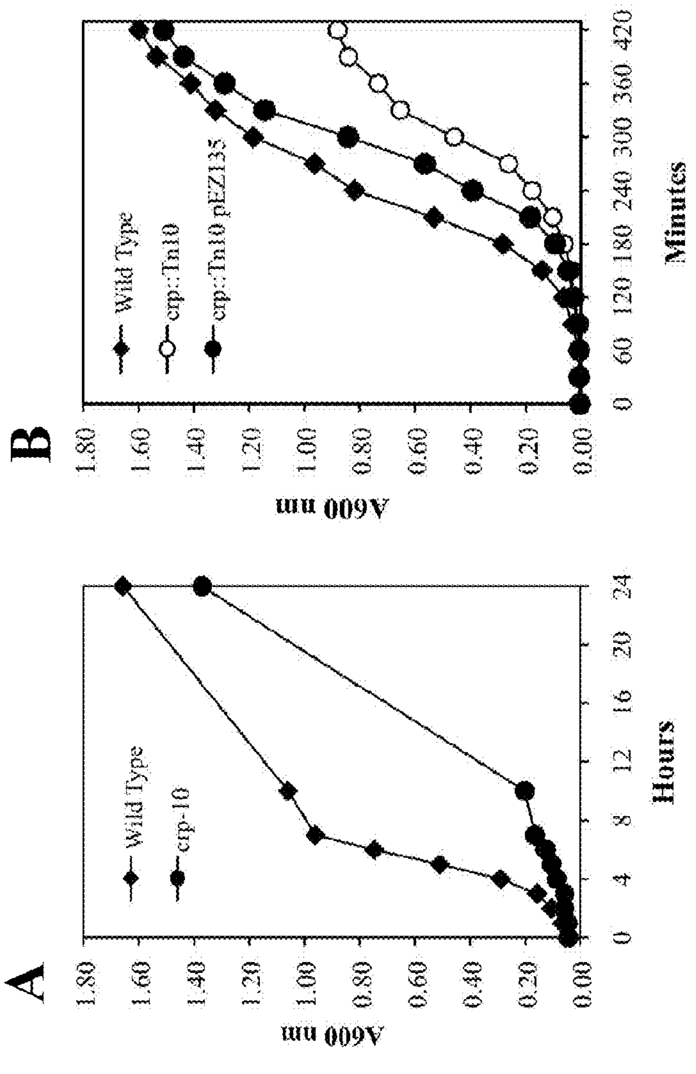
FIG. 17 depicts an illustration of: (A) growth of *E. ictaluri* J100 and J113 Δcrp-10 in BHI at 28° C. with aeration (180 rpm); (B) Growth of *S. Choleraesuis* χ3751 crp-773::Tn 10 and χ3751 crp-773::Tn 10 complemented with *E. ictaluri* crp cloned in pEZ135 in LB at 37° C. with aeration (180 rpm).

Production of anti-catfish IgM. Ten SPF adult catfish, 15 to 20 cm in length, will be used for blood extraction and IgM purification. Since catfish IgM titers are low, we will immunize catfish with bovine serum albumin (BSA) to amplify IgM titers. BSA in PBS at 1 mg/ml will be emulsified with a similar volume of Freund's complete adjuvant (FCA, Sigma). The emulsion will be administered i.p. Three similar boosters with incomplete Freund's adjuvant (FICA, Sigma) will be followed at 2 week intervals. After 8 weeks the catfish will be bled via venipuncture of the tail vessels and the serum will be harvested. IgM purification will be carried out using a chromatography column (ImmunoPure MBP and IgM purification, Price). Purity of the IgM will be evaluated by detection of the heavy chain (~70 kDa) and light chain (~24 kDa) in SDS-PAGE (FIG. 9). Purified IgM will be administered to a New Zealand rabbit to induce anti-catfish IgM production and to BALB/c mice for mouse anti-catfish IgM by using routine methods. The purified IgM will be emulsified with FCA to 150 μg/ml and administered subcutaneously, at multiple sites. Three boosters of similar concentration but in FICA following 3 week intervals will be performed. The blood will be collected from auricular artery and the serum will be harvested. The number of fish required was determined based on the blood volume needed.

Monitoring immune responses. i. Antigen preparation: We will make purified GAPDH antigens as His-tagged proteins from recombinant *E. coli*. We have prepared *E. ictaluri* OMPs and heat-killed extracts of the wild-type *E. ictaluri* 2003/c J101 strain. These antigens will be used as controls in western blots and immunoassays described below. ii. Immune response: For monitoring the humoral immune responses in catfish, we will use modified enzyme-linked immunosorbent assay (ELISA) to quantify the antibody titers to OMPs, LPS, and GAPDH antigens. Serum antibodies will be measured in blood collected from tail vessel bleeding and in fish skin. Serum and skin sections will be pooled. We will employ a doubling dilution method with the end point titer being the dilution giving $OD_{405nm}$ three times that for the reagent or unimmunized animal control.

Power analysis, animal number, and statistics. We performed a prior power analysis to determine the sample size for two independent groups (vaccinated v/s non-vaccinated) by using G*Power program. The egg number estimated was 91, we will use 100; the estimated number for frys and 2-month-old fish was 59, we will used 60 for final vaccine tests. The power for these tests was 0.85. We will perform a new power test from results of pilot experiments with RAEV.

Post experimentation, general linear model (GLM) procedure with Duncan's multiple range test is used to determine significant differences in percentage mortality between treatment groups (vaccinated and control) and between replicates (tanks) of these treatment groups. Significant differences are determined at $P<0.05$. Relative percent survival will be calculated. Tukey's test will be used for pairwise comparison of main effects, and a least square means procedure will be use for pairwise comparison of interaction effects.

What is claimed is:

1. A recombinant attenuated non-auxotrophic *Edwardsiella ictaluri* bacterium displaying regulated delayed attenuation, wherein the bacterium comprises a chromosomally integrated regulatable promoter operably linked to a nucleic acid sequence encoding an attenuation protein, such that transcription of the nucleic acid sequence encoding the attenuation protein occurs in a permissive environment, but ceases in a non-permissive in vivo environment.

2. The bacterium of claim 1, wherein the bacterium elicits an immune response against a fish pathogen other than *Edwardsiella* in a host.

3. The bacterium of claim 2, wherein the fish pathogen is a bacterial, viral, fungal or parasitic pathogen of fish.

4. The bacterium of claim 1, wherein the bacterium elicits an immune response against more than one fish pathogen.

5. The bacterium of claim 1, wherein the bacterium elicits an immune response to at least one of the pathogens selected from the group consisting of *Edwardsiella ictaluri, Edwardsiella tarda*, and *Flavobacterium columnare.*

6. The bacterium of claim 1, wherein the bacterium is capable of the regulated expression of at least one heterologous nucleic acid encoding an antigen, wherein the bacterium comprises at least one chromosomally integrated nucleic acid sequence encoding a repressor.

7. The bacterium of claim 1, wherein the bacterium is capable of regulated cell lysis.

8. The bacterium of claim 1, wherein the bacterium comprises a. at least one chromosomally integrated nucleic acid sequence encoding a repressor operably linked to a regulatable promoter, and b. a vector comprising at least one nucleic acid sequence encoding an antigen of interest operably linked to a promoter regulated by the repressor, such that the expression of the nucleic acid sequence encoding the antigen is repressed during in vitro growth of the bacterium, but the bacterium is capable of high level expression of the nucleic acid sequence encoding the antigen in a host.

9. The bacterium of claim 6, wherein the antigens are selected from the group consisting of GAPDH, LcrV or PspA-Rx1.

10. The recombinant bacterium of claim 1, wherein the bacterium comprises at least one mutation selected from the group consisting of $\Delta P_{crp11}$::TT araC $P_{BAD}$ crp; $\Delta P_{fur70}$::TT araC $P_{BAD}$ fur; $\Delta P_{insA40}$::TT araC $P_{BAD}$ insA or Δgne-25; ΔesrB80; ΔrelA50::araC $P_{BAD}$ lacl TT; ΔasdA02::TT araC $P_{BAD}$ c2; and $\Delta P_{murA60}$::TT araC $P_{BAD}$ murA.

11. The recombinant bacterium of claim 1, wherein the bacterium comprises at least three mutations selected from the group consisting of $\Delta P_{crp11}$::TT araC $P_{BAD}$ crp; $\Delta P_{fur70}$: TT araC $P_{BAD}$ fur; $\Delta P_{insA40}$::TT araC $P_{BAD}$ insA or Δgne-25; ΔesrB80; ΔrelA50::araC $P_{BAD}$ lacl TT; ΔasdA02::TT araC $P_{BAD}$ c2; and $\Delta P_{murA60}$::TT araC $P_{BAD}$ murA.

12. The recombinant bacterium of claim 1, wherein the bacterium comprises at least five mutations selected from the group consisting of $\Delta P_{crp11}$::TT araC $P_{BAD}$ crp; $\Delta P_{fur70}$::TT araC $P_{BAD}$ fur;$\Delta P_{insA40}$::TT araC $P_{BAD}$ insA or Δgne-25; ΔesrB80; ΔrelA50::araC $P_{BAD}$ lacl TT; ΔasdA02::TT araC $P_{BAD}$ c2; and $\Delta P_{murA60}$::TT araC $P_{BAD}$ murA.

13. The recombinant bacterium of claim 1, wherein the bacterium comprises at least six mutations selected from the group consisting of $\Delta P_{crp11}$::TT araC $P_{BAD}$ crp; $\Delta P_{fur70}$::TT araC $P_{BAD}$ fur; $\Delta P_{insA40}$::TT araC $P_{BAD}$ insA or Δgne-25; ΔesrB70; ΔrelA50::araC $P_{BAD}$ lacl TT; ΔasdA02::TT araC $P_{BAD}$ c2; and $\Delta P_{murA60}$::TT araC $P_{BAD}$ murA.

14. A vaccine composition, wherein the vaccine comprises a bacterium of claim 1.

15. The vaccine composition of claim 14, wherein the vaccine elicits a protective immune response against more than one fish pathogen.

16. The vaccine composition of claim 14, wherein the vaccine elicits an immune response against a fish pathogen other than *Edwardsiella* in a host.

17. The vaccine composition of claim 16, wherein the fish pathogen is a bacterial, viral, fungal or parasitic pathogen of fish.

18. A method of eliciting an immune response in a host, the method comprising administering a bacterium of claim 1 to the host.

19. The method of claim 18, wherein the immune response is a protective immune response.

* * * * *

SEQUENCE LISTING

```
<160> NUMBER OF SEQ ID NOS: 7

<210> SEQ ID NO 1
<211> LENGTH: 329
<212> TYPE: PRT
<213> ORGANISM: Edwardsiella ictalrui

<400> SEQUENCE: 1

Met Thr Ile Lys Val Gly Ile Asn Gly Phe Gly Arg Ile Gly Arg Ile
1               5                   10                  15

Val Phe Arg Ala Ala Gln Glu Arg Ser Asp Ile Glu Ile Val Gly Ile
            20                  25                  30

Asn Asp Leu Leu Asp Ala Asn Tyr Met Ala Tyr Met Leu Lys Tyr Asp
        35                  40                  45

Ser Thr Gly Arg Phe Asn Gly Thr Val Glu Val Glu Glu Gly His Leu
    50                  55                  60

Ile Val Asn Gly Lys Lys Ile Arg Val Thr Ala Glu Arg Asp Pro Ala
65                  70                  75                  80

Asn Leu Lys Trp Asn Glu Ile Gly Val Asp Val Val Ala Glu Ala Thr
                85                  90                  95

Gly Leu Phe Leu Thr Asp Glu Thr Ala Arg Lys His Ile Ala Ala Gly
            100                 105                 110

Ala Lys Lys Val Val Met Thr Gly Pro Ser Lys Asp Ala Thr Pro Met
        115                 120                 125

Phe Val Met Gly Val Asn His Lys Asn Tyr Ala Gly Gln Ala Ile Val
    130                 135                 140

Ser Asn Ala Ser Cys Thr Thr Asn Cys Leu Ala Pro Leu Ala Lys Val
145                 150                 155                 160

Leu Asn Asp Asn Phe Gly Ile Val Glu Ala Leu Met Thr Thr Val His
                165                 170                 175

Ala Thr Thr Ala Thr Gln Lys Thr Val Asp Gly Pro Ser Met Lys Asp
            180                 185                 190
```

-continued

```
Trp Arg Gly Gly Arg Gly Ala Ser Gln Asn Ile Ile Pro Ser Ser Thr
        195                 200                 205

Gly Ala Ala Lys Ala Val Gly Lys Val Ile Glu Leu Asn Gly Lys Leu
    210                 215                 220

Thr Gly Met Ala Phe Arg Val Pro Thr Pro Asn Val Ser Val Val Asp
225                 230                 235                 240

Leu Thr Ala Arg Leu Ala Lys Pro Ala Thr Tyr Gln Gln Ile Cys Glu
                245                 250                 255

Val Met Lys Ala Ala Ser Glu Gly Glu Met Lys Gly Val Leu Gly Tyr
            260                 265                 270

Thr Asp Glu Ala Val Val Ser Thr Asp Phe Asn Gly Glu Val Cys Thr
        275                 280                 285

Ser Val Phe Asp Ala Asp Ala Gly Ile Ser Leu Asn Asp Asn Phe Val
    290                 295                 300

Lys Leu Val Ser Trp Tyr Asp Asn Glu Thr Gly Tyr Ser Asn Lys Val
305                 310                 315                 320

Leu Asp Leu Ile Ala His Ile Ser Lys
                325


<210> SEQ ID NO 2
<211> LENGTH: 139
<212> TYPE: DNA
<213> ORGANISM: Edwardsiella ictalrui

<400> SEQUENCE: 2

tatcgaataa attcacttgc gcatcgcggc acatcttgta agtttgagga ttatcacgcc      60

gttgcgcgcc gcactgacgc gcggcggccg atccgtaact cgtcaccatc caaggcagga     120

gtgcatatga aaaacgttg                                                  139


<210> SEQ ID NO 3
<211> LENGTH: 125
<212> TYPE: DNA
<213> ORGANISM: Escherichia coli

<400> SEQUENCE: 3

gctatcattg attaatttca cttgcgactt tggctgcttt ttgtatggtg aaagatgtgc      60

caagaggaga ccggcacatt tatacagcac acatctttgc aggaaaaaaa cgcttatgaa     120

aaatg                                                                 125


<210> SEQ ID NO 4
<211> LENGTH: 114
<212> TYPE: DNA
<213> ORGANISM: Salmonella typhimurium

<400> SEQUENCE: 4

ttgattaatt tcacttgcga ctttggctgc tttttgtatg gtgaaggatg cgccacagga      60

tactggcgcg catacacagc acatctcttt gcaggaaaaa aacgctatga aaaa           114


<210> SEQ ID NO 5
<211> LENGTH: 131
<212> TYPE: DNA
<213> ORGANISM: Yersinia pestis

<400> SEQUENCE: 5

cgtattggga tttgtgcgtt tgcaaccttg ccgcaacccc cacttacatt gggtaaccgc      60

gcgcagttat acaagacagg tatccataaa tcggtgtcac cttccaaggc agggcagtaa     120
```

-continued acatgaaaaa c 131

<210> SEQ ID NO 6
<211> LENGTH: 1278
<212> TYPE: DNA
<213> ORGANISM: Edwardsiella ictalrui

<400> SEQUENCE: 6
ttgcatgaaa gcgtcaatat tatgccgcgt agccagttta atggcgttga ttagcgcacg 60
ttggcgtatt ttcccgtgct gcgtctggcg ccgcgctgtg caaataaaaa tcaaaagcac 120
cacgggggag aaaaaacggt ggcgaacagt gagctattcc atgctgaagc gagacagtgc 180
gagacagtaa ggccaagcta tgctacaaac taagccgata tgcaccttta atggaatgga 240
gcgggtatag atcaagatcg ccggggatca tctcccttag gctatggaaa ctatattcga 300
caagtgcagt gctatagcag gttactaggc agttcccggc cccgtccagc ggggatgcgt 360
ttggcgcacc ggggatgcga taacaacaga ggataatagc gaatggttct cggcaaaccg 420
caaacagatc caactctcga atggttcctg tctcattgcc atattcacaa atatccgtcc 480
aaaagtacct tgattcacca aggtgaaaaa gcggagacgc tttattacat cgtaaaggga 540
tctgtagcgg tactgattaa ggatgaagag ggtaaggaga tgattctctc ctacctgaac 600
cagggcgact tcattggcga gctggggttg tttgaggaag ggcaggagcg tagtgcctgg 660
gtgcgggcga agactgcctg tgaggtggct gaaatttcct acaagaaatt ccgccagctg 720
atccaggtta acccagatat tttgatgcgt ctgtcttccc agatggcgcg tcgtctgcag 780
gtcacgtcag agaaagtcgg taacctggcc ttcctggatg tgacaggccg tattgctcag 840
acgctgttga atctggccaa gcagccagat gcgatgacgc acccagacgg catgcagatt 900
aaaatcaccc gtcaggagat cggccagatt gtgggttgct ctcgtgaaac ggtaggacgt 960
atcctgaaga tgctggagga tcagaacctg atctcggcac acggtaaaac catcgtcgtc 1020
tacgggacgc gttgattttg cgcccgcgcc gcacgagcgg cgcggaatct tcaacccatc 1080
cccaggatgg tgctcatgtg gcggcgcttt atctaccacc ctgaagtgaa ctatgccctg 1140
cgccagacgc tggttttgtg tctgccggtg ctgttcgggc tgatggtagg ccagctgcag 1200
caggggctgc tgttttctct ggtaccggtc tgctgtaata tcgccggtct tgacaccccc 1260
cataaacgct tctttaaa 1278

<210> SEQ ID NO 7
<211> LENGTH: 846
<212> TYPE: DNA
<213> ORGANISM: Edwardsiella ictalrui

<400> SEQUENCE: 7
tgtctgccgc ctgccggcgc gggacaccgt ttaatagccg gcaggtattt caaccatcaa 60
taaaaacgat aatgcgcagt tcgctgcgtc atttgtttct atcttcctca ttactcgtgg 120
gttatatcaa gcccgcgccg caggcacccc gttccgggca caccgcgcca cggttcccat 180
ttagagatat cggccttata atgaatctca ctattatttt ccgttcggta acggcccttg 240
ggcgctgccg ggcgctgtga caggacagaa tccgaatgac cgacaacaac accgcgttaa 300
agaaagctgg ccttaaagtc acgcttcccc gtctcaagat tctggaagta ctgcaagatc 360
ctacgtgcca tcatgtcagt gctgaagact tgtacaagaa gctaatcgat atgggcgagg 420
agatcggtct ggcgactgta taccgcgtac tcaaccagtt tgacgatgcc ggcatcgtga 480
cccgccataa ctttgagggc ggtaaatcgg tttttgagct gacccagcag caccaccacg 540

-continued

```
atcacctgat ctgcctggac tgcggcaagg tcatcgaatt cagcgatgag tccattgaga    600

agcgtcagcg cgaaatcgcg aaaaagcacg gcatccagct gaccaaccac agcctgtatc    660

tctacggcca ctgcgccgaa ggcgactgcc gtagcgatga gaccctgcac gatgaaaagg    720

cctgagtgac ctggcgccca cagcaggcga cgacgcggcc cagcggggcc gtttttttcc    780

ctgcgcgaca gcgggcaaaa aaaaggttca tcgcgcttta ccggggaacg ctgcttttat    840

cttcag                                                               846
```